United States Patent
Van Rompaey et al.

(10) Patent No.: US 11,530,271 B2
(45) Date of Patent: Dec. 20, 2022

(54) CD70 COMBINATION THERAPY

(71) Applicant: argenx BV, Ghent (BE)

(72) Inventors: Luc Van Rompaey, Ghent (BE); Mahan Moshir, Zwijnaarde (BE); Tim Delahaye, Zwijnaarde (BE); Piotr Zabrocki, Zwijnaarde (BE)

(73) Assignee: argenx BV, Ghent (BE)

( * ) Notice: Subject to any disclaimer, the term of this patent is extended or adjusted under 35 U.S.C. 154(b) by 285 days.

(21) Appl. No.: 16/249,480

(22) Filed: Jan. 16, 2019

(65) Prior Publication Data

US 2019/0241668 A1    Aug. 8, 2019

(30) Foreign Application Priority Data

Jan. 16, 2018 (GB) .................................. 1800649

(51) Int. Cl.
| | | |
|---|---|---|
| C07K 16/28 | (2006.01) | |
| A61P 35/02 | (2006.01) | |
| A61K 9/00 | (2006.01) | |
| A61K 39/00 | (2006.01) | |

(52) U.S. Cl.
CPC ........ *C07K 16/2875* (2013.01); *A61K 9/0019* (2013.01); *A61P 35/02* (2018.01); *C07K 16/2803* (2013.01); *C07K 16/2866* (2013.01); *A61K 2039/507* (2013.01); *C07K 2317/22* (2013.01); *C07K 2317/55* (2013.01)

(58) Field of Classification Search
CPC ............ C07K 16/2875; C07K 16/2803; C07K 16/2866; C07K 2317/55; C07K 2317/22; C07K 2317/92; C07K 2317/732; C07K 2317/734; C07K 2317/565; A61P 35/02; A61K 9/0019
See application file for complete search history.

(56) References Cited

U.S. PATENT DOCUMENTS

| | | |
|---|---|---|
| 5,573,924 A | 11/1996 | Beckmann et al. |
| 5,859,205 A | 1/1999 | Adair et al. |
| 6,500,633 B1 | 12/2002 | Compton |
| 6,844,422 B1 | 1/2005 | Niehrs et al. |
| 7,261,892 B2 | 8/2007 | Terret et al. |
| 7,491,390 B2 | 2/2009 | Law et al. |
| 7,641,903 B2 | 1/2010 | Law et al. |
| 7,662,387 B2 | 2/2010 | Law et al. |
| 7,723,477 B2 | 5/2010 | Gurney et al. |
| 7,728,114 B2 | 6/2010 | Mach et al. |
| 7,745,156 B2 | 6/2010 | Terret et al. |
| 7,745,419 B2 | 6/2010 | Oh et al. |
| 7,982,013 B2 | 7/2011 | Gurney et al. |
| 8,124,738 B2 | 2/2012 | Terret et al. |
| 8,324,361 B2 | 12/2012 | Gurney et al. |
| 8,455,622 B2 | 6/2013 | McDonagh et al. |
| 8,507,442 B2 | 8/2013 | Gurney et al. |
| 8,535,678 B2 | 9/2013 | Law et al. |
| 8,552,156 B2 | 10/2013 | Takayanagi et al. |
| 8,604,052 B2 | 12/2013 | Hood et al. |
| 8,647,623 B2 | 2/2014 | Takayanagi et al. |
| 8,663,642 B2 | 3/2014 | Law et al. |
| 8,765,913 B2 | 7/2014 | Gurney et al. |
| 8,834,882 B2 | 9/2014 | Silence et al. |
| 8,841,418 B2 | 9/2014 | Karsunky et al. |
| 9,556,270 B2 | 1/2017 | Takayanagi et al. |
| 9,605,070 B2 | 3/2017 | Sabatos-Peyton et al. |
| 9,631,026 B2 | 4/2017 | Karsunky et al. |
| 2003/0148321 A1 | 8/2003 | Pecker |
| 2005/0118656 A1 | 6/2005 | Terrett et al. |
| 2006/0115832 A1 | 6/2006 | Hoon |
| 2006/0275844 A1 | 12/2006 | Linke |
| 2007/0072178 A1 | 3/2007 | Haferlach |
| 2008/0025989 A1 | 1/2008 | Law et al. |
| 2008/0138341 A1 | 6/2008 | Law et al. |
| 2008/0280297 A1 | 11/2008 | Dalla-Favera |
| 2009/0028872 A1 | 1/2009 | Terret et al. |
| 2009/0074772 A1 | 3/2009 | Law et al. |
| 2009/0148942 A1 | 6/2009 | McDonagh et al. |
| 2009/0232806 A1 | 9/2009 | Law et al. |
| 2010/0129362 A1 | 5/2010 | Law et al. |
| 2010/0150925 A1 | 6/2010 | Law et al. |
| 2010/0150950 A1 | 6/2010 | Coccia et al. |
| 2010/0158910 A1 | 6/2010 | Law et al. |
| 2010/0183636 A1 | 7/2010 | Law et al. |

(Continued)

FOREIGN PATENT DOCUMENTS

| | | |
|---|---|---|
| WO | WO 1994/005691 A1 | 3/1994 |
| WO | WO 2003/046581 A2 | 6/2003 |

(Continued)

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*

(Continued)

*Primary Examiner* — Jessica H Roark
*Assistant Examiner* — Cheom-Gil Cheong
(74) *Attorney, Agent, or Firm* — Dechert LLP; Andrew T. Wilkins; Victoria E. Pedanou

(57) ABSTRACT

The present invention relates to combination therapies for the treatment of malignancy, particularly myeloid malignancy such as acute myeloid leukemia (AML). The combination therapies may include an antibody molecule that binds to CD70 and at least one antibody molecule that binds to a leukemic stem cell target. Preferred leukemic stem cell targets are TIM-3, IL1R3/IL1RAP and CD47.

24 Claims, 11 Drawing Sheets

Specification includes a Sequence Listing.

(56) References Cited

U.S. PATENT DOCUMENTS

| | | |
|---|---|---|
| 2010/0267626 A1 | 10/2010 | Cheung et al. |
| 2010/0278779 A1 | 11/2010 | Zeldis |
| 2011/0190157 A1 | 8/2011 | Kipps |
| 2012/0093805 A1 | 4/2012 | Kubota |
| 2012/0178111 A1 | 7/2012 | Diamandis |
| 2013/0078237 A1 | 3/2013 | Delaney et al. |
| 2013/0243795 A1 | 9/2013 | Chen et al. |
| 2014/0141016 A1 | 5/2014 | Silence et al. |
| 2014/0147450 A1 | 5/2014 | Silence et al. |
| 2014/0235843 A1 | 8/2014 | Silence et al. |
| 2015/0086521 A1 | 3/2015 | Godfrin |
| 2015/0132324 A1 | 5/2015 | Cong et al. |
| 2018/0244792 A1* | 8/2018 | Duncan ................ A61P 11/00 |

FOREIGN PATENT DOCUMENTS

| | | |
|---|---|---|
| WO | WO 2004/073656 A2 | 9/2004 |
| WO | WO 2006/044643 A2 | 4/2006 |
| WO | WO 2006/113909 A2 | 10/2006 |
| WO | WO 2007/038637 A2 | 4/2007 |
| WO | WO 2007/146968 A2 | 12/2007 |
| WO | WO 2008/074004 A2 | 6/2008 |
| WO | WO 2010/001251 A2 | 1/2010 |
| WO | WO 2010/014948 A1 | 2/2010 |
| WO | WO 2011/061119 A1 | 5/2011 |
| WO | WO 2011/080350 A1 | 7/2011 |
| WO | WO 2012/098407 A1 | 7/2012 |
| WO | WO 2012/098407 A2 | 7/2012 |
| WO | WO 2012/123586 A1 | 9/2012 |
| WO | WO 2014/100772 A1 | 6/2014 |
| WO | WO 2015/138600 A2 | 9/2015 |
| WO | WO 2016/111947 A2 | 7/2016 |
| WO | WO 2017/079116 A1 | 5/2017 |
| WO | WO 2017/079116 A2 | 5/2017 |
| WO | WO 2017/134140 A1 | 8/2017 |
| WO | WO 2017/021354 A1 | 9/2017 |
| WO | WO 2017/160954 A1 | 9/2017 |
| WO | WO 2018/229303 A1 | 12/2018 |
| WO | WO 2019/141732 A1 | 7/2019 |

OTHER PUBLICATIONS

Dempke et al., "Second—and third—generation drugs for immuno-oncology treatment—The more the better?", European Journal of Cancer Mar. 2017, vol. 74, pp. 55-72.

Nolte et al., "Timing and tuning of CD27-CD70 interactions: the impact of signal strength in setting the balance between adaptive responses and immunopathology", Immunological Reviews (2009) vol. 229, pp. 2016-2231.

Ragusa et al., "Expression profile and specific network features of the apoptotic machinery explain relapse of acute myeloid leukemia after chemotherapy", BMC Cancer (2010) 10: 377, <http://www.biomedcentral.com/1471-2407/10/377>.

Ryan et al., "Targeting pancreatic and ovarian carcinomas using the auristatin-based anti-CD70 antibody-drug conjugate SGN-75", British Journal of Cancer (2010) 103, pp. 676-684/.

Askmyr et al. (2013) "Selective killing of candidate AML stem cells by antibody targeting of IL1RAP," Blood, 121(18):3709-3713.

Bertrand et al. (2013) "The Costimulatory Molecule CD70 is Regulated by Distinct Molecular Mechanisms and is Associated with Overall Survival in Diffuse Large B-cell Lymphoma," Genes, Chromosomes and Cancer, 52:764-774.

Bosman et al. (2016) "Constitutive NF-κB activation in AML: Causes and treatment strategies," Critical Reviews in Oncology/Hematology, 98:35-44.

Boursalian et al. (2009) "Targeting CD70 for human therapeutic use," Adv. Exp. Med. Biol., Chapter 7, 108-119.

Caron et al. (1992) "Engineered Humanized Dimeric Forms of IgG Are More Effective Antibodies," J. Exp. Med., 176:1191-1195.

Chahlavi et al. (2005) "Glioblastomas Induce T-Lymphocyte Death by Two Distinct Pathways Involving Gangliosides and CD70," Cancer Res., 65(12):5428-5438.

Chan et al. (2010) "Therapeutic antibodies for autoimmunity and inflammation," Nature Reviews: Immunology, 10:301-316.

Claus et al. (2012) "CD27 Signaling Increases the Frequency of Regulatory T Cells and Promotes Tumor Growth," Cancer Res., 72(14):3664-3676.

Colovai et al. (2007) "Expression of Inhibitory Receptor ILT3 on Neoplastic B Cells Is Associated with Lymphoid Tissue Involvement Leukemia," Cytometry Part B (Clinical Cytometry) 72B:354-362.

Deveraux et al. (1984) "A comprehensive set of sequence analysis programs for the VAX," Nucleic Acids Research, 12(1):387-395.

Diegemann et al. (2006) "Immune Escape for Renal Cell Carcinoma: CD70 Mediates Apoptosis in Lymphocytes," Neoplasia, 8(11):933-938.

Dohner et al. (2017) "Diagnosis and management of AML in adults: 2017 ELN recommendations from an international expert panel," Blood, 129(4):66 pages.

Goncalves-Silva et al. (2015) "Differential expression and biochemical activity of the immune receptor Tim-3 in healthy and malignant human myeloid cells," Oncotarget, 6(32):33823-33833.

Goto et al. (2012) "Serum soluble CD27 level is associated with outcome in patients with diffuse large B-cell lymphoma treated with rituximab, cyclophosphamide, doxorubicin, vincristine and prednisolone," Leukemia and Lymphoma, 53(8):1494-1500.

Han et al. (2005) "Increased prevalence of activated CD70+ CD4+ T cells in the periphery of patients with systematic lupus erythematosus," Lupus 14:598-606.

Hanekamp et al. (2017) "Leukemic stem cells: identification and clinical application," Int. J. Hematol., 105:549-557.

Held-Feindt et al. (2002) "CD70/CD27 Ligand, a member or the TNF family, is expressed in human brain tumors," Int. J. Cancer, 98:352-356.

Hinton et al. (2006) "An Engineered Human IgG1 Antibody with Longer Serum Half-Life," The Journal of Immunology, 176:346-356.

Hishima et al. (2000) "CD70 Expression in Thymic Carcinoma," The American Journal of Surgical Pathology, 2:742-746.

Holliger et al. (2005) "Engineered antibody fragments and the rise of single domains," Nature Biotechnology, 23(9):1126-1136.

International Search Report and Written Opinion for International Application No. PCT/EP2019/051058, dated Mar. 21, 2019.

Jacobs et al. (2015) "Unlocking the potential of CD70 as a novel immunotherapeutic target for non-small cell lung cancer," Oncotarget, 6(15):13462-13475.

Japp et al. (2015) "Dysfunction of PSA-specific CD8+ cells in prostate cancer patients correlates with CD38 and Tim-3 expression," Cancer of Immunol Immunother, 8 pages.

Jaras et al. (2010) "Isolation and killing of candidate chronic myeloid leukemia stem cells by antibody targeting of IL-1 receptor accessory protein," PNAS, 107(37):16280-16285.

Jilaveanu et al. (2012) "CD70 Expression Patterns in Renal Cell Carcinoma," Human Pathol., 43(9):1394-1399.

Junker et al. (2005) "CD70: A new tumor specific biomarker for renal cell carcinoma," 173:2150-2153.

Kikushige et al. (2010) "TIM-3 is a promising target to selectively kill acute myeloid leukemia stem cells," Cell Stem Cell, 7:708-717.

Kikushige et al. (2015) "A TIM-3/Gal-9 Autocrine Stimulatory Loop Drives Self-Renewal of Human Myeloid Leukemia Stem Cells and Leukemic Progression," Cell Stem Cell, 17:341-352.

Kikushige et al. (2013) "TIM-3 as a novel therapeutic target for eradicating acute myelogenous leukemia stem cells," Int. J. Hematol., 98:627-633.

Lee et al. (2007) "Unchecked CD70 expression on T cells lowers threshold for T-cell activation in rheumatoid arthritis," J. Immunol., 179(4):2609-2615.

Lens et al. (1999) "Aberrant expression and reverse signalling of CD70 on malignant B cells," British Journal of Hematology, 106:491-503.

Natsume et al. (2009) "Improving effector functions of antibodies for cancer treatment: Enhancing ADCC and CDC," Drug Design Development and Therapy, 3:7-16.

(56) References Cited

OTHER PUBLICATIONS

O'Donnell et al. (2017) "Acute Myeloid Leukemia, Version 3," Journal of the National Comprehensive Cancer Network, 15(7):926-957.
Perna et al. (2017) "Integration Proteomics and Transcriptomics for Systematic Combinatorial Chimeric Antigen Receptor Therapy of AML," Cancer Cell, 32:506-519.
Pollye et al. (2017) "Therapeutic targeting of acute myeloid leukemia stem cells," Blood, 129(12):1627-1635.
Richardson et al. (2014) "Epigenetics in 2013: DNA methylation and miRNA-key roles in systematic autoimmunity," Nat. Rev. Rheumatol., 10(2):72-74.
Van Doorn et al. (2004) "Aberrant Expression of the Tyrosine Kinase Receptor EphA4 and the Transcription Factor Twist in Sezary Syndrome Identified by Gene Expression Analysis," Cancer Research, 64:5578-5586.
Wajant, H. (2006) "Therapeutic targeting of CD70 and CD27," Expert Opinion on Therapeutic Targets, 20(8):959-973.
Wang et al. (2012) "Distinctive Features of the Differentiated Phenotype and Infiltration of Tumor-reactive Lymphocytes in Clear Cell Renal Cell Carcinoma," Cancer Res., 72(23):6119-6129.
Yamane-Ohnuki et al. (2009) "Production of therapeutic antibodies with controlled fucosylation," mAbs, 1(3):230-236.
Achour et al. (2008) "Tetrameric and homodimeric camelid IgGs originate from the same IgH locus," J. Immunol. 181:2001-2009.
Adam et al. 'CD70 (TNFSF7) is Expressed at High Prevalence in Renal Cell Carcinomas and is Rapidly Internalised on Antibody Binding' British J of Cancer; Aug. 7, 2006, vol. 95, No. 3, pp. 298-306.
Aftimos et al., "Phase I Dose-Escalation Study of the Anti-CD70 Antibody ARGX-110 in Advanced Malignancies", Clinical Cancer Research, Nov. 2017, 23(21):6411-6420.
Appel et al (Molecular Diversity, 1996, 2:29-34).
Argenx [online], 2017, "ARGX-110", https://web.archive.org/web/20170505150651/www.argenx.com:80/en-GB/content/argx-110/18/ [accessed May 5, 2017].
Arroyo Hornero et al., "CD70 expression determines the therapeutic efficacy of expanded human regulatory T cells", Communications Biology, 2020, vol. 3, No. 375, pp. 1-17.
Baba et al., "Highly Enhanced Expression of CD70 on Human T-Lymphotropic Virus Type 1-Carrying T-Cell Lines and Adult T-Cell Leukemia Cells", Journal of Virology, Apr. 2008, pp. 3843-3852.
Baccarani et al. (2006) "Evolving concepts in the management of chronic myeloid leukemia: recommendations from an expert panel on behalf of the European LeukemiaNet," Blood 108:1809-1820.
Baxevanis, "Antibody-based cancer therapy", Expert Opinion: Drug Discovery, 2008, vol. 3, No. 4, pp. 441-452.
Belloc et al. (2007) "Imatinib and nilotinib induce apoptosis of chronic myeloid leukemia cells through a Bim-dependant pathway modulated by cytokines," Cancer Biol. Ther. 6:912-919.
Brown et al. (1996) "Tolerance of single, but not multiple, amino acid replacements in antibody VH CDR 2: a means of minimizing B cell wastage from somatic hypermutation?" J Immunol. 156(9):3285-3291.
Brugnoni et al., "CD70 expression on T-cell subpopulations: study of normal individuals and patients with chronic immune activation", Immunology Letters, 1997, vol. 55, pp. 99-104.
CAS Registry No. 0641571-10-0. [Last Accessed Dec. 16, 2016].
CAS Registry No. 1165740-62-4. [Last Accessed Dec. 16, 2016].
CAS Registry No. 302962-49-8. [Last Accessed Dec. 16, 2016].
CAS Registry No. 379231-04-6. [Last Accessed Dec. 16, 2016].
CAS Registry No. 380843-75-4. [Last Accessed Dec. 16, 2016].
CAS Registry No. 639089-54-6. [Last Accessed Dec. 16, 2016].
CAS Registry No. 664993-53-7. [Last Accessed Dec. 16, 2016].
CAS Registry No. 82115-62-6. [Last Accessed Dec. 16, 2016].
CAS Registry No. 859212-16-1. [Last Accessed Dec. 16, 2016].
CAS Registry No. 943319-70-8. [Last Accessed Dec. 16, 2016].
Clevers et al. (2012) "Wnt/β-catenin signaling and disease," Cell. 149:1192-1205.

clinicaltrials.gov (First received Dec. 16, 2011) "AMG 172 First in Human Study in Patients With Kidney Cancer," U.S. National Institutes of Health. ClinicalTrials.gov Identifier: NCT01497821.
clinicaltrials.gov (First received Dec. 3, 2013) "A Study of Vantictumab (OMP-18R5) in Combination With Nab-Paclitaxel and Gemcitabine in Previously Untreated Stage IV Pancreatic Cancer," U.S. National Institutes of Health. ClinicalTrials.gov Identifier: NCT02005315.
clinicaltrials.gov (First received Jul. 17, 2011) "Phase I Clinical Study of CWP232291 in Acute Myeloid Leukemia Patients," U.S. National Institutes of Health. ClinicalTrials.gov Identifier: NCT01398462.
clinicaltrials.gov (First received May 4, 2011) "A Study of LGK974 in Patients With Malignancies Dependent on Wnt Ligands," U.S. National Institutes of Health. ClinicalTrials.gov Identifier: NCT01351103. Accessible on the Internet at URL: http://www.ebi.ac.uk/arrayexpress/experiments/E-MEXP-480. [Last Accessed Dec. 15, 2016].
clinicaltrials.gov (First received Oct. 25, 2013) "A Study of Vantictumab (OMP-18R5) in Combination With Paclitaxel in Locally Recurrent or Metastatic Breast Cancer," U.S. National Institutes of Health. ClinicalTrials.gov Identifier: NCT01973309.
clinicaltrials.gov (First received Sep. 27, 2013) "A Study of Vantictumab (OMP-18R5) in Combination With Docetaxel in Patients With Previously Treated NSCLC," U.S. National Institutes of Health. ClinicalTrials.gov Identifier: NCT01957007.
clinicaltrials.gov, "A Study of ARGX-110 in Combination with Azacytidine in Participants with Newly Diagnosed Acute Myeloid Leukemia (AML) or High Risk Myelodysplastic Syndrome (MDS)", ClinicalTrials.gov Identifier No. NCT03030612, Jan. 25, 2017.
Colman, "Effects of amino acid sequence changes on antibody-antigen interactions", Research in Immunology, 1994, vol. 145, pp. 33-36.
Coluccia et al. (2007) "Bcr-Abl stabilizes β-catenin in chronic myeloid leukemia through its tyrosine phosphorylation," EMBO J. 26:1456-1466.
Combined Search and Examination Report dated Feb. 8, 2019 in related Application No. GB1709677.7 (4 pages).
Corbin et al. (2011) "Human chronic myeloid leukemia stem cells are insensitive to imatinib despite inhibition of BCR-ABL activity," J. Clin. Invest. 121:396-409.
Cortes et al. (Nov. 29, 2012) "Ponatinib in refractory Philadelphia chromosome-positive leukemias," N. Engl. J. Med. 367:2075-2088.
Damschroder et al. (2004) "Analysis of human and primate CD2 molecules by protein sequence and epitope mapping with anti-human CD2 antibodies," Mol. Immunol. 41(10):985-1000.
Deininger (2007) "Optimizing therapy of chronic myeloid leukemia," Exp. Hematol. 35:144-154.
Denoeud et al., "Role of CD27/CD70 pathway of activation in immunity and tolerance", Journal of Leukocyte Biology, Feb. 2011, vol. 89, pp. 195-203.
Druker et al. (2001) "Activity of a Specific Inhibitor of the BCR-ABL Tyrosine Kinase in the Blast Crisis of Chronic Myeloid Leukemia and Acute Lymphoblastic Leukemia with the Philadelphia Chromosome," N. Engl. J. Med. 344:1038-1042.
Druker et al. (2001) "Efficacy and Safety of a Specific Inhibitor of the BCR-ABL Tyrosine Kinase in Chronic Myeloid Leukemia," N. Engl. J. Med. 344:1031-1037.
Edwards et al., "The remarkable flexibility of the human antibody repertoire; isolation of over one thousand different antibodies to a single protein, BLyS", J. Mol. Biol., 2003, 334(1): 103-118.
EMBL-EBI Database [Online] (Last updated May 3, 2014) "E-MEXP-480—Transcription profiling of D34+ BCR-ABL+ cells of CML patients in chronic phase or blast crisis to identify differentially expressed stage-specific genes," Accession No. E-MEXP-480. Accessible on the Internet at URL: http://www.ebi.ac.uk/arrayexpress/experiments/E-MEXP-480. [Last Accessed Dec. 15, 2016].
Faderl et al. (1999) "The Biology of Chronic Myeloid Leukemia," N. Engl. J. Med. 341:164-172.
Frank, Immunology and Evolution of Infectious Disease, Chapter 4 "Specificity and Cross-Reactivity," Princeton University Press, 2002.

(56) References Cited

OTHER PUBLICATIONS

French et al: 'Eradication of Lymphoma by CD8 T Cells Following Anti-CD40 Monoclonal Antibody Therapy is Critically Dependant on CD27 Costimulation'. Blood; Jun. 1, 2007, vol. 109, No. 11, pp. 4810-4815.
Genbank Database [Online] (Nov. 2, 2016) "RecName: Full=Proto-oncogene Wnt-1; AltName: Full=Proto-oncogene Int-1 homolog; Flags: Precursor," Accession No. P04628. Accessible on the Internet at URL: https://www.ncbi.nlm.nih.gov/protein/P04628. [Last Accessed Dec. 16, 2016].
Glouchkova et al. (2009) "The CD70/CD27 pathway is critical for stimulation of an effective cytotoxic T cell response against B cell precursor acute lymphoblastic leukemia", J Immunol 182: 718-725.
Gregory et al., "Wnt/Ca2+/NFAT signaling maintains survival of Ph+ leukemia cells upon inhibition of Bcr-Abl", Cancer Cell, 2010, 18: 74-87.
Groves et al. (2006) "Affinity maturation of phage display antibody populations using ribosome display," Journal of Immunological Methods. 313:129-139.
Hamad et al., "Emerging Therapeutic Strategies for Targeting Chronic Myeloid Leukemia Stem Cells", Stem Cells International, vol. 2013, Article ID 724360, 12 pages, 2013.
Harlow et al. (1988) Antibodies, A Laboratory Manual. Cold Spring Harbor laboratory, pp. 37-47.
Harris et al., "Assessing Genetic Heterogeneity in Production Cell Lines: Detection by Peptide Mapping of a Low Level Tyr to Gln Sequence Variant in a Recombinant Antibody", Biotechnology, 1993, vol. 11, pp. 1293-1297.
Hsiao et al. (2008) "Tankyrase function at telomeres, spindle poles, and beyond," Biochimie. 90:83-92.
Hu et al., "β-Catenin is essential for survival of leukemic stem cells insensitive to kinase inhibition in mice with BCR-ABL-induced chronic myeloid leukemia", Leukemia, 2009, 23: 109-116.
International Preliminary Report on Patentability for PCT International Patent Application No. PCT/EP2019/085982, dated Jun. 19, 2020.
International Preliminary Report on Patentability for PCT International Patent Application No. PCT/EP2012/054733, dated Sep. 17, 2013.
International Search Report and Written Opinion for PCT International Patent Application No. PCT/EP2018/066144, dated Aug. 17, 2018.
International Search Report and Written Opinion for PCT International Patent Application No. PCT/EP2019/051058, dated Mar. 21, 2019.
International Search Report and Written Opinion for PCT International Patent Application No. PCT/EP2019/085982, dated Mar. 20, 2020.
International Search Report for PCT International Patent Application No. PCT/EP2012/054733, dated Jul. 26, 2012.
Israel et al. (2005) "Anti-CD70 antibodies: a potential treatment for EBV+ CD70-expressing lymphomas," Mol. Cancer Ther. 4:2037-2044.
Jacobs et al. (2015) "CD70: An emerging target in cancer immunotherapy," Pharmacology and Therapeutics 155:1-10.
Jan et al. (2011) "Prospective separation of normal and leukemic stem cells based on differential expression of TIM3, a human acute myeloid leukemia stem cell marker," PNAS, 108(12):5009-5014.
Kang et al. (2015) "The ITM-containing receptor LAIR1 is essential for acute myeloid leukemia development," Nat. Cell Biol., 17(5):665-677.
Kapinas et al. (2010) "miR-29 modulates Wnt signaling in human osteoblasts through a positive feedback loop," J. Biol. Chem. 285:25221-25231.
Katoh et al. (2007) "WNT signaling pathway and stem cell signaling network," Clin. Cancer Res. 13(14):4042-4045.
Klimka et al., "Human anti-CD30 recombinant antibodies by guided phage antibody selection using cell panning", British Journal of Cancer, 2000, 83:252-260.
Lefranc et al. (1999) "IMGT, the international ImMunoGeneTics database," Nucleic Acids Res. 27:209-212.
Lens et al. (1999) "Aberrant expression and reverse signaling of CD70 on malignant B cells," British Journal of Hematology, 106:491-503.
Li et al. (Feb. 14, 2012) "Activation of p53 by SIRT1 inhibition enhances elimination of CML leukemia stem cells in combination with imatinib," Cancer Cell. 21:266-281.
Liu et al. (2010) "Sp1/NFκB/HDAC/miR-29b Regulatory Network in KIT-driven Myeloid Leukemia," Cancer Cell. 17:333-347.
Lugo et al. (1990) "Tyrosine kinase activity and transformation potency of bcr-abl oncogene products," Science. 247:1079-1082.
Ma et al. (2008) "IL-22 is required for Th17 cell-mediated pathology in a mouse model of psoriasis-like skin inflammation," J Clin. Invest. 118:597-607.
MacCallum et al. (1996) "Antibody-antigen interactions: contact analysis and binding site topography," J. Mol. Biol. 262:732-745.
Malia et al., "Epitope mapping and structural basis for the recognition of phosphorylated tau by the anti-tau antibody AT8", Proteins, 2016, 84(4): 427-434.
Manocha et al., "Blocking CD27-CD70 Costimulatory Pathway Suppresses Experimental Colitis", The Journal of Immunology, 2009, vol. 183, pp. 270-276.
Martin et al. (1996) "Structural Families in Loops of Homologous Proteins: Automatic Classification, Modelling and Application to Antibodies," J. Mol. Biol. 263(5):800-15.
Memorandum, Feb. 22, 2018, Robert W. Bahr, Deputy Commissioner for Patent Examination Policy, pp. 1-2. (Year: 2018).
Meyer et al., "New insights in Type I and II CD20 antibody mechanisms-of-action with a panel of novel CD20 antibodies", British Journal of Haematology, 2018, 180(6), 808-820.
Naresh et al., "Use of the World Health Organization (WHO) classification of non-Hodgkin's lymphoma in Mumbai, India: a review of 200 consecutive cases by a panel of five expert hematopathologists", Leukemia & Lymphoma, Aug. 2004, 45(8):1569-1577.
Negger (2001) "Human Vλ Germline Sequences (VBase)," University of Zurich. Accessible on the Internet at URL: http://www.bioc.uzh.ch/antibody/Sequences/Germlines/VBase_hVL.html. [Last Accessed Dec. 4, 2017].
Nilsson et al. (2005) "Expression of CD27-CD70 on Early B Cell Progenitors in the Bone Marrow: Implication and Therapy of Childhood ALL," Experimental Hematology, 33:1500-1507.
O'Hare et al. (2009) "AP24534, a Pan-BCR-ABL Inhibitor for Chronic Myeloid Leukemia, Potently Inhibits the T315I Mutant and Overcomes Mutation-Based Resistance," Cancer Cell. 16:401-412.
Oelke et al. (2004) "Overexpression of CD70 and Overstimulation of IgG Synthesis by Lupus T Cells and T Cells Treated with DNA Methylation Inhibitors," Arthritis and Rheumatism, 50(6):1850-1860.
Oflazoglu et al., "Blocking of CD27-CD70 Pathway by Anti-CD70 Antibody Ameliorates Joint Disease in Murine Collagen-Induced Arthritis", The Journal of Immunology, 2009, vol. 183, pp. 3770-3777.
Ohaegbulam et al. (2015) "Human cancer immunotherapy with antibodies to the PD-1 and PD-L1 pathway," Trends Mol. Med., 21(1):24-33.
Paul, "Structure and Function of Immunoglobulins", Fundamental Immunology, 3rd Edition, Raven Press, New York, 1993, pp. 292-295.
Petrau et al. (2014) "CD70: A potential target in breast cancer?," Journal of Cancer, 5:761-764.
Pollyea et al. (2017) "Therapeutic targeting of acute myeloid leukemia stem cells," Blood, 129(12):1627-1635.
Ponce et al. (2017) "SIRPa-antibody fusion proteins stimulate phagocytosis and promote elimination of acute myeloid leukemia cells," Oncotarget, 8(7):11284-11301.
Presta et al. (2008) "Molecular engineering and design of therapeutic antibodies," Current Opinion in Immunology, 20:460-470.
Ragusa et al., "Expression profile and specific network features of the apoptotic machinery explain relapse of acute myeloid leukemia after chemotherapy", BMC Cancer, 2010, 10: Article 377.

(56) References Cited

OTHER PUBLICATIONS

Riether et al. (2017) "CD70/CD27 signaling promotes blast stemness and is a viable therapeutic target in acute myeloid leukemia," J. Exp. Med., 214(2):359-380.
Riether et al., "CD27 Signaling Promotes the Proliferation of Human Acute Myeloid Leukemia Cells", Respiration, 2013, vol. 85, No. 6, p. 571, Abstract P192.
Ring et al. (2017) "Anti-SIRPα antibody immunotherapy enhances neutrophil and macrophage antitumor activity," PNAS, 114(49):E10578-E10585.
Rudikoff et al. "Single amino acid substitution altering antigen-binding specificity", Proceedings of the National Academy of Sciences, 1982, vol. 79, No. 6, pp. 1979-1983.
Ryan et al. (2010) "Targeting pancreatic and ovarian carcinomas using the auristatin-based anti-CD70 antibody-drug conjugate SGN-75," British Journal of Cancer. 103:676-684.
Sabat et al. (Jan. 2014) "Therapeutic opportunities of the IL-22-IL-22R1 system," Nat. Rev. Drug Discov. 13(1):21-38.
Sakuishi et al. (2010) "Targeting Tim-3 and PD-1 pathways to reverse T cell exhaustion and restore anti-tumor immunity," J. Exp. Med., 207(10):2187-2194.
Sawalha et al., "Defective DNA methylation and CD70 overexpression in CD4+ T cells in MRL/lpr lupus-prone mice", European Journal of Immunology, 2007, vol. 37, pp. 1407-1413.
Schürch et al. (Feb. 1, 2012) "CD27 signaling on chronic myelogenous leukemia stem cells activates Wnt target genes and promotes disease progression," J. Clin. Invest. 122:624-638.
Shao et al. (2011) "Combination or monoclonal antibodies with DST inhibits accelerated rejection mediated by memory T cells to induce long-lived heart allograft acceptance in mice," Immunology Letters 138:122-128.
Shopes et al. (1992) "A genetically engineered human IgG mutant with enhanced cytolytic activity," The Journal of Immunology, 148:2918-2922.
Shultz et al. (2005) "Human Lymphoid and Myeloid Cell Development in NOD/LtSz-scid IL2Rγnull Mice Engrafted with Mobilized Human Hemopoietic Stem Cells," J. Immunol. 174:6477-6489.
Silence et al. (2014) "ARGX-110, a highly potent antibody targeting CD70, eliminates tumors via both enhanced ADCC and immune checkpoint blockade," mAbs, 6(2):523-532.
Sloan et al. (2004) "Detection of Differentially Expressed Genes in an Isogenic Breast Metastasis Model using RNA Arbitrarily Primed-Polymerase Chain Reaction Coupled with Array Hybridization (RAP-Array)," American Journal of Pathology, 164(1):315-323.
Tatusova et al. (1999) "Blast 2 sequences—a new tool for comparing protein and nucleotide sequences," FEMS Microbiol Lett. 174:247-250.
Teh et al., "Enhancing venetoclax activity in acute myeloid leukemia by co-targeting MCL1", Leukemia, Jul. 28, 2017, 32(2):303-312.
Tesselaar et al. (1997) "Characterization of murine CD70, the ligand of the TNF receptor family member CD27," J. Immunol. 159:4959-4965.
Tesselaar et al. (2003) "Expression of the murine CD27 ligand CD70 in vitro and in vivo," J. Immunol. 170:33-40.
Theocharides et al. (2012) "Disruption of SIRPα signaling in macrophages eliminates human acute myeloid leukemia stem cells in xenografts," J. Exp. Med., 209(10):1883-1899.
Urlaub et al (1980) "Isolation of Chinese hamster cell mutants deficient in dihydrofolate reductase activity," Proc. Natl. Acad. Sci. USA. 77:4216-20.
Vaccaro et al. (2005) "Engineering the FC region of immunoglobulin G to modulate in vivo antibody levels," Nature Biotechnology, 23(10):1283-1288.
Vajdos et al. (2002) "Comprehensive Functional Maps of the Antigen-binding Site of an Anti-ErbB2 Antibody Obtained with Shotgun Scanning Mutagenesis," J. Mol. Biol. 320(2):415-428.
Van Regenmortel (Journal of Immunological Methods, 1998, 216:37-48).
Waaler et al. (Mar. 22, 2012) "A novel tankyrase inhibitor decreases canonical Wnt signaling in colon carcinoma cells and reduces tumor growth in conditional APC mutant mice," Cancer Res. 72(11):2822-2832.
Wang et al. (2007) "Antibody Structure, Instability, and Formulation," Journal of Pharmaceutical Sciences, 96(1):1-26.
Wang et al. (2017) "Circular RNAs in human cancer," Molecular Cancer, 16(25):8 pages.
Ward et al., Binding activities of a repertoire of single immunoglobin variable domains secreted from *Escherichia coli*, Nature, 1989, 341:544-546.
Webster's New World Dictionary, Third College Edition, 1988, see p. 1067 (Year: 1988).
Wei et al., "Midostaurin, enasidenib, CPX-351, gemtuzumab ozogamicin, and venetoclax bring new hope to AML", Blood, Dec. 7, 2017, 130(23): 2469-2474.
Weinberg, "Tumors resemble wound-healing sites", The Biology of Cancer, 2007, Chapter 13.2-13.3, pp. 536-539.
Williams et al. (1996) "Sequence and evolution of the human germline V lambda repertoire," J. Mol. Biol. 264:220-232.
Wischhusen et al. (2002) "Identification of CD70-mediated Apoptosis of Immune Effector Cells as a Novel Immune Escape Pathway of Human Glioblastoma," Cancer Research, 62:2592-2599.
Yamane-Ohnuke et al. (2009) "Production of therapeutic antibodies with controlled fucosylation," mAbs, 1(3):230-236.
Yanagisawa et al., "Effects of anti-CD70 mAb on Thieler's murine encephalomyelitis virus-induced demyelinating disease", Brain Research, 2010, vol. 1317, pp. 236-245.
Yang et al. (2014) "TGF-β upregulates CD70 expression and induces exhaustion of effector memory T cells in B-cell non-Hodgkin's lymphoma," Leukemia, 28(9):1872-1884.
Yeung et al. (2009) "Engineering Human IgG1 Affinity to Human Neonatal Fc Receptor: Impact of Affinity Improvement on Pharmacokinetics in Primates," The Journal of Immunology, 182:7663-7671.
Zahnd et al. (2010) "Computational analysis of off-rate selection experiments to optimize affinity maturation by directed evolution," Protein Engineering: Design & Selection. 23(4):175-184.
Zalevsky et al. (2010) "Enhanced antibody half-life improves in vivo activity," Nat. Biotechnol., 28(2):157-159.
Zhang et al. (2010) "Effective targeting of quiescent chronic myelogenous leukemia stem cells by histone deacetylase inhibitors in combination with imatinib mesylate," Cancer Cell. 17:427-442.
Zhou et al. (2011) "Histone modifications and methyl-CpG-binding domain protein levels at the TNFSF7 (CD70) promoter in SLE CD4+ T cells," Lupus, 20:1365-1371.

\* cited by examiner

SEQUENCE LISTING

```
<160> NUMBER OF SEQ ID NOS: 136

<210> SEQ ID NO 1
<211> LENGTH: 5
<212> TYPE: PRT
<213> ORGANISM: Artificial
<220> FEATURE:
<223> OTHER INFORMATION: Synthetic peptide

<400> SEQUENCE: 1

Val Tyr Tyr Met Asn
1               5

<210> SEQ ID NO 2
<211> LENGTH: 17
<212> TYPE: PRT
<213> ORGANISM: Artificial
<220> FEATURE:
<223> OTHER INFORMATION: Synthetic peptide

<400> SEQUENCE: 2

Asp Ile Asn Asn Glu Gly Gly Thr Thr Tyr Tyr Ala Asp Ser Val Lys
1               5                   10                  15

Gly

<210> SEQ ID NO 3
<211> LENGTH: 13
<212> TYPE: PRT
<213> ORGANISM: Artificial
<220> FEATURE:
<223> OTHER INFORMATION: Synthetic peptide
```

<400> SEQUENCE: 3

Asp Ala Gly Tyr Ser Asn His Val Pro Ile Phe Asp Ser
1               5                   10

<210> SEQ ID NO 4
<211> LENGTH: 122
<212> TYPE: PRT
<213> ORGANISM: Artificial
<220> FEATURE:
<223> OTHER INFORMATION: Synthetic peptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Asp Ile Asn Asn Glu Gly Gly Thr Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Tyr Ser Asn His Val Pro Ile Phe Asp Ser Trp
            100                 105                 110

Gly Gln Gly Thr Leu Val Thr Val Ser Ser
        115                 120

<210> SEQ ID NO 5
<211> LENGTH: 14
<212> TYPE: PRT
<213> ORGANISM: Artificial
<220> FEATURE:
<223> OTHER INFORMATION: Synthetic peptide

<400> SEQUENCE: 5

Gly Leu Lys Ser Gly Ser Val Thr Ser Asp Asn Phe Pro Thr
1               5                   10

<210> SEQ ID NO 6
<211> LENGTH: 7
<212> TYPE: PRT
<213> ORGANISM: Artificial
<220> FEATURE:
<223> OTHER INFORMATION: Synthetic peptide

<400> SEQUENCE: 6

Asn Thr Asn Thr Arg His Ser
1               5

<210> SEQ ID NO 7
<211> LENGTH: 10
<212> TYPE: PRT
<213> ORGANISM: Artificial
<220> FEATURE:
<223> OTHER INFORMATION: Synthetic peptide

<400> SEQUENCE: 7

Ala Leu Phe Ile Ser Asn Pro Ser Val Glu
1               5                   10

<210> SEQ ID NO 8
<211> LENGTH: 111
<212> TYPE: PRT
<213> ORGANISM: Artificial
<220> FEATURE:
<223> OTHER INFORMATION: Synthetic peptide

<400> SEQUENCE: 8

Gln Ala Val Val Thr Gln Glu Pro Ser Leu Thr Val Ser Pro Gly Gly
1               5                   10                  15

Thr Val Thr Leu Thr Cys Gly Leu Lys Ser Gly Ser Val Thr Ser Asp
            20                  25                  30

Asn Phe Pro Thr Trp Tyr Gln Gln Thr Pro Gly Gln Ala Pro Arg Leu
        35                  40                  45

Leu Ile Tyr Asn Thr Asn Thr Arg His Ser Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ala Glu Tyr Phe Cys Ala Leu Phe Ile Ser Asn
                85                  90                  95

Pro Ser Val Glu Phe Gly Gly Gly Thr Gln Leu Thr Val Leu Gly
            100                 105                 110

<210> SEQ ID NO 9
<211> LENGTH: 123
<212> TYPE: PRT
<213> ORGANISM: Artificial
<220> FEATURE:
<223> OTHER INFORMATION: Synthetic peptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser His Ile Asn Ser Gly Gly Gly Asn Thr Lys Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Thr Leu Lys Pro Glu Asp Thr Ala Val Tyr Tyr Cys
                85                  90                  95

Ala Lys Asp Val Ser Gly Gly Tyr Tyr Gly Thr Tyr Ala Leu Asp Ala
            100                 105                 110

Trp Gly Gln Gly Thr Gln Val Val Val Ser Ser
        115                 120

<210> SEQ ID NO 10
<211> LENGTH: 106
<212> TYPE: PRT
<213> ORGANISM: Artificial
<220> FEATURE:
<223> OTHER INFORMATION: Synthetic peptide

<400> SEQUENCE: 10

Ser Tyr Glu Leu Thr Gln Ser Pro Ser Val Ser Val Ala Leu Lys Gln
1               5                   10                  15

Thr Ala Lys Ile Thr Cys Gly Gly Asp Asn Ile Gly Ser Lys Ser Ala

```
                20                  25                  30
Gln Trp Tyr Gln Gln Lys Pro Gly Gln Ala Pro Val Leu Val Ile Tyr
            35                  40                  45

Ala Asp Ser Arg Arg Pro Ser Gly Ile Pro Glu Arg Phe Ser Gly Ser
 50                  55                  60

Asn Ser Gly Asn Thr Ala Thr Leu Thr Ile Ser Gly Ala Gln Ala Glu
 65                  70                  75                  80

Asp Glu Ala Asp Tyr Tyr Cys Gln Val Trp Asp Ser Ser Ala Ala Val
            85                  90                  95

Phe Gly Gly Gly Thr His Leu Thr Val Leu
            100                 105

<210> SEQ ID NO 11
<211> LENGTH: 121
<212> TYPE: PRT
<213> ORGANISM: Artificial
<220> FEATURE:
<223> OTHER INFORMATION: Synthetic peptide

<400> SEQUENCE: 11

Glu Val Gln Val Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Asp Ile Asn Ser Gly Gly Gly Ser Thr Val Tyr Thr Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Asp Asp Thr Ala Val Tyr Tyr Cys
            85                  90                  95

Ala Thr Gly Gly Ser Tyr Tyr Ser Tyr Arg Leu Phe Asp Tyr Trp Gly
            100                 105                 110

Gln Gly Thr Gln Val Thr Val Ser Ser
            115                 120

<210> SEQ ID NO 12
<211> LENGTH: 114
<212> TYPE: PRT
<213> ORGANISM: Artificial
<220> FEATURE:
<223> OTHER INFORMATION: Synthetic peptide

<400> SEQUENCE: 12

Asp Ile Gln Met Thr Gln Ser Pro Ser Ser Val Ile Val Ser Ala Gly
 1               5                  10                  15

Glu Lys Val Thr Ile Asn Cys Lys Ser Ser Gln Ser Val Leu Asp Ser
            20                  25                  30

Ser Asn Gln Lys Asn Tyr Leu Ala Trp Tyr Gln Gln Arg Leu Gly Gln
            35                  40                  45

Ser Pro Arg Leu Leu Ile Tyr Trp Ala Ser Thr Arg Glu Ser Gly Val
 50                  55                  60

Pro Asp Arg Phe Ser Gly Ser Gly Ser Thr Thr Asp Phe Thr Leu Thr
 65                  70                  75                  80

Ile Ser Ser Phe Gln Pro Glu Asp Ala Ala Val Tyr Tyr Cys Gln Gln
            85                  90                  95
```

```
Gly Tyr Ser Val Pro Val Thr Phe Gly Gln Gly Thr Lys Val Glu Leu
                100                 105                 110
Lys Arg
```

<210> SEQ ID NO 13
<211> LENGTH: 124
<212> TYPE: PRT
<213> ORGANISM: Artificial
<220> FEATURE:
<223> OTHER INFORMATION: Synthetic peptide

<400> SEQUENCE: 13

```
Gln Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Tyr Trp Val Arg Gln Ala Pro Gly Lys Gly Leu Glu Trp Val
        35                  40                  45

Ser Thr Ile Asn Thr Asn Gly Ala Ile Thr Leu Tyr Ala Asp Asn Val
    50                  55                  60

Lys Asp Arg Phe Thr Val Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Val Lys Leu Ser Gly Tyr Pro His Pro Tyr Tyr Ala Met Asp
            100                 105                 110

Tyr Trp Gly Lys Gly Thr Leu Val Thr Val Ser Ser
        115                 120
```

<210> SEQ ID NO 14
<211> LENGTH: 115
<212> TYPE: PRT
<213> ORGANISM: Artificial
<220> FEATURE:
<223> OTHER INFORMATION: Synthetic peptide

<400> SEQUENCE: 14

```
Asn Phe Met Leu Thr Gln Pro Pro Ser Leu Ser Gly Ser Leu Gly Gln
1               5                   10                  15

Ser Ala Arg Leu Thr Cys Thr Leu Gly Ser Gly Asn Ser Ile Gly Ala
            20                  25                  30

His Thr Ile Ser Trp Tyr Gln Gln Lys Ala Gly Ser Pro Pro Arg Tyr
        35                  40                  45

Leu Leu Asn Tyr Tyr Ser Asp Ser Ser Asn His Gln Ala Ser Gly Val
    50                  55                  60

Pro Ser Arg Phe Ser Gly Ser Lys Asp Ser Thr Asn Ala Gly Leu
65                  70                  75                  80

Leu Leu Ile Ser Gly Leu Gln Pro Glu Asp Glu Ala Asp Tyr Tyr Cys
                85                  90                  95

Ala Ala Gly Asp Gly Ser Gly Thr Val Phe Gly Gly Thr Lys Leu
            100                 105                 110

Thr Val Leu
        115
```

<210> SEQ ID NO 15
<211> LENGTH: 122
<212> TYPE: PRT
<213> ORGANISM: Artificial
<220> FEATURE:

<223> OTHER INFORMATION: Synthetic peptide

<400> SEQUENCE: 15

```
Gln Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Thr Thr Ser
            20                  25                  30

Asp Asp Ala Trp Ser Trp Ile Arg Gln Pro Ala Gly Lys Gly Leu Glu
        35                  40                  45

Trp Met Gly Val Ile Ala Tyr Asp Gly Ser Thr Arg Tyr Ser Pro Ser
    50                  55                  60

Leu Gln Ser Arg Thr Ser Ile Ser Arg Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Thr Lys Gly Val Gly Thr Trp Ala Leu Asp Ala Trp
            100                 105                 110

Gly Gln Gly Thr Leu Val Thr Val Ser Ser
        115                 120
```

<210> SEQ ID NO 16
<211> LENGTH: 114
<212> TYPE: PRT
<213> ORGANISM: Artificial
<220> FEATURE:
<223> OTHER INFORMATION: Synthetic peptide

<400> SEQUENCE: 16

```
Glu Ile Val Leu Thr Gln Ser Pro Ser Ser Val Thr Ala Ser Val Gly
1               5                   10                  15

Glu Lys Val Thr Ile Asn Cys Lys Ser Ser Gln Ser Val Leu Ser Ser
            20                  25                  30

Ser Asn Gln Lys Asn Tyr Leu Ser Trp Tyr Gln Gln Arg Leu Gly Gln
        35                  40                  45

Ser Pro Arg Leu Leu Ile Thr Trp Ala Ser Thr Arg Glu Ser Gly Val
    50                  55                  60

Pro Asp Arg Phe Ser Gly Ser Gly Ser Thr Thr Asp Phe Thr Leu Thr
65                  70                  75                  80

Ile Ser Ser Phe Gln Pro Glu Asp Ala Ala Val Tyr Tyr Cys Gln Gln
                85                  90                  95

Gly Tyr Gly Ala Pro Leu Thr Phe Gly Gln Gly Thr Lys Val Glu Leu
            100                 105                 110

Lys Arg
```

<210> SEQ ID NO 17
<211> LENGTH: 122
<212> TYPE: PRT
<213> ORGANISM: Artificial
<220> FEATURE:
<223> OTHER INFORMATION: Synthetic peptide

<400> SEQUENCE: 17

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Leu Glu Trp Val
        35                  40                  45
```

Ser Thr Ile Asn Ser Gly Gly Ser Thr Asn Tyr Ala Asp Ser Met
        50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Ala Arg Ser Pro Tyr Tyr Thr Arg Val Pro Leu Tyr Asp Tyr Trp
            100                 105                 110

Gly Gln Gly Thr Gln Val Thr Val Ser Ser
            115                 120

<210> SEQ ID NO 18
<211> LENGTH: 110
<212> TYPE: PRT
<213> ORGANISM: Artificial
<220> FEATURE:
<223> OTHER INFORMATION: Synthetic peptide

<400> SEQUENCE: 18

Gln Ala Val Val Thr Gln Glu Pro Ser Leu Ser Val Ser Leu Gly Gly
 1               5                  10                  15

Thr Val Thr Leu Thr Cys Gly Leu Arg Ser Gly Ser Val Thr Thr Ser
                20                  25                  30

Asn Tyr Pro Gly Trp Phe Lys Gln Thr Pro Gly Gln Ala Pro Arg Thr
            35                  40                  45

Leu Ile Phe Gly Ala Ser Ser Arg His Ser Gly Val Pro Ser Arg Tyr
 50                  55                  60

Ser Gly Ser Ile Ser Gly Asn Lys Ala Ala Leu Thr Ile Thr Gly Ala
 65                  70                  75                  80

Glu Pro Glu Asp Glu Ala Asp Tyr Tyr Cys Ala Leu Asn Lys Gly Thr
                85                  90                  95

Tyr Thr Asp Val Phe Gly Gly Gly Thr Lys Leu Thr Val Leu
            100                 105                 110

<210> SEQ ID NO 19
<211> LENGTH: 125
<212> TYPE: PRT
<213> ORGANISM: Artificial
<220> FEATURE:
<223> OTHER INFORMATION: Synthetic peptide

<400> SEQUENCE: 19

Glu Val Gln Leu Gln Glu Ser Gly Pro Gly Leu Val Lys Pro Ser Gln
 1               5                  10                  15

Thr Leu Ser Leu Thr Cys Thr Val Ser Gly Ala Ser Val Thr Thr Arg
                20                  25                  30

Tyr Asn Tyr Trp Ser Trp Ile Arg Gln Pro Pro Gly Lys Gly Leu Glu
            35                  40                  45

Trp Met Gly Ala Ile Thr Tyr Ser Gly Ser Thr Tyr Tyr Ser Pro Ser
     50                  55                  60

Leu Lys Ser Arg Thr Ser Ile Ser Arg Asp Thr Ser Lys Asn Gln Phe
 65                  70                  75                  80

Thr Leu Gln Leu Ser Ser Val Thr Pro Glu Asp Thr Ala Val Tyr Tyr
                85                  90                  95

Cys Ala Thr Glu Gly Ser Ser Ser Thr Gly Val Ser Arg Tyr Ser Phe
            100                 105                 110

Gly Ser Trp Gly Gln Gly Thr Gln Val Thr Val Ser Ser

```
<210> SEQ ID NO 20
<211> LENGTH: 111
<212> TYPE: PRT
<213> ORGANISM: Artificial
<220> FEATURE:
<223> OTHER INFORMATION: Synthetic peptide

<400> SEQUENCE: 20

Ala Thr Met Leu Thr Gln Ser Pro Gly Ser Leu Ser Val Val Pro Gly
1               5                   10                  15

Glu Ser Ala Ser Ile Ser Cys Lys Ala Ser Gln Ser Leu Thr His Thr
            20                  25                  30

Asp Gly Thr Thr Ala Leu Tyr Trp Leu Gln Gln Lys Pro Gly Gln Arg
        35                  40                  45

Pro Gln Leu Leu Ile Tyr Glu Val Ser Val Arg Ala Ser Gly Val Pro
    50                  55                  60

Asp Arg Phe Thr Gly Ser Gly Ser Gly Ser Asp Phe Thr Leu Lys Ile
65                  70                  75                  80

Asn Gly Val Lys Ala Glu Asp Ala Gly Val Tyr Tyr Cys Ala Gln Val
                85                  90                  95

Ala Tyr Tyr Pro Thr Phe Gly Gln Gly Thr Lys Val Glu Leu Lys
            100                 105                 110

<210> SEQ ID NO 21
<211> LENGTH: 118
<212> TYPE: PRT
<213> ORGANISM: Artificial
<220> FEATURE:
<223> OTHER INFORMATION: Synthetic peptide

<400> SEQUENCE: 21

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Asn
            20                  25                  30

Arg Tyr Leu Trp Thr Trp Ile Arg Gln Thr Pro Gly Lys Gly Leu Glu
        35                  40                  45

Trp Val Gly Ala Ile Ala Tyr Ser Gly Arg Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Thr Leu Gln Leu Ser Ser Val Thr Pro Glu Asp Thr Gly Val Tyr Tyr
                85                  90                  95

Cys Ala His Phe Thr Gly Trp Gly Gly Tyr Tyr Trp Gly Gln Gly Thr
            100                 105                 110

Gln Val Thr Val Ser Ser
        115

<210> SEQ ID NO 22
<211> LENGTH: 110
<212> TYPE: PRT
<213> ORGANISM: Artificial
<220> FEATURE:
<223> OTHER INFORMATION: Synthetic peptide

<400> SEQUENCE: 22

Gln Ser Ala Leu Thr Gln Pro Pro Ser Val Ser Gly Thr Leu Gly Lys
1               5                   10                  15
```

Thr Val Thr Ile Ser Cys Ala Gly Thr Ser Ser Asp Ile Gly Gly Tyr
            20                  25                  30

Asn Ser Val Ser Trp Tyr Gln Gln Leu Pro Gly Thr Ala Pro Lys Leu
        35                  40                  45

Leu Ile Tyr Glu Val Asn Lys Arg Ala Ser Gly Ile Pro Asp Arg Phe
    50                  55                  60

Ser Gly Ser Lys Ser Gly Asn Thr Ala Ser Leu Ser Ile Ser Gly Leu
65                  70                  75                  80

Gln Ser Glu Asp Glu Ala Asp Tyr Tyr Cys Ala Ser Tyr Arg Ser Ala
                85                  90                  95

Asn Asn Val Val Phe Gly Gly Gly Thr Lys Leu Thr Val Leu
            100                 105                 110

<210> SEQ ID NO 23
<211> LENGTH: 122
<212> TYPE: PRT
<213> ORGANISM: Artificial
<220> FEATURE:
<223> OTHER INFORMATION: Synthetic peptide

<400> SEQUENCE: 23

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Gly Pro Glu Trp Val
        35                  40                  45

Ser Thr Ile Asn Ser Gly Gly Gly Ser Thr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Arg Ser Leu Tyr Tyr Thr Arg Val Pro Met Tyr Asp Tyr Trp
            100                 105                 110

Gly Gln Gly Thr Gln Val Thr Val Ser Lys
        115                 120

<210> SEQ ID NO 24
<211> LENGTH: 110
<212> TYPE: PRT
<213> ORGANISM: Artificial
<220> FEATURE:
<223> OTHER INFORMATION: Synthetic peptide

<400> SEQUENCE: 24

Gln Ala Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Asn
            20                  25                  30

Asn Tyr Pro Gly Trp Phe Gln Gln Thr Pro Gly Gln Ala Pro Arg Thr
        35                  40                  45

Leu Ile Tyr Ser Thr Ser Ser Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Asp Ile Gly Ser

```
                     85                  90                  95

Tyr Thr Ala Val Phe Gly Gly Thr His Leu Thr Val Leu
                    100                 105                 110

<210> SEQ ID NO 25
<211> LENGTH: 125
<212> TYPE: PRT
<213> ORGANISM: Artificial
<220> FEATURE:
<223> OTHER INFORMATION: Synthetic peptide

<400> SEQUENCE: 25

Glu Val Gln Leu Val Gln Pro Gly Ala Glu Leu Arg Asn Pro Gly Ala
1               5                   10                  15

Ser Val Lys Val Ser Cys Lys Ala Ser Gly Tyr Thr Phe Thr Met Tyr
                20                  25                  30

Tyr Ile Asp Trp Val Arg Gln Ala Pro Gly Gln Gly Leu Glu Trp Met
            35                  40                  45

Gly Arg Ile Asp Pro Glu Asp Gly Gly Thr Lys Tyr Ala Gln Lys Phe
        50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Asp Thr Ala Val Tyr Tyr Cys
                85                  90                  95

Ala Arg Ile Pro Asn Gly Gly Ser Tyr Tyr Thr Pro Tyr Asp Tyr
            100                 105                 110

Asp Tyr Trp Gly Gln Gly Thr Gln Val Thr Val Ser Ser
        115                 120                 125

<210> SEQ ID NO 26
<211> LENGTH: 110
<212> TYPE: PRT
<213> ORGANISM: Artificial
<220> FEATURE:
<223> OTHER INFORMATION: Synthetic peptide

<400> SEQUENCE: 26

Gln Ala Val Val Thr Gln Glu Pro Ser Leu Ser Val Ser Pro Gly Gly
1               5                   10                  15

Thr Val Thr Leu Thr Cys Gly Leu Thr Ser Gly Ser Val Thr Ser Ser
                20                  25                  30

Asn Tyr Pro Gly Trp Tyr Arg Gln Thr Pro Gly Gln Ala Pro Arg Pro
            35                  40                  45

Leu Ile Tyr Asn Thr Asn Ser Arg His Pro Gly Val Pro Ser Arg Tyr
        50                  55                  60

Ser Gly Ser Ile Ser Glu Asn Lys Ala Thr Leu Thr Ile Thr Gly Ala
65                  70                  75                  80

Glu Pro Glu Asp Glu Ala Asp Tyr Tyr Cys Ala Leu His Lys Gly Ser
                85                  90                  95

Tyr Thr Ala Val Phe Gly Gly Gly Thr His Leu Thr Val Leu
            100                 105                 110

<210> SEQ ID NO 27
<211> LENGTH: 121
<212> TYPE: PRT
<213> ORGANISM: Artificial
<220> FEATURE:
<223> OTHER INFORMATION: Synthetic peptide

<400> SEQUENCE: 27
```

-continued

```
Gln Val Gln Leu Gln Glu Ser Gly Gly Gly Leu Val Gln Pro Gly Gly
1               5                   10                  15

Ser Leu Thr Leu Ser Cys Ala Ala Ser Gly Phe Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ala Gly Gly Thr Ser Tyr Tyr Ala Asp Ser Val
50                  55                  60

Lys Gly Arg Phe Thr Ile Ser Arg Asp Ser Ala Lys Asn Thr Leu Val
65                  70                  75                  80

Leu Gln Met Asn Ser Leu Lys Pro Glu Asp Thr Ala Val Tyr Tyr Cys
                85                  90                  95

Ala Lys Lys Arg Gln Asn Phe Trp Ser Glu Gly Tyr Asp Ser Trp Gly
            100                 105                 110

Gln Gly Thr Gln Val Thr Val Ser Ser
            115                 120

<210> SEQ ID NO 28
<211> LENGTH: 110
<212> TYPE: PRT
<213> ORGANISM: Artificial
<220> FEATURE:
<223> OTHER INFORMATION: Synthetic peptide

<400> SEQUENCE: 28

His Ser Ala Val Thr Gln Pro Pro Ser Val Ser Gly Ser Pro Gly Lys
1               5                   10                  15

Ala Val Thr Ile Ser Cys Val Gly Ser Ser Asp Val Gly Tyr Gly
            20                  25                  30

Asp Tyr Val Ser Trp Tyr Gln Gln Leu Pro Gly Met Ala Pro Lys Leu
        35                  40                  45

Leu Ile Tyr Asp Val Glu Lys Arg Ala Ser Gly Ile Pro Asp Arg Phe
50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Ser Asp
                85                  90                  95

Ser Asn Phe Val Phe Gly Gly Gly Thr His Leu Ala Val Leu
            100                 105                 110

<210> SEQ ID NO 29
<211> LENGTH: 120
<212> TYPE: PRT
<213> ORGANISM: Artificial
<220> FEATURE:
<223> OTHER INFORMATION: Synthetic peptide

<400> SEQUENCE: 29

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Asp Met Ser Trp Val Arg Gln Ala Pro Gly Lys Gly Pro Glu Trp Val
        35                  40                  45

Ser Arg Ile Thr Ser Gly Gly Gly Ser Thr Tyr Ala Asp Ser Val Lys
50                  55                  60

Gly Arg Phe Thr Ile Ser Arg Asp Asn Ala Lys Asn Thr Leu Ser Leu
```

```
                65                  70                  75                  80
Gln Met Asn Ser Leu Lys Ser Glu Asp Thr Ala Val Tyr Tyr Cys Ala
                    85                  90                  95

Ala Gly Gln Tyr Ser Asp Gly Tyr Tyr Pro Tyr Asp Tyr Trp Gly Gln
                100                 105                 110

Gly Thr Gln Val Thr Val Ser Ser
                115                 120

<210> SEQ ID NO 30
<211> LENGTH: 107
<212> TYPE: PRT
<213> ORGANISM: Artificial
<220> FEATURE:
<223> OTHER INFORMATION: Synthetic peptide

<400> SEQUENCE: 30

Asp Ile Val Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
                20                  25                  30

Leu Ala Trp Tyr Gln Gln Lys Pro Gly Gln Gly Pro Lys Leu Leu Ile
            35                  40                  45

Tyr Gly Ala Ser Arg Leu Glu Pro Gly Val Pro Ser Arg Phe Ser Gly
    50                  55                  60

Ser Gly Ser Gly Thr Ser Phe Thr Leu Thr Ile Ser Gly Val Glu Ala
65                  70                  75                  80

Glu Asp Leu Ala Thr Tyr Tyr Cys Leu Gln Asp Tyr Ser Trp Pro Tyr
                85                  90                  95

Ser Phe Gly Ser Gly Thr Arg Leu Glu Ile Lys
                100                 105

<210> SEQ ID NO 31
<211> LENGTH: 114
<212> TYPE: PRT
<213> ORGANISM: Artificial
<220> FEATURE:
<223> OTHER INFORMATION: Synthetic peptide

<400> SEQUENCE: 31

Glu Leu Gln Val Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
                20                  25                  30

Asp Met Ser Trp His Arg Gln Ala Pro Arg Lys Gly Pro Glu Trp Val
            35                  40                  45

Ser Thr Ile Ser Ala Gly Gly Arg Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Phe Cys
                85                  90                  95

Thr Lys Ile Val Leu Asp Ser Trp Gly Gln Gly Thr Gln Val Thr Val
                100                 105                 110

Ser Ser

<210> SEQ ID NO 32
<211> LENGTH: 111
<212> TYPE: PRT
```

```
<213> ORGANISM: Artificial
<220> FEATURE:
<223> OTHER INFORMATION: Synthetic peptide

<400> SEQUENCE: 32

Asp Val Val Leu Thr Gln Thr Pro Gly Ser Leu Ser Val Val Pro Gly
1               5                   10                  15

Glu Ser Ala Ser Ile Ser Cys Lys Ala Ser Gln Ser Leu Ile His Ile
            20                  25                  30

Asp Gly Lys Thr Tyr Leu Tyr Trp Leu Leu Gln Lys Pro Gly Arg Arg
        35                  40                  45

Pro Glu Leu Leu Ile Tyr Gln Val Ser Asn His Glu Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala Gln Ala
                85                  90                  95

Thr Tyr Tyr Pro Ser Phe Gly Ser Gly Thr Arg Leu Glu Ile Lys
            100                 105                 110

<210> SEQ ID NO 33
<211> LENGTH: 117
<212> TYPE: PRT
<213> ORGANISM: Artificial
<220> FEATURE:
<223> OTHER INFORMATION: Synthetic peptide

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Thr Met Ser Trp Val Arg Gln Val Pro Gly Lys Gly Leu Glu Trp Ile
        35                  40                  45

Ser Gly Ile Ser Gly Asn Gly Gly Arg Thr Asp Tyr Val Glu Pro Ile
    50                  55                  60

Glu Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Thr Ser Pro Gln Ser Leu Asp Tyr Trp Gly Gln Gly Thr Gln
            100                 105                 110

Val Thr Val Ser Ser
        115

<210> SEQ ID NO 34
<211> LENGTH: 113
<212> TYPE: PRT
<213> ORGANISM: Artificial
<220> FEATURE:
<223> OTHER INFORMATION: Synthetic peptide

<400> SEQUENCE: 34

Asp Ile Val Met Thr Gln Ser Pro Ser Ser Val Thr Ala Ser Val Gly
1               5                   10                  15

Glu Lys Val Thr Ile Asn Cys Lys Ser Ser Gln Ser Val Val Ser Gly
            20                  25                  30

Ser Asn Gln Lys Ser Tyr Leu Asn Trp Tyr Gln Gln Arg Pro Gly Gln
        35                  40                  45
```

```
Pro Pro Arg Leu Leu Ile Tyr Tyr Ala Ser Thr Gln Glu Ser Gly Ile
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser Ala Pro Tyr Asn Phe Gly Ser Gly Thr Arg Leu Glu Ile
            100                 105                 110

Lys

<210> SEQ ID NO 35
<211> LENGTH: 114
<212> TYPE: PRT
<213> ORGANISM: Artificial
<220> FEATURE:
<223> OTHER INFORMATION: Synthetic peptide

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
                20                  25                  30

Asp Met Ser Trp Val Arg Gln Ala Pro Gly Lys Gly Pro Glu Trp Val
            35                  40                  45

Ser Thr Ile Ser Ala Gly Gly Arg Thr Tyr Tyr Ala Asp Ser Val
    50                  55                  60

Lys Asp Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys Val Val Ile Asp Tyr Trp Gly Gln Gly Thr Gln Val Thr Val
            100                 105                 110

Ser Ser

<210> SEQ ID NO 36
<211> LENGTH: 111
<212> TYPE: PRT
<213> ORGANISM: Artificial
<220> FEATURE:
<223> OTHER INFORMATION: Synthetic peptide

<400> SEQUENCE: 36

Asp Val Val Leu Thr Gln Thr Pro Gly Ser Leu Ser Val Val Pro Gly
1               5                   10                  15

Glu Ser Ala Ser Ile Ser Cys Lys Ala Ser Gln Ser Leu Val His Thr
                20                  25                  30

Asp Gly Lys Thr Tyr Val Tyr Trp Leu Leu Gln Lys Pro Gly Gln Arg
            35                  40                  45

Pro His Leu Leu Ile Tyr Gln Val Ser Asn His Glu Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala Gln Ala
                85                  90                  95

Thr Tyr Tyr Pro Ser Phe Gly Ser Gly Thr Arg Leu Glu Ile Lys
            100                 105                 110
```

<210> SEQ ID NO 37
<211> LENGTH: 125
<212> TYPE: PRT
<213> ORGANISM: Artificial
<220> FEATURE:
<223> OTHER INFORMATION: Synthetic peptide

<400> SEQUENCE: 37

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Pro Glu Trp Val
        35                  40                  45

Ser Gly Ile Asn Thr Ser Gly Gly Thr Thr Ser Tyr Ala Ala Ser Val
    50                  55                  60

Lys Gly Arg Phe Thr Val Ser Arg Asp Asn Ala Lys Asn Thr Leu Ser
65                  70                  75                  80

Leu Gln Met Asn Ser Leu Glu Pro Glu Asp Thr Ala Val Tyr Tyr Cys
                85                  90                  95

Val Lys His Ile Arg Trp Ser Gly Ser Asn Tyr Tyr Tyr Gly Met
            100                 105                 110

Asp Tyr Trp Gly Lys Gly Thr Leu Val Thr Val Ser Ser
        115                 120                 125
```

<210> SEQ ID NO 38
<211> LENGTH: 110
<212> TYPE: PRT
<213> ORGANISM: Artificial
<220> FEATURE:
<223> OTHER INFORMATION: Synthetic peptide

<400> SEQUENCE: 38

```
Gln Ala Val Leu Thr Gln Pro Pro Ser Val Ser Gly Ser Pro Gly Gln
1               5                   10                  15

Arg Phe Thr Ile Ser Cys Thr Gly Ser Asn Arg Asn Ile Gly Asn Asn
            20                  25                  30

Tyr Val Asn Trp Tyr Gln Gln Leu Pro Gly Thr Ala Pro Lys Leu Leu
        35                  40                  45

Ile Tyr Ser Asp Asn Leu Arg Thr Ser Gly Val Pro Ala Arg Phe Ser
    50                  55                  60

Ala Ser Lys Ser Gly Thr Thr Ser Ser Leu Thr Ile Ser Gly Leu Gln
65                  70                  75                  80

Ala Glu Asp Glu Ala Val Tyr Tyr Cys Ser Ser Trp Asp Asp Ser Leu
                85                  90                  95

Ser Gly Ala Val Phe Gly Gly Gly Thr His Leu Thr Val Leu
            100                 105                 110
```

<210> SEQ ID NO 39
<211> LENGTH: 5
<212> TYPE: PRT
<213> ORGANISM: Artificial
<220> FEATURE:
<223> OTHER INFORMATION: Synthetic peptide

<400> SEQUENCE: 39

```
Ser Tyr Ala Met Ser
1               5
```

```
<210> SEQ ID NO 40
<211> LENGTH: 17
<212> TYPE: PRT
<213> ORGANISM: Artificial
<220> FEATURE:
<223> OTHER INFORMATION: Synthetic peptide

<400> SEQUENCE: 40

His Ile Asn Ser Gly Gly Asn Thr Lys Tyr Ala Asp Ser Val Lys
1               5                   10                  15

Gly

<210> SEQ ID NO 41
<211> LENGTH: 14
<212> TYPE: PRT
<213> ORGANISM: Artificial
<220> FEATURE:
<223> OTHER INFORMATION: Synthetic peptide

<400> SEQUENCE: 41

Asp Val Ser Gly Gly Tyr Tyr Gly Thr Tyr Ala Leu Asp Ala
1               5                   10

<210> SEQ ID NO 42
<211> LENGTH: 17
<212> TYPE: PRT
<213> ORGANISM: Artificial
<220> FEATURE:
<223> OTHER INFORMATION: Synthetic peptide

<400> SEQUENCE: 42

Asp Ile Asn Ser Gly Gly Gly Ser Thr Val Tyr Thr Asp Ser Val Lys
1               5                   10                  15

Gly

<210> SEQ ID NO 43
<211> LENGTH: 12
<212> TYPE: PRT
<213> ORGANISM: Artificial
<220> FEATURE:
<223> OTHER INFORMATION: Synthetic peptide

<400> SEQUENCE: 43

Gly Gly Ser Tyr Tyr Ser Tyr Arg Leu Phe Asp Tyr
1               5                   10

<210> SEQ ID NO 44
<211> LENGTH: 5
<212> TYPE: PRT
<213> ORGANISM: Artificial
<220> FEATURE:
<223> OTHER INFORMATION: Synthetic peptide

<400> SEQUENCE: 44

Asn Tyr Trp Met Tyr
1               5

<210> SEQ ID NO 45
<211> LENGTH: 17
<212> TYPE: PRT
<213> ORGANISM: Artificial
<220> FEATURE:
<223> OTHER INFORMATION: Synthetic peptide

<400> SEQUENCE: 45

Thr Ile Asn Thr Asn Gly Ala Ile Thr Leu Tyr Ala Asp Asn Val Lys
```

```
                     -continued 1               5                   10                  15
Asp <210> SEQ ID NO 46
<211> LENGTH: 15
<212> TYPE: PRT
<213> ORGANISM: Artificial
<220> FEATURE:
<223> OTHER INFORMATION: Synthetic peptide

<400> SEQUENCE: 46

Val Lys Leu Ser Gly Tyr Pro His Pro Tyr Tyr Ala Met Asp Tyr
1               5                   10                  15

<210> SEQ ID NO 47
<211> LENGTH: 7
<212> TYPE: PRT
<213> ORGANISM: Artificial
<220> FEATURE:
<223> OTHER INFORMATION: Synthetic peptide

<400> SEQUENCE: 47

Thr Ser Asp Asp Ala Trp Ser
1               5

<210> SEQ ID NO 48
<211> LENGTH: 16
<212> TYPE: PRT
<213> ORGANISM: Artificial
<220> FEATURE:
<223> OTHER INFORMATION: Synthetic peptide

<400> SEQUENCE: 48

Val Ile Ala Tyr Asp Gly Ser Thr Arg Tyr Ser Pro Ser Leu Gln Ser
1               5                   10                  15

<210> SEQ ID NO 49
<211> LENGTH: 12
<212> TYPE: PRT
<213> ORGANISM: Artificial
<220> FEATURE:
<223> OTHER INFORMATION: Synthetic peptide

<400> SEQUENCE: 49

Thr Lys Gly Val Gly Gly Thr Trp Ala Leu Asp Ala
1               5                   10

<210> SEQ ID NO 50
<211> LENGTH: 5
<212> TYPE: PRT
<213> ORGANISM: Artificial
<220> FEATURE:
<223> OTHER INFORMATION: Synthetic peptide

<400> SEQUENCE: 50

Ser Tyr Asp Met Ser
1               5

<210> SEQ ID NO 51
<211> LENGTH: 17
<212> TYPE: PRT
<213> ORGANISM: Artificial
<220> FEATURE:
<223> OTHER INFORMATION: Synthetic peptide

<400> SEQUENCE: 51
```

Thr Ile Asn Ser Gly Gly Gly Ser Thr Asn Tyr Ala Asp Ser Met Lys
1               5                   10                  15

Gly

<210> SEQ ID NO 52
<211> LENGTH: 13
<212> TYPE: PRT
<213> ORGANISM: Artificial
<220> FEATURE:
<223> OTHER INFORMATION: Synthetic peptide

<400> SEQUENCE: 52

Arg Ser Pro Tyr Tyr Thr Arg Val Pro Leu Tyr Asp Tyr
1               5                   10

<210> SEQ ID NO 53
<211> LENGTH: 7
<212> TYPE: PRT
<213> ORGANISM: Artificial
<220> FEATURE:
<223> OTHER INFORMATION: Synthetic peptide

<400> SEQUENCE: 53

Thr Arg Tyr Asn Tyr Trp Ser
1               5

<210> SEQ ID NO 54
<211> LENGTH: 16
<212> TYPE: PRT
<213> ORGANISM: Artificial
<220> FEATURE:
<223> OTHER INFORMATION: Synthetic peptide

<400> SEQUENCE: 54

Ala Ile Thr Tyr Ser Gly Ser Thr Tyr Tyr Ser Pro Ser Leu Lys Ser
1               5                   10                  15

<210> SEQ ID NO 55
<211> LENGTH: 15
<212> TYPE: PRT
<213> ORGANISM: Artificial
<220> FEATURE:
<223> OTHER INFORMATION: Synthetic peptide

<400> SEQUENCE: 55

Glu Gly Ser Ser Ser Thr Gly Val Ser Arg Tyr Ser Phe Gly Ser
1               5                   10                  15

<210> SEQ ID NO 56
<211> LENGTH: 7
<212> TYPE: PRT
<213> ORGANISM: Artificial
<220> FEATURE:
<223> OTHER INFORMATION: Synthetic peptide

<400> SEQUENCE: 56

Thr Asn Arg Tyr Leu Trp Thr
1               5

<210> SEQ ID NO 57
<211> LENGTH: 16
<212> TYPE: PRT
<213> ORGANISM: Artificial
<220> FEATURE:
<223> OTHER INFORMATION: Synthetic peptide

<400> SEQUENCE: 57

```
Ala Ile Ala Tyr Ser Gly Arg Thr Tyr Tyr Ser Pro Ser Leu Lys Ser
1               5                   10                  15

<210> SEQ ID NO 58
<211> LENGTH: 8
<212> TYPE: PRT
<213> ORGANISM: Artificial
<220> FEATURE:
<223> OTHER INFORMATION: Synthetic peptide

<400> SEQUENCE: 58

Phe Thr Gly Trp Gly Gly Tyr Tyr
1               5

<210> SEQ ID NO 59
<211> LENGTH: 17
<212> TYPE: PRT
<213> ORGANISM: Artificial
<220> FEATURE:
<223> OTHER INFORMATION: Synthetic peptide

<400> SEQUENCE: 59

Thr Ile Asn Ser Gly Gly Ser Thr Ser Tyr Ala Asp Ser Val Lys
1               5                   10                  15

Gly

<210> SEQ ID NO 60
<211> LENGTH: 13
<212> TYPE: PRT
<213> ORGANISM: Artificial
<220> FEATURE:
<223> OTHER INFORMATION: Synthetic peptide

<400> SEQUENCE: 60

Arg Ser Leu Tyr Tyr Thr Arg Val Pro Met Tyr Asp Tyr
1               5                   10

<210> SEQ ID NO 61
<211> LENGTH: 5
<212> TYPE: PRT
<213> ORGANISM: Artificial
<220> FEATURE:
<223> OTHER INFORMATION: Synthetic peptide

<400> SEQUENCE: 61

Met Tyr Tyr Ile Asp
1               5

<210> SEQ ID NO 62
<211> LENGTH: 17
<212> TYPE: PRT
<213> ORGANISM: Artificial
<220> FEATURE:
<223> OTHER INFORMATION: Synthetic peptide

<400> SEQUENCE: 62

Arg Ile Asp Pro Glu Asp Gly Gly Thr Lys Tyr Ala Gln Lys Phe Gln
1               5                   10                  15

Gly

<210> SEQ ID NO 63
<211> LENGTH: 16
<212> TYPE: PRT
<213> ORGANISM: Artificial
<220> FEATURE:
```

<223> OTHER INFORMATION: Synthetic peptide

<400> SEQUENCE: 63

Ile Pro Asn Gly Gly Ser Tyr Tyr Tyr Thr Pro Tyr Asp Tyr Asp Tyr
1               5                   10                  15

<210> SEQ ID NO 64
<211> LENGTH: 17
<212> TYPE: PRT
<213> ORGANISM: Artificial
<220> FEATURE:
<223> OTHER INFORMATION: Synthetic peptide

<400> SEQUENCE: 64

Ser Ile Ser Ala Gly Gly Gly Thr Ser Tyr Tyr Ala Asp Ser Val Lys
1               5                   10                  15
Gly

<210> SEQ ID NO 65
<211> LENGTH: 12
<212> TYPE: PRT
<213> ORGANISM: Artificial
<220> FEATURE:
<223> OTHER INFORMATION: Synthetic peptide

<400> SEQUENCE: 65

Lys Arg Gln Asn Phe Trp Ser Glu Gly Tyr Asp Ser
1               5                   10

<210> SEQ ID NO 66
<211> LENGTH: 16
<212> TYPE: PRT
<213> ORGANISM: Artificial
<220> FEATURE:
<223> OTHER INFORMATION: Synthetic peptide

<400> SEQUENCE: 66

Arg Ile Thr Ser Gly Gly Gly Ser Thr Tyr Ala Asp Ser Val Lys Gly
1               5                   10                  15

<210> SEQ ID NO 67
<211> LENGTH: 12
<212> TYPE: PRT
<213> ORGANISM: Artificial
<220> FEATURE:
<223> OTHER INFORMATION: Synthetic peptide

<400> SEQUENCE: 67

Gly Gln Tyr Ser Asp Gly Tyr Tyr Pro Tyr Asp Tyr
1               5                   10

<210> SEQ ID NO 68
<211> LENGTH: 17
<212> TYPE: PRT
<213> ORGANISM: Artificial
<220> FEATURE:
<223> OTHER INFORMATION: Synthetic peptide

<400> SEQUENCE: 68

Thr Ile Ser Ala Gly Gly Gly Arg Thr Tyr Tyr Ala Asp Ser Val Lys
1               5                   10                  15
Gly

<210> SEQ ID NO 69
<211> LENGTH: 5

```
<212> TYPE: PRT
<213> ORGANISM: Artificial
<220> FEATURE:
<223> OTHER INFORMATION: Synthetic peptide

<400> SEQUENCE: 69

Ile Val Leu Asp Ser
1               5

<210> SEQ ID NO 70
<211> LENGTH: 5
<212> TYPE: PRT
<213> ORGANISM: Artificial
<220> FEATURE:
<223> OTHER INFORMATION: Synthetic peptide

<400> SEQUENCE: 70

Asp Tyr Thr Met Ser
1               5

<210> SEQ ID NO 71
<211> LENGTH: 5
<212> TYPE: PRT
<213> ORGANISM: Artificial
<220> FEATURE:
<223> OTHER INFORMATION: Synthetic peptide

<400> SEQUENCE: 71

Asp Tyr Thr Met Ser
1               5

<210> SEQ ID NO 72
<211> LENGTH: 17
<212> TYPE: PRT
<213> ORGANISM: Artificial
<220> FEATURE:
<223> OTHER INFORMATION: Synthetic peptide

<400> SEQUENCE: 72

Gly Ile Ser Gly Asn Gly Gly Arg Thr Asp Tyr Val Glu Pro Ile Glu
1               5                   10                  15

Gly

<210> SEQ ID NO 73
<211> LENGTH: 8
<212> TYPE: PRT
<213> ORGANISM: Artificial
<220> FEATURE:
<223> OTHER INFORMATION: Synthetic peptide

<400> SEQUENCE: 73

Thr Ser Pro Gln Ser Leu Asp Tyr
1               5

<210> SEQ ID NO 74
<211> LENGTH: 5
<212> TYPE: PRT
<213> ORGANISM: Artificial
<220> FEATURE:
<223> OTHER INFORMATION: Synthetic peptide

<400> SEQUENCE: 74

Val Val Ile Asp Tyr
1               5

<210> SEQ ID NO 75
```

```
<211> LENGTH: 5
<212> TYPE: PRT
<213> ORGANISM: Artificial
<220> FEATURE:
<223> OTHER INFORMATION: Synthetic peptide

<400> SEQUENCE: 75

Ser Tyr Ser Met Ser
1               5

<210> SEQ ID NO 76
<211> LENGTH: 17
<212> TYPE: PRT
<213> ORGANISM: Artificial
<220> FEATURE:
<223> OTHER INFORMATION: Synthetic peptide

<400> SEQUENCE: 76

Gly Ile Asn Thr Ser Gly Gly Thr Thr Ser Tyr Ala Ala Ser Val Lys
1               5                   10                  15

Gly

<210> SEQ ID NO 77
<211> LENGTH: 16
<212> TYPE: PRT
<213> ORGANISM: Artificial
<220> FEATURE:
<223> OTHER INFORMATION: Synthetic peptide

<400> SEQUENCE: 77

His Ile Arg Trp Ser Gly Ser Asn Tyr Tyr Tyr Gly Met Asp Tyr
1               5                   10                  15

<210> SEQ ID NO 78
<211> LENGTH: 11
<212> TYPE: PRT
<213> ORGANISM: Artificial
<220> FEATURE:
<223> OTHER INFORMATION: Synthetic peptide

<400> SEQUENCE: 78

Gly Gly Asp Asn Ile Gly Ser Lys Ser Ala Gln
1               5                   10

<210> SEQ ID NO 79
<211> LENGTH: 7
<212> TYPE: PRT
<213> ORGANISM: Artificial
<220> FEATURE:
<223> OTHER INFORMATION: Synthetic peptide

<400> SEQUENCE: 79

Ala Asp Ser Arg Arg Pro Ser
1               5

<210> SEQ ID NO 80
<211> LENGTH: 9
<212> TYPE: PRT
<213> ORGANISM: Artificial
<220> FEATURE:
<223> OTHER INFORMATION: Synthetic peptide

<400> SEQUENCE: 80

Gln Val Trp Asp Ser Ser Ala Ala Val
1               5
```

```
<210> SEQ ID NO 81
<211> LENGTH: 17
<212> TYPE: PRT
<213> ORGANISM: Artificial
<220> FEATURE:
<223> OTHER INFORMATION: Synthetic peptide

<400> SEQUENCE: 81

Lys Ser Ser Gln Ser Val Leu Asp Ser Ser Asn Gln Lys Asn Tyr Leu
1               5                   10                  15
Ala

<210> SEQ ID NO 82
<211> LENGTH: 7
<212> TYPE: PRT
<213> ORGANISM: Artificial
<220> FEATURE:
<223> OTHER INFORMATION: Synthetic peptide

<400> SEQUENCE: 82

Trp Ala Ser Thr Arg Glu Ser
1               5

<210> SEQ ID NO 83
<211> LENGTH: 9
<212> TYPE: PRT
<213> ORGANISM: Artificial
<220> FEATURE:
<223> OTHER INFORMATION: Synthetic peptide

<400> SEQUENCE: 83

Gln Gln Gly Tyr Ser Val Pro Val Thr
1               5

<210> SEQ ID NO 84
<211> LENGTH: 14
<212> TYPE: PRT
<213> ORGANISM: Artificial
<220> FEATURE:
<223> OTHER INFORMATION: Synthetic peptide

<400> SEQUENCE: 84

Thr Leu Gly Ser Gly Asn Ser Ile Gly Ala His Thr Ile Ser
1               5                   10

<210> SEQ ID NO 85
<211> LENGTH: 13
<212> TYPE: PRT
<213> ORGANISM: Artificial
<220> FEATURE:
<223> OTHER INFORMATION: Synthetic peptide

<400> SEQUENCE: 85

Tyr Tyr Ser Asp Ser Ser Asn His Gln Ala Ser Gly Val
1               5                   10

<210> SEQ ID NO 86
<211> LENGTH: 9
<212> TYPE: PRT
<213> ORGANISM: Artificial
<220> FEATURE:
<223> OTHER INFORMATION: Synthetic peptide

<400> SEQUENCE: 86

Ala Ala Gly Asp Gly Ser Gly Thr Val
1               5
```

```
<210> SEQ ID NO 87
<211> LENGTH: 17
<212> TYPE: PRT
<213> ORGANISM: Artificial
<220> FEATURE:
<223> OTHER INFORMATION: Synthetic peptide

<400> SEQUENCE: 87

Lys Ser Ser Gln Ser Val Leu Ser Ser Ser Asn Gln Lys Asn Tyr Leu
1               5                   10                  15

Ser

<210> SEQ ID NO 88
<211> LENGTH: 9
<212> TYPE: PRT
<213> ORGANISM: Artificial
<220> FEATURE:
<223> OTHER INFORMATION: Synthetic peptide

<400> SEQUENCE: 88

Gln Gln Gly Tyr Gly Ala Pro Leu Thr
1               5

<210> SEQ ID NO 89
<211> LENGTH: 14
<212> TYPE: PRT
<213> ORGANISM: Artificial
<220> FEATURE:
<223> OTHER INFORMATION: Synthetic peptide

<400> SEQUENCE: 89

Gly Leu Arg Ser Gly Ser Val Thr Thr Ser Asn Tyr Pro Gly
1               5                   10

<210> SEQ ID NO 90
<211> LENGTH: 7
<212> TYPE: PRT
<213> ORGANISM: Artificial
<220> FEATURE:
<223> OTHER INFORMATION: Synthetic peptide

<400> SEQUENCE: 90

Gly Ala Ser Ser Arg His Ser
1               5

<210> SEQ ID NO 91
<211> LENGTH: 10
<212> TYPE: PRT
<213> ORGANISM: Artificial
<220> FEATURE:
<223> OTHER INFORMATION: Synthetic peptide

<400> SEQUENCE: 91

Ala Leu Asn Lys Gly Thr Tyr Thr Asp Val
1               5                   10

<210> SEQ ID NO 92
<211> LENGTH: 16
<212> TYPE: PRT
<213> ORGANISM: Artificial
<220> FEATURE:
<223> OTHER INFORMATION: Synthetic peptide

<400> SEQUENCE: 92

Lys Ala Ser Gln Ser Leu Thr His Thr Asp Gly Thr Thr Ala Leu Tyr
1               5                   10                  15
```

<210> SEQ ID NO 93
<211> LENGTH: 7
<212> TYPE: PRT
<213> ORGANISM: Artificial
<220> FEATURE:
<223> OTHER INFORMATION: Synthetic peptide

<400> SEQUENCE: 93

Glu Val Ser Val Arg Ala Ser
1               5

<210> SEQ ID NO 94
<211> LENGTH: 8
<212> TYPE: PRT
<213> ORGANISM: Artificial
<220> FEATURE:
<223> OTHER INFORMATION: Synthetic peptide

<400> SEQUENCE: 94

Ala Gln Val Ala Tyr Tyr Pro Thr
1               5

<210> SEQ ID NO 95
<211> LENGTH: 14
<212> TYPE: PRT
<213> ORGANISM: Artificial
<220> FEATURE:
<223> OTHER INFORMATION: Synthetic peptide

<400> SEQUENCE: 95

Ala Gly Thr Ser Ser Asp Ile Gly Gly Tyr Asn Ser Val Ser
1               5                   10

<210> SEQ ID NO 96
<211> LENGTH: 7
<212> TYPE: PRT
<213> ORGANISM: Artificial
<220> FEATURE:
<223> OTHER INFORMATION: Synthetic peptide

<400> SEQUENCE: 96

Glu Val Asn Lys Arg Ala Ser
1               5

<210> SEQ ID NO 97
<211> LENGTH: 10
<212> TYPE: PRT
<213> ORGANISM: Artificial
<220> FEATURE:
<223> OTHER INFORMATION: Synthetic peptide

<400> SEQUENCE: 97

Ala Ser Tyr Arg Ser Ala Asn Asn Val Val
1               5                   10

<210> SEQ ID NO 98
<211> LENGTH: 14
<212> TYPE: PRT
<213> ORGANISM: Artificial
<220> FEATURE:
<223> OTHER INFORMATION: Synthetic peptide

<400> SEQUENCE: 98

Gly Leu Ser Ser Gly Ser Val Thr Thr Asn Asn Tyr Pro Gly
1               5                   10

```
<210> SEQ ID NO 99
<211> LENGTH: 7
<212> TYPE: PRT
<213> ORGANISM: Artificial
<220> FEATURE:
<223> OTHER INFORMATION: Synthetic peptide

<400> SEQUENCE: 99

Ser Thr Ser Ser Arg His Ser
1               5

<210> SEQ ID NO 100
<211> LENGTH: 10
<212> TYPE: PRT
<213> ORGANISM: Artificial
<220> FEATURE:
<223> OTHER INFORMATION: Synthetic peptide

<400> SEQUENCE: 100

Ala Leu Asp Ile Gly Ser Tyr Thr Ala Val
1               5                   10

<210> SEQ ID NO 101
<211> LENGTH: 14
<212> TYPE: PRT
<213> ORGANISM: Artificial
<220> FEATURE:
<223> OTHER INFORMATION: Synthetic peptide

<400> SEQUENCE: 101

Gly Leu Thr Ser Gly Ser Val Thr Ser Ser Asn Tyr Pro Gly
1               5                   10

<210> SEQ ID NO 102
<211> LENGTH: 7
<212> TYPE: PRT
<213> ORGANISM: Artificial
<220> FEATURE:
<223> OTHER INFORMATION: Synthetic peptide

<400> SEQUENCE: 102

Asn Thr Asn Ser Arg His Pro
1               5

<210> SEQ ID NO 103
<211> LENGTH: 10
<212> TYPE: PRT
<213> ORGANISM: Artificial
<220> FEATURE:
<223> OTHER INFORMATION: Synthetic peptide

<400> SEQUENCE: 103

Ala Leu His Lys Gly Ser Tyr Thr Ala Val
1               5                   10

<210> SEQ ID NO 104
<211> LENGTH: 14
<212> TYPE: PRT
<213> ORGANISM: Artificial
<220> FEATURE:
<223> OTHER INFORMATION: Synthetic peptide

<400> SEQUENCE: 104

Val Gly Ser Ser Asp Val Gly Tyr Gly Asp Tyr Val Ser
1               5                   10
```

```
<210> SEQ ID NO 105
<211> LENGTH: 7
<212> TYPE: PRT
<213> ORGANISM: Artificial
<220> FEATURE:
<223> OTHER INFORMATION: Synthetic peptide

<400> SEQUENCE: 105

Asp Val Glu Lys Arg Ala Ser
1               5

<210> SEQ ID NO 106
<211> LENGTH: 10
<212> TYPE: PRT
<213> ORGANISM: Artificial
<220> FEATURE:
<223> OTHER INFORMATION: Synthetic peptide

<400> SEQUENCE: 106

Ala Ser Tyr Arg Ser Asp Ser Asn Phe Val
1               5                   10

<210> SEQ ID NO 107
<211> LENGTH: 11
<212> TYPE: PRT
<213> ORGANISM: Artificial
<220> FEATURE:
<223> OTHER INFORMATION: Synthetic peptide

<400> SEQUENCE: 107

Gln Ala Ser Gln Ser Ile Ser Ser Tyr Leu Ala
1               5                   10

<210> SEQ ID NO 108
<211> LENGTH: 7
<212> TYPE: PRT
<213> ORGANISM: Artificial
<220> FEATURE:
<223> OTHER INFORMATION: Synthetic peptide

<400> SEQUENCE: 108

Gly Ala Ser Arg Leu Glu Pro
1               5

<210> SEQ ID NO 109
<211> LENGTH: 9
<212> TYPE: PRT
<213> ORGANISM: Artificial
<220> FEATURE:
<223> OTHER INFORMATION: Synthetic peptide

<400> SEQUENCE: 109

Leu Gln Asp Tyr Ser Trp Pro Tyr Ser
1               5

<210> SEQ ID NO 110
<211> LENGTH: 16
<212> TYPE: PRT
<213> ORGANISM: Artificial
<220> FEATURE:
<223> OTHER INFORMATION: Synthetic peptide

<400> SEQUENCE: 110

Lys Ala Ser Gln Ser Leu Ile His Ile Asp Gly Lys Thr Tyr Leu Tyr
1               5                   10                  15

<210> SEQ ID NO 111
```

```
<211> LENGTH: 7
<212> TYPE: PRT
<213> ORGANISM: Artificial
<220> FEATURE:
<223> OTHER INFORMATION: Synthetic peptide

<400> SEQUENCE: 111

Gln Val Ser Asn His Glu Ser
1               5

<210> SEQ ID NO 112
<211> LENGTH: 8
<212> TYPE: PRT
<213> ORGANISM: Artificial
<220> FEATURE:
<223> OTHER INFORMATION: Synthetic peptide

<400> SEQUENCE: 112

Ala Gln Ala Thr Tyr Tyr Pro Ser
1               5

<210> SEQ ID NO 113
<211> LENGTH: 17
<212> TYPE: PRT
<213> ORGANISM: Artificial
<220> FEATURE:
<223> OTHER INFORMATION: Synthetic peptide

<400> SEQUENCE: 113

Lys Ser Ser Gln Ser Val Val Ser Gly Ser Asn Gln Lys Ser Tyr Leu
1               5                   10                  15

Asn

<210> SEQ ID NO 114
<211> LENGTH: 7
<212> TYPE: PRT
<213> ORGANISM: Artificial
<220> FEATURE:
<223> OTHER INFORMATION: Synthetic peptide

<400> SEQUENCE: 114

Tyr Ala Ser Thr Gln Glu Ser
1               5

<210> SEQ ID NO 115
<211> LENGTH: 9
<212> TYPE: PRT
<213> ORGANISM: Artificial
<220> FEATURE:
<223> OTHER INFORMATION: Synthetic peptide

<400> SEQUENCE: 115

Gln Gln Ala Tyr Ser Ala Pro Tyr Asn
1               5

<210> SEQ ID NO 116
<211> LENGTH: 16
<212> TYPE: PRT
<213> ORGANISM: Artificial
<220> FEATURE:
<223> OTHER INFORMATION: Synthetic peptide

<400> SEQUENCE: 116

Lys Ala Ser Gln Ser Leu Val His Thr Asp Gly Lys Thr Tyr Val Tyr
1               5                   10                  15
```

```
<210> SEQ ID NO 117
<211> LENGTH: 8
<212> TYPE: PRT
<213> ORGANISM: Artificial
<220> FEATURE:
<223> OTHER INFORMATION: Synthetic peptide

<400> SEQUENCE: 117

Ala Gln Ala Thr Tyr Tyr Pro Ser
1               5

<210> SEQ ID NO 118
<211> LENGTH: 13
<212> TYPE: PRT
<213> ORGANISM: Artificial
<220> FEATURE:
<223> OTHER INFORMATION: Synthetic peptide

<400> SEQUENCE: 118

Thr Gly Ser Asn Arg Asn Ile Gly Asn Asn Tyr Val Asn
1               5                   10

<210> SEQ ID NO 119
<211> LENGTH: 7
<212> TYPE: PRT
<213> ORGANISM: Artificial
<220> FEATURE:
<223> OTHER INFORMATION: Synthetic peptide

<400> SEQUENCE: 119

Ser Asp Asn Leu Arg Thr Ser
1               5

<210> SEQ ID NO 120
<211> LENGTH: 11
<212> TYPE: PRT
<213> ORGANISM: Artificial
<220> FEATURE:
<223> OTHER INFORMATION: Synthetic peptide

<400> SEQUENCE: 120

Ser Ser Trp Asp Asp Ser Leu Ser Gly Ala Val
1               5                   10

<210> SEQ ID NO 121
<211> LENGTH: 117
<212> TYPE: PRT
<213> ORGANISM: Artificial
<220> FEATURE:
<223> OTHER INFORMATION: Synthetic peptide

<400> SEQUENCE: 121

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ile Asn Tyr
            20                  25                  30

Gly Met His Trp Val Arg Gln Ala Pro Gly Lys Gly Leu Glu Trp Val
        35                  40                  45

Ser Ala Val Asn Ser Gly Gly Ala Ser Thr Asp Tyr Ala Asp Ser Val
    50                  55                  60

Lys Gly Arg Phe Thr Ile Ser Arg Asp Asp Ala Lys Asn Thr Leu Tyr
65                  70                  75                  80

Leu Gln Met Asn Ser Leu Lys Ser Glu Asp Thr Ala Val Tyr Tyr Cys
                85                  90                  95
```

Val Lys Gly Trp Phe Tyr Gly Ile His Tyr Trp Gly Lys Gly Thr Leu
            100                 105                 110

Val Thr Val Ser Ser
        115

<210> SEQ ID NO 122
<211> LENGTH: 111
<212> TYPE: PRT
<213> ORGANISM: Artificial
<220> FEATURE:
<223> OTHER INFORMATION: Synthetic peptide

<400> SEQUENCE: 122

Gln Ala Val Leu Thr Gln Leu Pro Ser Val Ser Gly Ser Pro Gly Gln
1               5                   10                  15

Lys Ile Thr Ile Ser Cys Thr Gly Ser Ser Ser Asn Ile Gly Gly Gly
            20                  25                  30

Tyr Ser Val Gln Trp Phe Gln His Leu Pro Gly Thr Pro Pro Lys Leu
        35                  40                  45

Leu Ile Tyr Gly Asn Ser Asn Arg Ala Ser Gly Val Pro Asp Arg Phe
    50                  55                  60

Ser Gly Ser Lys Ser Gly Ser Ser Ala Ser Leu Thr Ile Thr Gly Leu
65                  70                  75                  80

Gln Ala Glu Asp Glu Ala Asp Tyr Tyr Cys Glu Ser Tyr Asp Asp Trp
                85                  90                  95

Leu Lys Gly Arg Gly Phe Gly Gly Gly Ser Lys Leu Thr Val Leu
            100                 105                 110

<210> SEQ ID NO 123
<211> LENGTH: 124
<212> TYPE: PRT
<213> ORGANISM: Artificial
<220> FEATURE:
<223> OTHER INFORMATION: Synthetic peptide

<400> SEQUENCE: 123

Gln Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Thr Thr Asn
            20                  25                  30

Tyr Tyr Ser Trp Ile Trp Ile Arg Gln Pro Pro Gly Lys Gly Leu Glu
        35                  40                  45

Trp Met Gly Ala Ser Val Tyr Ser Gly Ser Thr Phe Tyr Ser Pro Ser
    50                  55                  60

Leu Lys Asn Thr Ser Ile Ser Lys Asp Thr Ala Gln Asn Gln Phe Thr
65                  70                  75                  80

Leu Gln Leu Arg Ser Val Thr Pro Glu Asp Thr Ala Val Tyr Tyr Cys
                85                  90                  95

Ala Arg Ala Ser Ser Ala His Trp Gly Ser Ser Phe Ile Ser Ile Asp
            100                 105                 110

Tyr Trp Gly Gln Gly Thr Gln Val Thr Val Ser Ser
        115                 120

<210> SEQ ID NO 124
<211> LENGTH: 110
<212> TYPE: PRT
<213> ORGANISM: Artificial
<220> FEATURE:
<223> OTHER INFORMATION: Synthetic peptide -continued

<400> SEQUENCE: 124

Gln Ser Val Leu Thr Gln Pro Pro Ser Val Ser Gly Ser Pro Gly Lys
1               5                   10                  15

Thr Val Thr Ile Ser Cys Ala Gly Thr Ser Ser Asp Val Gly Tyr Gly
            20                  25                  30

Asn Tyr Val Ser Trp Tyr Gln Gln Leu Pro Gly Met Ala Pro Lys Leu
        35                  40                  45

Leu Ile Tyr Asp Val Asp Ile Arg Ala Ser Gly Ile Ala Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Thr Asn
                85                  90                  95

Asn Asn Ala Val Phe Gly Gly Gly Thr His Leu Thr Val Leu
            100                 105                 110

<210> SEQ ID NO 125
<211> LENGTH: 5
<212> TYPE: PRT
<213> ORGANISM: Artificial
<220> FEATURE:
<223> OTHER INFORMATION: Synthetic peptide

<400> SEQUENCE: 125

Asn Tyr Gly Met His
1               5

<210> SEQ ID NO 126
<211> LENGTH: 17
<212> TYPE: PRT
<213> ORGANISM: Artificial
<220> FEATURE:
<223> OTHER INFORMATION: Synthetic peptide

<400> SEQUENCE: 126

Ala Val Asn Ser Gly Gly Ala Ser Thr Asp Tyr Ala Asp Ser Val Lys
1               5                   10                  15

Gly

<210> SEQ ID NO 127
<211> LENGTH: 8
<212> TYPE: PRT
<213> ORGANISM: Artificial
<220> FEATURE:
<223> OTHER INFORMATION: Synthetic peptide

<400> SEQUENCE: 127

Gly Trp Phe Tyr Gly Ile His Tyr
1               5

<210> SEQ ID NO 128
<211> LENGTH: 7
<212> TYPE: PRT
<213> ORGANISM: Artificial
<220> FEATURE:
<223> OTHER INFORMATION: Synthetic peptide

<400> SEQUENCE: 128

Thr Asn Tyr Tyr Ser Trp Ile
1               5

<210> SEQ ID NO 129

```
<211> LENGTH: 16
<212> TYPE: PRT
<213> ORGANISM: Artificial
<220> FEATURE:
<223> OTHER INFORMATION: Synthetic peptide

<400> SEQUENCE: 129

Ala Ser Val Tyr Ser Gly Ser Thr Phe Tyr Ser Pro Ser Leu Lys Asn
1               5                   10                  15

<210> SEQ ID NO 130
<211> LENGTH: 15
<212> TYPE: PRT
<213> ORGANISM: Artificial
<220> FEATURE:
<223> OTHER INFORMATION: Synthetic peptide

<400> SEQUENCE: 130

Ala Ser Ser Ala His Trp Gly Ser Ser Phe Ile Ser Ile Asp Tyr
1               5                   10                  15

<210> SEQ ID NO 131
<211> LENGTH: 14
<212> TYPE: PRT
<213> ORGANISM: Artificial
<220> FEATURE:
<223> OTHER INFORMATION: Synthetic peptide

<400> SEQUENCE: 131

Thr Gly Ser Ser Ser Asn Ile Gly Gly Gly Tyr Ser Val Gln
1               5                   10

<210> SEQ ID NO 132
<211> LENGTH: 7
<212> TYPE: PRT
<213> ORGANISM: Artificial
<220> FEATURE:
<223> OTHER INFORMATION: Synthetic peptide

<400> SEQUENCE: 132

Gly Asn Ser Asn Arg Ala Ser
1               5

<210> SEQ ID NO 133
<211> LENGTH: 11
<212> TYPE: PRT
<213> ORGANISM: Artificial
<220> FEATURE:
<223> OTHER INFORMATION: Synthetic peptide

<400> SEQUENCE: 133

Glu Ser Tyr Asp Asp Trp Leu Lys Gly Arg Gly
1               5                   10

<210> SEQ ID NO 134
<211> LENGTH: 14
<212> TYPE: PRT
<213> ORGANISM: Artificial
<220> FEATURE:
<223> OTHER INFORMATION: Synthetic peptide

<400> SEQUENCE: 134

Ala Gly Thr Ser Ser Asp Val Gly Tyr Gly Asn Tyr Val Ser
1               5                   10

<210> SEQ ID NO 135
<211> LENGTH: 7
```

```
<212> TYPE: PRT
<213> ORGANISM: Artificial
<220> FEATURE:
<223> OTHER INFORMATION: Synthetic peptide

<400> SEQUENCE: 135

Asp Val Asp Ile Arg Ala Ser
1               5

<210> SEQ ID NO 136
<211> LENGTH: 10
<212> TYPE: PRT
<213> ORGANISM: Artificial
<220> FEATURE:
<223> OTHER INFORMATION: Synthetic peptide

<400> SEQUENCE: 136

Ala Ser Tyr Arg Thr Asn Asn Asn Ala Val
1               5                   10
```

CD70 COMBINATION THERAPY

RELATED APPLICATIONS

This application claims benefit of Great Britain Patent Application No. 1800649.4, filed Jan. 16, 2018, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on Jan. 16, 2019, is named 608245_AGX5-038_Sequence_Listing.txt and is 59,685 bytes in size.

FIELD OF THE INVENTION

The present invention relates to combination therapies for the treatment of malignancy, particularly myeloid malignancy such as acute myeloid leukemia (AML). The combination therapies may include an antibody molecule that binds to CD70 and at least one antibody molecule that binds to a leukemic stem cell (LSC) target. Preferred leukemic stem cell targets are TIM-3, IL1R3/IL1RAP and CD47. Alternatively or in addition, the combination therapies may include an antibody molecule that binds to CD70 and an agent that inhibits SIRPα signaling. The combination therapies may further include an additional anti-cancer agent, for example an agent used for the treatment of AML such as azacitidine or decitabine.

BACKGROUND TO THE INVENTION

In recent years, the development of new cancer treatments has focused on molecular targets, particularly proteins, implicated in cancer progression. The list of molecular targets involved in tumor growth, invasion and metastasis continues to expand, and includes proteins overexpressed by tumor cells as well as targets associated with systems supporting tumor growth such as the vasculature and immune system. The number of therapeutic or anti-cancer agents designed to interact with these molecular targets also continues to increase, and a large number of targeted cancer medicines are now approved for clinical use with many more in the developmental pipeline.

Immunotherapy is a particularly interesting approach to cancer treatment. This form of therapy seeks to harness the power of the body's own immune system to control tumor growth. The immune system is highly complex including a multitude of different cell types and in healthy individuals, these different cell populations are subject to tight control. During cancer development, tumors typically evolve ways to evade detection and elimination by the host immune system, for example by downregulation of natural killer (NK) cell activators, reduced expression of MHC class I proteins by the tumor cells, T cell anergy and/or the upregulation of immunosuppressive regulatory T cells (Tregs). Immunotherapy aims to reverse the immunosuppressive tumor environment thereby aiding the body in mounting an effective anti-tumor response.

CD70 has been identified as a molecular target of particular interest owing to its constitutive expression on many types of hematological malignancies and solid carcinomas (Junker et al. (2005) *J Urol.* 173:2150-3; Sloan et al. (2004) *Am J Pathol.* 164:315-23; Held-Feindt and Mentlein (2002) *Int J Cancer* 98:352-6; Hishima et al. (2000) *Am J Surg Pathol.* 24:742-6; Lens et al. (1999) *Br J Haematol.* 106: 491-503; Boursalian et al. (2009) *Adv Exp Med Biol.* 647: 108-119; Wajant H. (2016) *Expert Opin Ther Targets* 20(8): 959-973). CD70 is a type II transmembrane glycoprotein belonging to the tumor necrosis factor (TNF) superfamily, which mediates its effects through binding to its cognate cell surface receptor, CD27. Both CD70 and CD27 are expressed by multiple cell types of the immune system, and the CD70-CD27 signaling pathway has been implicated in the regulation of several different aspects of the immune response. This is reflected in the fact that CD70 overexpression occurs in various auto-immune diseases including rheumatoid and psoriatic arthritis and lupus (Boursalian et al. (2009) *Adv Exp Med Biol.* 647:108-119; Han et al. (2005) *Lupus* 14(8):598-606; Lee et al. (2007) *J Immunol.* 179(4): 2609-2615; Oelke et al. (2004) *Arthritis Rheum.* 50(6):1850-1860).

CD70 expression has been linked to poor prognosis for several cancers including B cell lymphoma, renal cell carcinoma and breast cancer (Bertrand et al. (2013) *Genes Chromosomes Cancer* 52(8):764-774; Jilaveanu et al. (2012) *Hum Pathol.* 43(9):1394-1399; Petrau et al. (2014) *J Cancer* 5(9):761-764). CD70 expression has also been found on metastatic tissue in a high percentage of cases indicating a key role for this molecule in cancer progression (Jacobs et al. (2015) *Oncotarget* 6(15):13462-13475). Constitutive expression of CD70 and its receptor CD27 on tumor cells of hematopoietic lineage has been linked to a role of the CD70-CD27 signaling axis in directly regulating tumor cell proliferation and survival (Goto et al. (2012) *Leuk Lymphoma* 53(8):1494-1500; Lens et al. (1999) *Br J Haematol.* 106(2); 491-503; Nilsson et al. (2005) *Exp Hematol.* 33(12): 1500-1507; van Doorn et al (2004) *Cancer Res.* 64(16): 5578-5586).

Upregulated CD70 expression on tumors, particularly solid tumors that do not co-express CD27, also contributes to immunosuppression in the tumor microenvironment in a variety of ways. For example, CD70 binding to CD27 on regulatory T cells has been shown to augment the frequency of Tregs, reduce tumor-specific T cell responses and promote tumor growth in mice (Claus et al. (2012) *Cancer Res.* 72(14):3664-3676). CD70-CD27 signaling can also dampen the immune response by tumor-induced apoptosis of T-lymphocytes, as demonstrated in renal cell carcinoma, glioma and glioblastoma cells (Chahlavi et al. (2005) *Cancer Res.* 65(12):5428-5438; Diegmann et al. (2006) *Neoplasia* 8(11): 933-938); Wischusen et al. (2002) *Cancer Res* 62(9):2592-2599). Finally, CD70 expression has also been linked to T cell exhaustion whereby the lymphocytes adopt a more differentiated phenotype and fail to kill the tumor cells (Wang et al. (2012) *Cancer Res* 72(23):6119-6129; Yang et al. (2014) *Leukemia* 28(9):1872-1884).

Given the importance of CD70 in cancer development, CD70 is an attractive target for anti-cancer therapy, and antibodies targeting this cell surface protein are in clinical development (Jacob et al. (2015) *Pharmacol Ther.* 155:1-10; Silence et al. (2014) *mAbs* 6(2):523-532).

SUMMARY OF INVENTION

The present invention is directed to combination therapies comprising antibody molecules that bind to CD70. In the combination therapies of the invention, an antibody molecule that binds to CD70 is combined with at least one additional agent directed to a different target so as to achieve more effective cancer treatment. The agents with which the CD70 antibody molecules may be combined include antibody molecules that bind to leukemic stem cell targets and/or agents that inhibit SIRPα signaling.

It has been found that anti-CD70 antibodies are effective for the treatment of myeloid malignancies, particularly acute myeloid leukemia (AML) and myelodysplastic syndrome (MDS). The present invention is based on the use of antibody molecules that bind CD70 in combination with additional agents that target malignant myeloid cells, particularly leukemic stem cells.

In a first aspect, the present invention provides a combination comprising an antibody molecule that binds to CD70 and at least one antibody molecule that binds to a leukemic stem cell target.

In certain embodiments, the leukemic stem cell target is selected from the group consisting of: TIM-3; Galectin-9; CD47; IL1RAP; LILRB2; CLL-1; CD123; CD33; SAIL; GPR56; CD44; E-selectin; CXCR4; CD25; CD32; PR1; WT1; ADGRE2; CCR1; TNFRSF1B and CD96. In preferred embodiments, the leukemic stem cell target is selected from TIM-3, Galectin-9, CD47, IL1RAP and LILRB2.

In certain embodiments, the antibody molecule that binds to CD70 is selected from: (i) an antibody molecule comprising a variable heavy chain domain (VH) and a variable light chain domain (VL) comprising the heavy chain CDRs (HCDR3, HCDR2 and HCDR1) and light chain CDRs (LCDR3, LCDR2 and LCDR1): HCDR3 having an amino acid sequence comprising or consisting of SEQ ID NO: 3; HCDR2 having an amino acid sequence comprising or consisting of SEQ ID NO: 2; HCDR1 having an amino acid sequence comprising or consisting of SEQ ID NO: 1; LCDR3 having an amino acid sequence comprising or consisting of SEQ ID NO: 7; LCDR2 having an amino acid sequence comprising or consisting of SEQ ID NO: 6; and LCDR1 having an amino acid sequence comprising or consisting of SEQ ID NO: 5; (ii) an antibody molecule comprising a VH domain comprising an amino acid sequence at least 70%, at least 80%, at least 90%, or at least 95% identical to SEQ ID NO:4 and a VL domain comprising an amino acid sequence at least 70%, at least 80%, at least 90%, or at least 95% identical to SEQ ID NO:8; or (iii) ARGX-110.

In certain embodiments, the combinations comprise, in addition to the antibody molecule that binds CD70, an antibody molecule that binds to a first leukemic stem cell target and an antibody molecule that binds to a second leukemic stem cell target, wherein the first and second leukemic stem cell targets are different. The first and/or second leukemic stem cell targets may be selected from the group consisting of: TIM-3; Galectin-9; CD47; IL1RAP; LILRB2; CLL-1; CD123; CD33; SAIL; GPR56; CD44; E-selectin; CXCR4; CD25; CD32; PR1; WT1; ADGRE2; CCR1; TNFRSF1B and CD96, preferably the group consisting of: TIM-3; Galectin-9; CD47; IL1RAP and LILRB2. In preferred embodiments, the first leukemic stem cell target is TIM-3 and the second leukemic stem cell target is CD47. In further preferred embodiments, the first leukemic stem cell target is TIM-3 and the second leukemic stem cell target is IL1RAP.

For combinations of the invention comprising an antibody molecule that binds TIM-3 or an antibody molecule that binds IL1RAP, in certain embodiments, this antibody molecule results in reduced NF-κB signaling; reduced Wnt/β-catenin signaling; reduced stemness of AML cells; or a combination thereof. Alternatively or in addition, the antibody molecule that binds TIM-3 may inhibit the interaction of TIM-3 with one or more TIM-3 interacting proteins, optionally TIM-3 interacting proteins selected from: CEACAM-1; HMGB-1; phosphatidylserine; Galectin-9; LILRB2; and combinations thereof.

In certain embodiments, the antibody molecule or antibody molecules that bind to LSC target(s) is/are camelid-derived. For example, the antibody molecules may be selected from one or more immune libraries obtained by a method comprising the step of immunizing a camelid, preferably a llama, with the leukemic stem cell target(s). The antibody molecules may be derived from camelid by immunizing an animal of a camelid species with the LSC target protein or a polypeptide fragment thereof or by immunizing a camelid species with a mRNA or cDNA molecule expressing the LSC target protein or a polypeptide fragment thereof.

For combinations of the invention comprising an antibody molecule that binds CD47, in certain embodiments, the antibody molecule inhibits the interaction between CD47 on the leukemic stem cells and SIRPα on phagocytic cells. The antibody molecule that binds CD47 may alternatively or in addition increase phagocytosis of tumor cells.

In certain embodiments, the antibody molecules of the combination are independently selected from the group consisting of: an IgG antibody; an antibody light chain variable domain (VL); an antibody heavy chain variable domain (VH); a single chain antibody (scFv); a F(ab')2 fragment; a Fab fragment; an Fd fragment; an Fv fragment; a one-armed (monovalent) antibody; diabodies, triabodies, tetrabodies or any antigen-binding molecule formed by combination, assembly or conjugation of such antigen binding fragments.

Regarding the formulation of the combination, in certain embodiments, the antibody molecules of the combination are combined in a single antibody format, for example as a multispecific antibody, preferably a bispecific antibody. Alternatively, the antibody molecules may be separate but co-formulated in a single composition. For antibody molecules co-formulated as a single composition, the ratio of the different antibody molecules may be 1:1. Alternatively, the antibody molecules may be present in different relative amounts. For example, for embodiments of the invention in which the combination comprises a first antibody molecule that binds to CD70 and a second antibody molecule that binds to a LSC target, the ratio of first antibody molecule to second antibody molecule may be 1:2, 1:3, 1:4, 1:5, 2:1, 3:1, 4:1, 5:1 etc. In alternative embodiments, the antibody molecules are provided separately.

The antibody molecules of the combinations may possess one or more effector functions. In certain embodiments, at least one of the antibody molecules: blocks its target's function completely or partially; and/or has antibody-dependent cellular cytotoxicity (ADCC) activity; and/or comprises a defucosylated antibody domain; and/or has complement-dependent cytotoxicity (CDC) activity; and/or has antibody-dependent cellular phagocytosis (ADCP) activity.

The combinations of the invention may comprise one or more additional therapeutic agents, for example one or more additional anti-cancer agents. In certain embodiments, the combination comprises an agent that inhibits SIRPα signaling. The agent that inhibits SIRPα signaling may be an antibody molecule that binds to SIRPα and inhibits the interaction between CD47 and SIRPα or alternatively may be a SIRPα-antibody molecule fusion protein, for example a SIRPα-Fc fusion. In certain embodiments, the SIRPα-antibody molecule fusion protein comprises at least one of the antibody molecules of the combination. In particular embodiments, the SIRPα-antibody molecule fusion protein comprises the antibody molecule of the combination that binds CD70.

In a further aspect, the present invention provides a combination comprising an antibody molecule that binds to CD70 and an agent that inhibits SIRPα signaling.

The agent that inhibits SIRPα signaling may be selected from: (i) an antibody molecule that binds CD47 and inhibits the interaction between CD47 and SIRPα; (ii) an antibody molecule that binds SIRPα and inhibits the interaction between CD47 and SIRPα; (iii) a SIRPα-antibody molecule fusion protein, optionally a SIRPα-Fc fusion protein. In particular embodiments, the antibody molecule that binds to CD70 and the agent that inhibits SIRPα signaling are combined into a single molecule, for example a SIRPα-antibody molecule fusion protein wherein the antibody molecule comprises or consists of the antibody molecule that binds CD70. In particular embodiments, the combinations of the second aspect of the invention comprise at least one SIRPα V-like domain covalently linked to the antibody molecule that binds to CD70. The linkage between the SIRPα V-like domain and the antibody molecule that binds to CD70 may be mediated via a linker.

In all aspects of the invention, in certain embodiments, the combination comprises at least one additional anti-cancer agent, for example at least one agent for treating myeloid malignancy. In certain embodiments, the combinations herein comprise an additional agent for treating AML. In preferred embodiments, the combinations comprise a hypomethylating agent, preferably azacitidine. Alternatively or in addition, the combination may comprise a PD-1 inhibitor and/or a PD-L1 inhibitor.

In a further aspect, the present invention provides combinations according to the first and second aspects of the invention for use in the treatment of malignancy in a human subject. The present invention also provides a method for treating a malignancy in a human subject, said method comprising administering to the subject any of the combinations according to the first or second aspects of the invention.

The present invention also provides an antibody molecule that binds to CD70 for use in the treatment of a malignancy in a human subject, wherein the antibody molecule is administered in combination with an antibody molecule that binds to a leukemic stem cell target. The present invention also provides an antibody molecule that binds to a leukemic stem cell target for use in the treatment of a malignancy in a human subject, wherein the antibody molecule is administered in combination with an antibody molecule that binds to CD70.

The present invention also provides an antibody molecule that binds to CD70 for use in the treatment of malignancy in a human subject, wherein the antibody molecule is administered in combination with an agent that inhibits SIRPα signaling. The present invention also provides an agent that inhibits SIRPα signaling for use in the treatment of malignancy in a human subject, wherein the agent is administered in combination with an antibody molecule that binds CD70.

Regarding the malignancies to be treated using combinations of the invention, said malignancies may be (i) malignancies comprising the production of cancer progenitor or stem cells expressing CD70, CD27 or both; (ii) malignancies comprising the production of cancer progenitor or stem cells expressing the LSC target to which at least one of the antibody molecules of the combination binds; (iii) myeloid malignancies; (iv) newly diagnosed myeloid malignancies; (v) relapsed or refractory myeloid malignancies; (vi) myeloid malignancies selected from: acute myeloid leukemia (AML), myelodysplastic syndromes (MDS), myeloproliferative neoplasms (MPN), chronic myeloid leukemia (CML), and chronic myelomonocytic leukemia (CMML). In a particularly preferred embodiment, the combinations of the invention are for the treatment of acute myeloid leukemia (AML).

In certain embodiments, the methods further comprise monitoring of the patient's blast count. The patient's peripheral blood and/or bone marrow count may be reduced, for example reduced to less than 25%, for example reduced to 5%, for example reduced to less than 5%, for example reduced to undetectable levels. In certain embodiments, the bone marrow blast count is reduced to between 5% and 25% and the bone marrow blast percentage is reduced by more than 50% as compared to pretreatment.

In certain embodiments, the methods induce at least a partial response. In certain embodiments, the methods induce a complete response, optionally with platelet recovery and/or neutrophil recovery. The methods may induce transfusion independence of red blood cells or platelets, or both, for 8 weeks or longer, 10 weeks or longer, or 12 weeks or longer. In certain embodiments, the methods reduce the mortality rate after a 30-day period or after a 60-day period.

In certain embodiments, the methods increase survival. For example, the methods may increase survival relative to the standard of care agent or agents used to treat the particular myeloid malignancy being treated with the combination. The methods may induce a minimal residual disease status that is negative.

In certain embodiments, the methods further comprise a step of subjecting the subject to a bone marrow transplantation. Alternatively or in addition, the methods may further comprise a step of administering one or more additional anti-cancer agents. The one or more additional anti-cancer agents may be selected from any agents suitable for the treatment of myeloid malignancies, preferably AML. Preferred agents may be selected from Venetoclax; Vyxeos; Idhifa (Enasidenib); and Rydapt (midostaurin).

BRIEF DESCRIPTION OF THE DRAWINGS

FIG. 5A shows CDC measured using MV4-11 AML cells; FIG. 5B shows CDC measured using NOMO-1 AML cells.

FIG. 6A shows CDC measured using MV4-11 AML cells; FIG. 6B shows CDC measured using NOMO-1 AML cells.

DETAILED DESCRIPTION

A. Definitions

Figure 1:
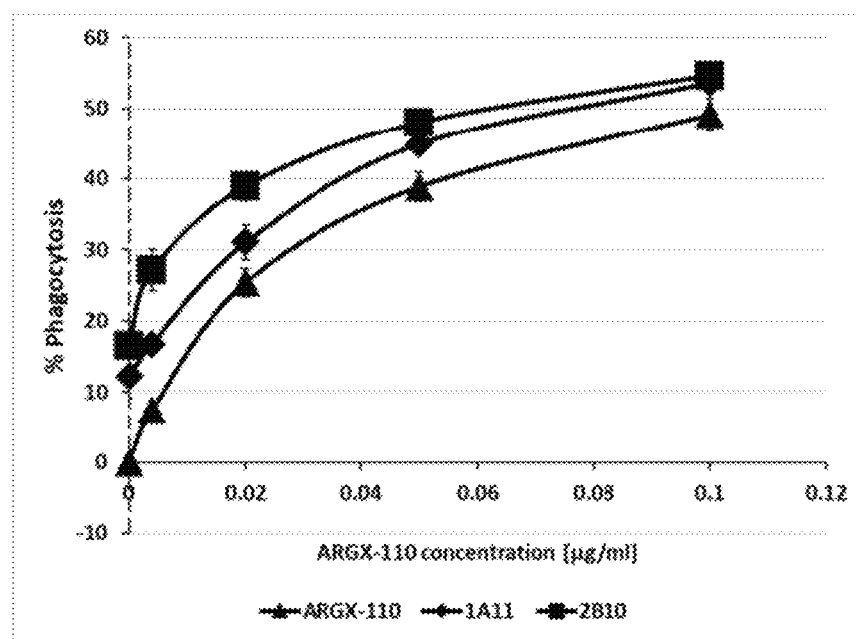
FIG. 1 shows the combined efficacy of an anti-CD70 antibody (ARGX-110) and anti-TIM-3 antibodies (1A11 and 2B10) in mediating antibody-dependent cellular phagocytosis (ADCP) against BDCM cell line.

Unless defined otherwise, all technical and scientific terms used herein have the same meaning as is commonly understood by one skilled in the art in the technical field of the invention.

"Combination therapy"—As used herein, the term "combination therapy" refers to a treatment in which a subject, for example a human subject, is given two or more therapeutic agents. The "combinations" described herein are for use in combination therapy. The two or more therapeutic agents are typically administered so as to treat a single disease, herein a malignancy. In certain embodiments, the combination therapies of the present invention utilize antibody molecules binding to different targets, specifically CD70 and a leukemic stem cell target, for example TIM-3, CD47 or IL1RAP. As described elsewhere herein, the antibody molecules included in the combination therapies may be comprised within a single antibody (for example, a multispecific antibody), may be co-formulated or may be provided separately, for example as separate compositions, for administration to a subject or patient in need thereof. In certain embodiments, the combination therapies of the present invention utilize an antibody molecule that binds to CD70 in combination with at least one agent that inhibits SIRPα signaling. The antibody molecule that binds to CD70 may be combined with the agent that inhibits SIRPα signaling into a single SIRPα-antibody molecule fusion protein. Alternatively, the antibody molecule that binds to CD70 and the agent that inhibits SIRPα signaling may be provided separately, for example as separate compositions, for administration to a subject or patient in need thereof.

"Antibody molecule"—As used herein, the term "antibody molecule" is intended to encompass full-length antibodies and antigen binding fragments thereof, including variants such as modified antibodies, humanized antibodies, germlined antibodies and antigen binding fragments thereof. The term "antibody" typically refers to an immunoglobulin polypeptide having a combination of two heavy and two light chains wherein the polypeptide has significant specific immunoreactive activity to an antigen of interest (herein CD70 or a leukemic stem cell target, for example TIM-3, CD47, IL1RAP). For antibodies of the IgG class, the antibodies comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region. The light chains of an antibody are classified as either kappa or lambda (κ,λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Those skilled in the art will appreciate that heavy chains are classified as gamma, mu, alpha, delta, or epsilon (γ, μ, α, ε), with some subclasses among them (e.g., γ1-γ4). It is the nature of this chain that determines the "class" of the antibody as IgG, IgM, IgA, IgD or IgE, respectively. The immunoglobulin subclasses (isotypes) e.g., IgG1, IgG2, IgG3, IgG4, IgA1, etc. are well characterized and are known to confer functional specialization. The term "antibody molecule" as used herein encompasses full-length antibodies or antigen binding fragments thereof from any class or subclass of antibody.

With respect to antigen binding fragments encompassed within the generic term "antibody molecule", these fragments are parts or portions of a full-length antibody or antibody chain comprising fewer amino acid residues than an intact or complete antibody whilst retaining antigen binding activity. The term "antibody molecule" as used herein is intended to encompass antigen binding fragments selected from: an antibody light chain variable domain (VL); an antibody heavy chain variable domain (VH); a single chain antibody (scFv); a F(ab')2 fragment; a Fab fragment; an Fd fragment; an Fv fragment; a one-armed (monovalent) antibody; diabodies, triabodies, tetrabodies or any antigen-binding molecule formed by combination, assembly or conjugation of such antigen binding fragments. The term "antibody molecule" as used herein is further intended to encompass antibody fragments selected from the group consisting of: unibodies; domain antibodies; and nanobodies. Fragments can be obtained, for example, via chemical or enzymatic treatment of an intact or complete antibody or antibody chain or by recombinant means.

"Specificity" and "Multispecific antibodies"—The antibody molecules for use in the combination therapies described herein bind to particular target antigens. It is preferred that the antibody molecules "specifically bind" to their target antigen, wherein the term "specifically bind" refers to the ability of any antibody molecule to preferentially immunoreact with a given target e.g. CD70, TIM-3, CD47, IL1RAP, LILRB2. The antibody molecules of the present combinations and methods may be monospecific and contain one or more binding sites which specifically bind a particular target. The antibody molecules of the present combinations and methods may be incorporated into "multispecific antibody" formats, for example bispecific antibodies, wherein the multispecific antibody binds to two or more target antigens. For example, in one embodiment, the combination of the present invention comprises a bispecific antibody comprising a first antibody molecule specifically binding to CD70 and a second antibody molecule specifically binding to TIM-3. In an alternative embodiment, the combination of the present invention comprises a bispecific antibody comprising a first antibody molecule specifically binding to CD70 and a second antibody molecule specifically binding to CD47. In a further alternative embodiment, the combination of the present invention comprises a bispecific antibody comprising a first antibody molecule specifically binding to CD70 and a second antibody molecule specifically binding to IL1RAP. In order to achieve multiple specificities, "multispecific antibodies" are typically engineered to include different combinations or pairings of heavy and light chain polypeptides with different VH-VL pairs. Multispecific, notably bispecific, antibodies may be engineered so as to adopt the overall conformation of a native antibody, for example a Y-shaped antibody having Fab arms of different specificities conjugated to an Fc region. Alternatively multispecific antibodies, for example bispecific antibodies, may be engineered so as to adopt a non-native conformation, for example wherein the variable domains or variable domain pairs having different specificities are positioned at opposite ends of the Fc region.

The bispecific or multispecific antibodies may have a native IgG structure with two Fab arms having binding specificity for the first target, and one or more additional antigen-binding domains positioned at the C terminus of the Fc domain having binding specificity for the second target. Alternatively, the bispecific or multispecific antibodies may have a native IgG structure with two Fab arms having binding specificity for the first target and one or more scFv fragments having binding specificity for the second target positioned at the C-terminus of the Fc domain. The bispecific or multispecific antibodies may be asymmetric IgG antibodies, such that one Fab region is replaced by a different antigen-binding domain, for example a VHH domain. In these asymmetric antibodies, the Fab region or fragment may bind to CD70 and the VHH domain may bind to the LSC target or vice versa.

"Modified antibody"—As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. scFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain portion lacking a CH2 domain and comprising a binding domain of a polypeptide comprising the binding portion of one member of a receptor ligand pair.

"Humanizing substitutions"—As used herein, the term "humanizing substitutions" refers to amino acid substitutions in which the amino acid residue present at a particular position in the VH or VL domain of an antibody is replaced with an amino acid residue which occurs at an equivalent position in a reference human VH or VL domain. The reference human VH or VL domain may be a VH or VL domain encoded by the human germline. Humanizing substitutions may be made in the framework regions and/or the CDRs of the antibodies, defined herein.

"Humanized variants"—As used herein the term "humanized variant" or "humanized antibody" refers to a variant antibody which contains one or more "humanizing substitutions" compared to a reference antibody, wherein a portion of the reference antibody (e.g. the VH domain and/or the VL domain or parts thereof containing at least one CDR) has an amino acid derived from a non-human species, and the "humanizing substitutions" occur within the amino acid sequence derived from a non-human species.

"Germlined variants"—The term "germlined variant" or "germlined antibody" is used herein to refer specifically to "humanized variants" in which the "humanizing substitutions" result in replacement of one or more amino acid residues present at (a) particular position(s) in the VH or VL domain of an antibody with an amino acid residue which occurs at an equivalent position in a reference human VH or VL domain encoded by the human germline. It is typical that for any given "germlined variant", the replacement amino acid residues substituted into the germlined variant are taken exclusively, or predominantly, from a single human germline-encoded VH or VL domain. The terms "humanized variant" and "germlined variant" are often used interchangeably. Introduction of one or more "humanizing substitutions" into a camelid-derived (e.g. llama-derived) VH or VL domain results in production of a "humanized variant" of the camelid (llama-derived) VH or VL domain. If the amino acid residues substituted in are derived predominantly or exclusively from a single human germline-encoded VH or VL domain sequence, then the result may be a "human germlined variant" of the camelid (llama)-derived VH or VL domain.

"CD70"—As used herein, the terms "CD70" or "CD70 protein" or "CD70 antigen" are used interchangeably and refer to a member of the TNF ligand family which is a ligand for TNFRSF7/CD27. CD70 is also known as CD27L or TNFSF7. The terms "human CD70 protein" or "human CD70 antigen" or "human CD70" are used interchangeably to refer specifically to the human homolog, including the native human CD70 protein naturally expressed in the human body and/or on the surface of cultured human cell lines, as well as recombinant forms and fragments thereof. Specific examples of human CD70 include the polypeptide having the amino acid sequence shown under NCBI Reference Sequence Accession No. NP_001243, or the extracellular domain thereof.

"Leukemic stem cell target"—As used herein, the term "leukemic stem cell target" refers to an antigen expressed by leukemic stem cells. Leukemic stem cells or "LSCs" are a low-frequency subpopulation of leukemia cells that possess stem cell properties distinct from the bulk leukemia cells, including self-renewal capacity; see for example Wang et al. (2017) Molecular Cancer 16:2, incorporated herein by reference. LSCs typically occur with a frequency in the range of 1 in 10,000 to 1 in 1 million as a proportion of primary blast cells in acute myeloid leukemia—AML (Pollyea and Jordan (2017) Blood 129:1627-1635, incorporated herein by reference). LSCs, if transplanted into an immune-deficient recipient are capable of initiating leukemic disease and since these leukemic stem cells appear to drive cancer growth, they represent an attractive target for novel therapeutic agents. LSCs produce a range of molecules, including cell surface antigens, which serve as markers of LSCs. These markers may, in some cases, allow LSCs to be distinguished from bulk leukemia cells; see for example Hanekamp et al. (2017) Int. J Hematol. 105:549-557, incorporated herein by reference. The term "leukemic stem cell target" as used herein refers to LSC markers, particularly the cell-surface population thereof.

"TIM-3"—As used herein, the term "TIM-3" or "TIMD-3" refers to "T cell immunoglobulin and mucin-domain containing-3" protein. TIM-3 is also referred to as Hepatitis A virus cellular receptor 2 (HAVCR2). TIM-3 is a member of the immunoglobulin superfamily having a transmembrane structure comprising an extracellular domain consisting of a membrane-distal N-terminal immunoglobulin domain and a membrane-proximal mucin domain containing potential sites for O-linked glycosylation. Different polymorphic variants of the TIM-3 protein are known. See for example the 301 and 272 amino acid human TIM-3 variants: uniprot.org/uniprot/Q8TDQ0; and uniprot.org/uniprot/E5RHN3. The term "TIM-3" as used herein is intended to cover all TIM-3 polymorphic variants encoded by transcripts from the TIM-3/HAVCR2 genomic locus which result in cell surface-expressed TIM-3.

"Galectin-9"—As used herein, the term "Galectin-9" refers to the extracellular membrane associated protein that serves as a TIM-3 ligand or binding partner. Galectin-9 is a soluble protein containing two tandemly linked carbohydrate recognition domains, which specifically recognize the structure of N-linked sugar chains in the TIM-3 immunoglobulin domain. The human homolog of Galectin-9 consists of 355 amino acid residues as represented by GenBank Accession BAB83625.

"CD47"—As used herein, the term "CD47" refers to the cell surface antigen CD47, which is a transmembrane protein ubiquitously expressed on a variety of normal cells and tumor cells. CD47 is a ligand for the immunoglobulin superfamily receptor SIRPα. CD47 is also referred to as "Antigenic surface determinant protein OA3", "Integrin-associated protein (IAP)" and "Protein MER6". The human homolog of CD47 encoded by the CD47 genomic locus is 323 amino acids in length (uniprot.org/uniprot/Q08722). The term CD47 as used herein is intended to encompass all polymorphic variants of the CD47 protein.

"SIRPα"—As used herein, the term "SIRPα" refers to "Signal-regulatory protein alpha", which is also known as SHP substrate 1 (SHPS-1), Brain Ig-like molecule with tyrosine-based activation motifs (Bit), CD172 antigen-like family member A, Inhibitory receptor SHPS-1, Macrophage fusion receptor, MyD-1 antigen, SIRPα1, SIRPα2, SIRPα3, p84, and CD172a. SIRPα is a member of the immunoglobulin superfamily and is a transmembrane protein expressed on phagocytic cells, including macrophages and dendritic cells. It is a receptor for CD47. The human homolog of SIRPα encoded by the SIRPA genomic locus is 504 amino acids in length (uniprot.org/uniprot/P78324). The term SIRPα as used herein is intended to encompass all polymorphic variants of the SIRPα protein.

"SIRPα antibody molecule fusion protein"—As used herein, the term "SIRPα antibody molecule fusion protein" is intended to mean a fusion protein comprising the SIRPα protein or a fragment thereof and an antibody molecule. The antibody molecule may be a full-length antibody molecule as defined elsewhere herein, for example a full-length IgG antibody. Alternatively, the antibody molecule may be an antigen binding fragment of an antibody as defined elsewhere herein. The SIRPα protein or fragment thereof may be fused to the antibody molecule at any suitable location on the antibody molecule. For example, the SIRPα protein or fragment thereof may be fused to the N-terminus or C-terminus of the heavy chain or light chain of the antibody molecule. In certain embodiments, the SIRPα antibody molecule fusion protein will not include the full-length SIRPα protein but will include a fragment thereof, particularly a fragment capable of binding to CD47. For example, the SIRPα antibody molecule fusion protein may include one or more copies of the SIRPα immunoglobulin V-like domain, wherein the immunoglobulin V-like domain is defined by amino acid positions 32-137 of the 504 amino acid full-length human SIRPα protein. "IL1RAP"—As used herein, the term "IL1RAP" or "IL-1RAP" or "IL-1RAcP" or "IL-1RAcP" refers to "Interleukin 1 receptor accessory protein". IL1RAP is also known as "Interleukin 1 receptor 3" or "IL-1R3" or "IL1R3". IL1RAP is a co-receptor for type I interleukin 1 receptor (IL1R1) and is required for signaling mediated by the cytokine IL-1. It also serves as a co-receptor for IL1R4 and IL1R3 to mediate signaling via IL-33 and IL-36, respectively. IL-1, for example, mediates its effects downstream of the cell-surface IL-1 receptor complex (IL-1+IL1R1+IL1 RAP) via activation of different intracellular signaling pathways including the NF-κB pathway. The human homolog of IL1RAP encoded by the IL1RAP genomic locus is 570 amino acids in length (uniprot.org/uniprot/Q9NPH3).

"LILRB2"—As used herein, the term "LILRB2" refers to "Leukocyte immunoglobulin-like receptor subfamily B member 2". LILRB2 is also known as "Leukocyte immunoglobulin-like receptor 2" or "LIR-2", "CD85 antigen-like family member D" or "CD85d", "Immunoglobulin-like transcript 4" or "ILT-4", and "Monocyte/macrophage immunoglobulin-like receptor 10" or "MIR-10". LILRB2 is involved in the down-regulation of the immune response and the development of tolerance. The human homolog of LILRB2 encoded by the LILRB2 genomic locus is 598 amino acids in length (uniprot.org/uniprot/Q8N423).

"Myeloid malignancy"—As used herein, the term "myeloid malignancy" refers to any clonal disease of hematopoietic stem or progenitor cells. Myeloid malignancies or myeloid malignant diseases include chronic and acute conditions. Chronic conditions include myelodysplastic syndromes (MDS), myeloproliferative neoplasms (MPN) and chronic myelomonocytic leukemia (CMML), and acute conditions include acute myeloid leukemia (AML).

"Acute myeloid malignancy"—As used herein, "acute myeloid leukemia" or "AML" refers to hematopoietic neoplasms involving myeloid cells. AML is characterized by clonal proliferation of myeloid precursors with reduced differentiation capacity. AML patients exhibit an accumulation of blast cells in the bone marrow. "Blast cells", or simply "blasts", as used herein refers to clonal myeloid progenitor cells exhibiting disrupted differentiation potential. Blast cells typically also accumulate in the peripheral blood of AML patients. Typically AML is diagnosed if the patient exhibits 20% or more blast cells in the bone marrow or peripheral blood.

"Anti-cancer agent"—As used herein, an anti-cancer agent refers to any agent that is capable of preventing, inhibiting or treating cancer growth directly or indirectly. Such agents include chemotherapeutic agents, immunotherapeutic agents, anti-angiogenic agents, radionuclides, etc., many examples of which are known to those skilled in the art.

"Identity" or "Identical"—As used herein, the term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al. (1988) *SIAM J. Applied Math.* 48:1073. Preferred methods for determining identity are designed to give the largest match between the sequences tested. Methods of determining identity are described in publicly available computer programs. Preferred computer program methods for determining identity between two sequences include the GCG program package, including GAP (Devereux et al. (1984) *Nucleic Acids Res.* 12:387-395; Genetics Computer Group, University of Wisconsin, Madison, Wis.), BLASTP, BLASTN, and FASTA (Altschul et al. (1990) *J. Mol. Biol.* 215:403-410). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

B. Combination Therapy with Anti-CD70 and Anti-LSC Target Antibodies

The present invention relates to combination therapies and their use in the treatment of malignancies, particularly myeloid malignancies, preferably acute myeloid leukemia (AML). The combinations or combination therapies described herein are based on the use of antibody molecules that bind CD70 in combination with other agents.

In a first aspect, the combinations or combination therapies of the invention comprise or consist of antibody molecules that bind to different targets. The combinations comprise an antibody molecule that binds to CD70 and at least one antibody molecule that binds to a leukemic stem cell target.

All of the combinations in accordance with the present invention comprise an antibody molecule that binds to CD70. As described elsewhere herein, CD70 is a member of the tumor necrosis family (TNF) superfamily of proteins and is a type II transmembrane glycoprotein. It is a ligand for the TNF receptor CD27. CD70 is transiently expressed on antigen-activated T and B cells and mature dendritic cells and the CD70-CD27 signaling pathway plays an important role in regulating the immune response.

Constitutive expression of CD70 has been observed on many types of hematological malignancies and solid carcinomas, rendering this protein an attractive target for the development of anti-cancer therapies. CD70 has been identified as a particularly interesting target for the development of treatments for myeloid malignancies, specifically acute myeloid leukemia (AML); see for example Perna et al. (2017) *Cancer Cell* 32:506-519 and Riether et al. (2017) *J Exp Med.* 214(2):359-380, both incorporated herein by reference.

CD70 is thought to promote cancer progression in a number of ways including direct effects in promoting tumor cell proliferation and survival. Upregulated CD70 expression is also thought to play a role in immunosuppression in the tumor microenvironment by activating T regulatory cells and dampening the activity of tumor infiltrating lymphocytes (TILs). Based on this tumor immunosuppressive activity, CD70 can be classified as an immune checkpoint target. In AML, the expression of CD70 and its receptor CD27 has been detected on AML blasts, and signaling via the CD70-CD27 pathway has been linked to the stem-cell behavior of AML blast populations (Riether et al. (2017) ibid).

In the first aspect of the present invention, the antibody molecule that binds CD70 is combined with at least one antibody molecule that binds to a leukemic stem cell target. The combinations may comprise or consist of an antibody molecule that binds CD70 together with antibody molecules that bind to at least two different leukemic stem cell targets, at least three different leukemic stem cell targets, at least four different leukemic stem cell targets, or at least five different leukemic stem cell targets.

Leukemic stem cells or "LSCs" are a distinct population of leukemia cells that possess stem-like properties, for example self-renewal capacity. In particular embodiments, the LSC targets to which the antibody molecules of the combination bind are independently selected from the group consisting of: TIM-3; Galectin-9; CD47; IL1RAP; LILRB2; CLL-1; CD123; CD33; SAIL; GPR56; CD44; E-selectin; CXCR4; CD25; CD32; PR1; WT1; ADGRE2; CCR1; TNFRSF1B and CD96 (Al-Mawali. (2013) *J Stem Cell Res Ther.* 3(4):1-8; Daria et al. (2016) *Leukemia* 30:1734-1741; Rashildi & Walter (2016) *Expert Review of Hematology* 9(4):335-350; Cho et al. (2017) *Korean J Intern Med.* 32(2):248-257)).

In certain embodiments, the combination comprises or consists of an antibody molecule that binds CD70 and an antibody molecule that binds to a LSC target selected from: TIM-3 or Galectin-9. In preferred embodiments the LSC target is TIM-3.

TIM-3 is a receptor expressed on IFN-γ producing T cells, FoxP3+ Treg cells and innate immune cells (macrophages and dendritic cells). Similar to CD70, TIM-3 has also been classified as an immune checkpoint target in cancer since the interaction of TIM-3 with its ligands plays an important role in inhibiting Th1 responses (Das et al. (2017) *Immunol Rev.* 276(1): 97-111). In the development of cancer, high levels of TIM-3 expression have been found to correlate with suppression of T cells responses and T cell dysfunction, indicating an important role for TIM-3 in dampening the body's anti-tumor immune response (Japp et al. (2015) *Cancer Immunol Immunother.* 64:1487-1494). In support of this, inhibition of TIM-3 signaling in preclinical tumor models has been found to restore anti-tumor immunity (Sakuishi et al. (2010) *J Exp Med.* 207:2187-2194). TIM-3 has also been identified as a promising therapeutic target expressed directly on the surface of leukemic stem cells, particularly AML stem cells (Jan et al. (2011) *Proc Natl Acad Sci. USA* 108:5009-5014; Kikushige et al. (2010) *Cell Stem Cell.* 7:708-717; Kikushige & Miyamoto (2013) *Int J Hematol.* 98:627-633; Goncalves Silva et al. (2015) *Oncotarget* 6:33823-33833; Kikushige et al. (2015) *Cell Stem Cell* 17:341-352).

Without wishing to be bound by theory, combination therapies of the present invention including antibody molecules that bind to CD70 and antibody molecules that bind to TIM-3 are thought to be particularly effective for the treatment of malignancies, particularly myeloid malignancies, by virtue of the combined effect at the level of the leukemic stem cells. A large body of evidence suggests that LSCs are critical for the initiation and maintenance of leukemia. Therefore the targeting of this cell population via CD70 antibodies and antibodies that specifically bind a second LSC target such as TIM-3 is thought to be an effective way in which to target a critical population of tumor cells. CD70 and the LSC targets described herein, particularly TIM-3, also serve as important regulators of the anti-tumor response i.e. they represent immune checkpoint proteins that can be targeted so as to stimulate the body's anti-tumor response. It follows that the combination therapies described herein are capable of mediating direct therapeutic effects at the level of tumor cells, particularly myeloid leukemia cells, and also indirect effects via stimulation of an anti-tumor immune response.

In certain embodiments, the combination comprises or consists of an antibody molecule that binds to CD70 and an antibody molecule that binds to the LSC target CD47.

CD47 is a transmembrane protein that displays a relatively ubiquitous expression pattern. CD47 binds to its receptor SIRPα expressed on phagocytic cells, and this binding interaction transmits a "don't eat me" signal that inhibits phagocytosis of the CD47-expressing cell. Similar to both CD70 and TIM-3, CD47 has been classified as an important immune checkpoint target in cancer since the interaction between CD47 on tumor cells and its receptor SIRPα on phagocytic cells has been identified as a means by which tumor cells evade phagocytosis mediated by macrophages, neutrophils and dendritic cells present in the tumor environment. CD47 has been found to be highly expressed on a variety of different tumor cell types, including AML cells (Ponce et al. (2017) *Oncotarget* 8(7): 11284-11301), and disruption of CD47-SIRPα signaling using a SIRPα-Fc fusion was found to eliminate AML stem cells in a xenograft model (Theocharides et al. (2012) *J. Exp. Med.* 209(10): 1883-1899).

Without wishing to be bound by theory, combination therapies of the present invention including antibody molecules that bind CD70 and antibody molecules that bind CD47 are thought to be particularly effective for the treatment of malignancies, particularly myeloid malignancies, by virtue of the combined effect at the level of leukemic stem cells and the innate immune system. The antibody molecule that binds to CD70 may serve as an opsonizing antibody and the antibody molecule that binds to CD47 may enhance phagocytosis of the CD70-expressing tumor cells by blocking the interaction between CD47 and SIRPα.

In certain embodiments, the combination comprises or consists of an antibody molecule that binds to CD70 and an antibody molecule that binds to the LSC target IL1RAP.

IL1RAP is an immunoglobulin superfamily receptor expressed in liver, skin, placenta, thymus and lung. It serves as a co-receptor for IL1R1 to mediate signaling via the cytokine IL-1, and as a co-receptor for IL1R4 and IL1R3 to mediate signaling via IL-33 and IL-36, respectively. Overexpression of IL1RAP has been detected on candidate chronic myeloid leukemia stem cells, and mononuclear cells of patients with acute myeloid leukemia. Furthermore, antibodies targeting IL1RAP have been reported as having beneficial therapeutic effects in xenograft models of CML and AML (Agerstam et al. (2015) *Proc Natl Acad Sci USA* 112(34): 10786-91; Agerstam et al. (2016) *Blood* 128(23): 2683-2693).

Without wishing to be bound by theory, combination therapies of the present invention including antibody molecules that bind to CD70 and antibody molecules that bind to IL1RAP are thought to be particularly effective for the treatment of malignancies, particularly myeloid malignancies, by virtue of the combined effect at the level of leukemic stem cells. Antibodies targeting IL1RAP have been found to be particularly effective for the killing of CML and AML stem cells (Jaras et al. (2010) *Proc Natl Acad Sci USA* 107(37): 16280-16285; Askmyr et al. (2013) *Blood* 121(18): 3709-3713). Furthermore, the IL-1 receptor complex is known to signal via the NF-κB signaling pathway and this pathway has already been identified as an attractive target in the treatment of AML (see Bosman et al. (2016) *Crit Rev Oncol Hematol.* 98: 35-44). It follows, that the combination of an antibody molecule that binds to CD70 and an antibody molecule that binds to IL1RAP may be particularly efficacious based on dual targeting/inhibition of the NF-κB signaling pathway in LSCs.

In certain embodiments, the combination comprises or consists of an antibody molecule that binds to CD70 and an antibody molecule that binds to the LSC target LILRB2.

LILRB2 is an immunoglobulin superfamily receptor expressed on a variety of immune cell types including hematopoietic stem cells, monocytes, macrophages, and dendritic cells. LILRB2 has been implicated in cancer development, and expression has been reported on various cancer cells including AML and CML cells (Kang et al. (2015) *Nat Cell Biol.* 17:665-677; Colovai et al. (2007) *Cytometry B Clin Cytom.* 72:354-62).

Without wishing to be bound by theory, combination therapies of the present invention including antibody molecules that bind to CD70 and antibody molecules that bind to LILRB2 are thought to be particularly effective for the treatment of malignancies, particularly myeloid malignancies, by virtue of the combined effect at the level of leukemic stem cells. Since LILRB2 has also been identified as a protein that interacts with TIM-3, the effect of LILRB2 antibodies may also be mediated via the TIM-3 signaling pathway.

In certain embodiments, the combination comprises or consists of an antibody molecule that binds CD70, an antibody molecule that binds to a first leukemic stem cell target and an antibody molecule that binds to a second leukemic stem cell target, wherein the first and second leukemic stem cell targets are different. The first and second leukemic stem cell targets may be independently selected from the group consisting of: TIM-3; Galectin-9; CD47; IL1RAP; LILRB2; CLL-1; CD123; CD33; SAIL; GPR56; CD44; E-selectin; CXCR4; CD25; CD32; PR1; WT1; ADGRE2; CCR1; TNFRSF1B and CD96. In preferred embodiments, the first and second leukemic stem cell targets are independently selected from the group consisting of: TIM-3; Galectin-9; CD47; IL1RAP and LILRB2.

In preferred embodiments, the combination comprises or consists of an antibody molecule that binds CD70, an antibody molecule that binds TIM-3 and an antibody molecule that binds CD47. In further preferred embodiments, the combination comprises or consists of an antibody molecule that binds CD70, an antibody molecule that binds TIM-3 and an antibody molecule that binds IL1RAP. In further preferred embodiments, the combination comprises or consists of an antibody molecule that binds CD70, an antibody molecule that binds TIM-3, an antibody molecule that binds CD47 and an antibody molecule that binds IL1RAP.

The antibody molecules of the present combinations i.e. the antibody molecules that bind CD70 and the antibody molecules that bind the one or more LSC targets may be selected from any suitable antibody molecules displaying immunoreactivity for their respective target. As noted above, the term "antibody molecule" is used herein to mean full-length antibodies in addition to antigen binding fragments thereof.

The antibodies of the combinations described herein are intended for human therapeutic use and therefore, will typically be of the IgA, IgD, IgE, IgG, IgM type, often of the IgG type, in which case they can belong to any of the four sub-classes IgG1, IgG2a and b, IgG3 or IgG4. In preferred embodiments, the antibodies of the combinations described herein are IgG antibodies, preferably IgG1 antibodies.

The antibodies may be monoclonal, polyclonal, multispecific (e.g. bispecific) antibodies, provided that they exhibit the appropriate immunological specificity for their target(s). Monoclonal antibodies are preferred since they are highly specific, being directed against a single antigenic site.

The antigen binding fragments of the combinations described herein will typically comprise a portion of a full-length antibody, generally the antigen binding or variable domain thereof. Examples of antibody fragments include Fab, Fab', F(ab')2, bi-specific Fab's, and Fv fragments, linear antibodies, single-chain antibody molecules, a single chain variable fragment (scFv) and multispecific antibodies formed from antibody fragments (see Holliger and Hudson (2005) *Nature Biotechnol.* 23:1126-36, incorporated herein by reference).

The antibody molecules of the combinations described herein may exhibit high human homology. Such antibody molecules having high human homology may include antibodies comprising VH and VL domains of native non-human antibodies which exhibit sufficiently high % sequence identity to human germline sequences. In certain embodiments, the antibody molecules are humanized or germlined variants of non-human antibodies, for example antibodies comprising VH and VL domains of camelid conventional antibodies engineered so as to be humanized, or germlined variants of the original antibodies.

In non-limiting embodiments, the antibody molecules of the combinations may comprise CH1 domains and/or CL domains (from the heavy chain and light chain, respectively), the amino acid sequence of which is fully or substantially human. For antibody molecules intended for human therapeutic use, it is typical for the entire constant region of the antibody, or at least a part thereof, to have fully or substantially human amino acid sequence. Therefore, one or more or any combination of the CH1 domain, hinge region, CH2 domain, CH3 domain and CL domain (and CH4 domain if present) may be fully or substantially human with respect to its amino acid sequence.

Advantageously, the CH1 domain, hinge region, CH2 domain, CH3 domain and CL domain (and CH4 domain if present) may all have fully or substantially human amino acid sequence. In the context of the constant region of a humanized or chimeric antibody, or an antibody fragment, the term "substantially human" refers to an amino acid sequence identity of at least 90%, or at least 92%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence, excepting those embodiments where the presence of a "fully human" hinge region is expressly required.

The antibody molecules of the combinations may have one or more amino acid substitutions, insertions or deletions within the constant region of the heavy and/or the light chain, particularly within the Fc region. Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites).

The antibody molecules of the combinations may be modified with respect to their binding properties to Fc receptors, for example to modulate effector function. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al. (1992) *J. Exp. Med.* 176:1191-1195 and Shopes, B (1992) *J. Immunol.* 148:2918-2922, incorporated herein by reference.

The antibody molecules may also be modified so as to form immunoconjugates comprising an antibody conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fc regions may also be engineered for half-life extension, for example as described by Chan and Carter (2010) *Nature Reviews: Immunology* 10:301-316, incorporated herein by reference.

In yet another embodiment, the Fc region is modified to increase the ability of the antibody molecule to mediate antibody dependent cellular cytotoxicity (ADCC) and/or to increase the affinity of the antibody for an Fcγ receptor by modifying one or more amino acids.

In particular embodiments, the Fc region may be engineered such that there is no effector function. In certain embodiments, the antibody molecules of the invention may have an Fc region derived from naturally-occurring IgG isotypes having reduced effector function, for example IgG4. Fc regions derived from IgG4 may be further modified to increase therapeutic utility, for example by the introduction of modifications that minimize the exchange of arms between IgG4 molecules in vivo. Fc regions derived from IgG4 may be modified to include the S228P substitution.

In certain embodiments, the antibody molecules of the combinations are modified with respect to glycosylation. For example, an aglycosylated antibody can be made (i.e., the antibody lacks glycosylation). Glycosylation can be altered to, for example, increase the affinity of the antibody for the target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

In certain embodiments, the antibody molecules of the combinations are altered so as to be hypofucosylated i.e. having reduced amounts of fucosyl residues, or to be fully or partially de-fucosylated (as described by Natsume et al. (2009) *Drug Design Development and Therapy* 3:7-16) or to have increased bisecting GlcNac structures. Such altered glycosylation patterns have been demonstrated to increase the ADCC activity of antibodies, producing typically 10-fold enhancement of ADCC relative to an equivalent antibody comprising a "native" human Fc domain. Such carbohydrate modifications can be accomplished by, for example, expressing the antibody in a host cell with altered glycosylation enzymatic machinery (as described by Yamane-Ohnuki and Satoh (2009) mAbs 1(3):230-236). Examples of non-fucosylated antibodies with enhanced ADCC function are those produced using the Potelligent™ technology of BioWa Inc.

Antibody molecules of the combinations described herein may possess antibody effector function, for example one or more of antibody-dependent cellular cytotoxicity (ADCC), complement-dependent cytotoxicity (CDC) and antibody-dependent cellular phagocytosis (ADCP).

The antibody molecules of the combinations may be modified within the Fc region to increase binding affinity for the neonatal Fc receptor FcRn. The increased binding affinity may be measurable at acidic pH (for example from about approximately pH 5.5 to approximately pH 6.0). The increased binding affinity may also be measurable at neutral pH (for example from approximately pH 6.9 to approximately pH 7.4). By "increased binding affinity" is meant increased binding affinity to FcRn relative to the unmodified Fc region. Typically the unmodified Fc region will possess the wild-type amino acid sequence of human IgG1, IgG2, IgG3 or IgG4. In such embodiments, the increased FcRn binding affinity of the antibody molecule having the modified Fc region will be measured relative to the binding affinity of wild-type IgG1, IgG2, IgG3 or IgG4 for FcRn.

In preferred embodiments, one or more amino acid residues within the Fc region may be substituted with a different amino acid so as to increase binding to FcRn. Several Fc substitutions have been reported that increase FcRn binding and thereby improve antibody pharmacokinetics. Such substitutions are reported in, for example, Zalevsky et al. (2010) *Nat. Biotechnol.* 28(2):157-9; Hinton et al. (2006) *J Immunol.* 176:346-356; Yeung et al. (2009) *J Immunol.* 182:7663-7671; Presta LG. (2008) *Curr. Op. Immunol.* 20:460-470; and Vaccaro et al. (2005) *Nat. Biotechnol.* 23(10):1283-88, the contents of which are incorporated herein by reference in their entirety.

In preferred embodiments, one or more of the antibody molecules of the combinations described herein comprises a modified human IgG Fc domain comprising or consisting of the amino acid substitutions H433K and N434F, wherein the Fc domain numbering is in accordance with EU numbering. In a further preferred embodiment, one or more of the antibody molecules of the combinations described herein comprises a modified human IgG Fc domain comprising or consisting of the amino acid substitutions M252Y, S254T, T256E, H433K and N434F, wherein the Fc domain numbering is in accordance with EU numbering.

CD70 Antibodies

Antibody molecules binding to CD70 that may be incorporated into any of the combinations described herein include but are not limited to: CD70 antibodies that inhibit interaction of CD70 with CD27; CD70 antibodies that compete with CD27 for CD70 binding; CD70 antibodies that inhibit CD70-induced CD27 signaling; CD70 antibodies that inhibit Treg activation and/or proliferation; CD70 antibodies that deplete CD70-expressing cells; CD70 antibodies that induce lysis of CD70-expressing cells; CD70 antibodies that possess ADCC, CDC functionality, and/or induce ADCP.

Exemplary CD70 antibodies are ARGX-110 described in WO2012/123586 (incorporated herein by reference), SGN-70 (WO2006/113909, and McEarChern et al. (2008) *Clin Cancer Res.* 14(23):7763, both incorporated herein by reference) and those CD70 antibodies described in WO2006/044643 and WO2007/038637 (each incorporated herein by reference).

WO2006/044643 describes CD70 antibodies containing an antibody effector domain which can mediate one or more of ADCC, ADCP, CDC or ADC and either exert a cytostatic or cytotoxic effect on a CD70-expressing cancer or exert an immunosuppressive effect on a CD70-expressing immunological disorder in the absence of conjugation to a cytostatic or cytotoxic agent. The antibodies exemplified therein are based on the antigen-binding regions of two monoclonal antibodies, denoted 1F6 and 2F2.

WO2007/038637 describes fully human monoclonal antibodies that bind to CD70. These antibodies are characterized by binding to human CD70 with a $K_D$ of $1 \times 10^{-7}$ M or less. The antibodies also bind to, and are internalized by, renal cell carcinoma tumor cell lines which express CD70, such as 786-O.

ARGX-110 is an IgG1 anti-CD70 antibody that has been shown to inhibit the interaction of CD70 with its receptor CD27 (Silence et al. (2014) *MAbs.* Mar-Apr;6(2):523-32, incorporated herein by reference). In particular, ARGX-110 has been shown to inhibit CD70-induced CD27 signaling. Levels of CD27 signaling may be determined by, for example, measurement of serum soluble CD27 as described in Riether et al. (supra) or of IL-8 expression as described in Silence et al. (supra). Without being bound by theory, inhibiting CD27 signaling is thought to reduce activation and/or proliferation of Treg cells, thereby reducing inhibition of anti-tumor effector T cells. AGRX-110 has also been demonstrated to deplete CD70-expressing tumor cells. In particular, ARGX-110 has been shown to lyse CD70-expressing tumor cells via antibody-dependent cellular cytotoxicity (ADCC) and complement-dependent cytotoxicity (CDC), and also to increase antibody-dependent cellular phagocytosis (ADCP) of CD70-expressing cells (Silence et al., supra).

The CDR, VH and VL amino acid sequences of ARGX-110 are shown in the table below.

TABLE 1

| ARGX-110 Sequence | | SEQ ID NO: |
|---|---|---|
| HCDR1 | VYYMN | 1 |
| HCDR2 | DINNEGGTTYYADSVKG | 2 |
| HCDR3 | DAGYSNHVPIFDS | 3 |
| VH | EVQLVESGGGLVQPGGSLRLSCAASGFTFSVYYMNWVR QAPGKGLEWVSDINNEGGTTYYADSVKGRFTISRDNSKN SLYLQMNSLRAEDTAVYYCARDAGYSNHVPIFDSWGQGT LVTVSS | 4 |
| LCDR1 | GLKSGSVTSDNFPT | 5 |
| LCDR2 | NTNTRHS | 6 |
| LCDR3 | ALFISNPSVE | 7 |
| VL | QAVVTQEPSLTVSPGGTVTLTCGLKSGSVTSDNFPTWYQ QTPGQAPRLLIYNTNTRHSGVPDRFSGSILGNKAALTIT GAQADDEAEYFCALFISNPSVEFGGGTQLTVLG | 8 |

In certain embodiments, the antibody molecule that binds to CD70 comprises a variable heavy chain domain (VH) and a variable light chain domain (VL) wherein the VH and VL domains comprise or consist of the CDR sequences:
HCDR3 comprising or consisting of SEQ ID NO: 3;
HCDR2 comprising or consisting of SEQ ID NO: 2;
HCDR1 comprising or consisting of SEQ ID NO: 1;
LCDR3 comprising or consisting of SEQ ID NO: 7;
LCDR2 comprising or consisting of SEQ ID NO: 6; and
LCDR1 comprising or consisting of SEQ ID NO: 5.

In certain embodiments, the antibody molecule that binds to CD70 comprises a variable heavy chain domain (VH domain) comprising or consisting of a sequence at least 70%, at least 80%, at least 90% or at least 95% identical to SEQ ID NO: 4 and a variable light chain domain (VL domain) comprising or consisting of a sequence at least 70%, at least 80%, at least 90% or at least 95% identical to SEQ ID NO: 8. In certain embodiments, the antibody molecule that binds to CD70 comprises a variable heavy chain domain (VH domain) comprising or consisting of SEQ ID NO: 4 and a variable light chain domain (VL domain) comprising or consisting of SEQ ID NO: 8.

CD70 antibody molecules that may be incorporated into the combinations described herein include antibody drug conjugates (ADCs). ADCs are antibodies attached to active agents, for example auristatins and maytansines or other cytotoxic agents. Certain ADCs maintain antibody blocking and/or effector function (e.g. ADCC, CDC, ADCP) while also delivering the conjugated active agent to cells expressing the target (e.g. CD70). Examples of anti-CD70 ADCs include vorsetuzumab mafodotin (also known as SGN-75, Seattle Genetics), SGN-70A (Seattle Genetics), and MDX-1203/BMS936561 (Bristol-Myers Squibb), each of which may be used in accordance with the invention. Suitable anti-CD70 ADCs are also described in WO2008074004 and WO2004073656, each of which is incorporated herein by reference.

CD70 antibody molecules that may be incorporated into the combinations described herein also include SIRPα-antibody molecule fusion proteins or "licMABs" (local inhibitory checkpoint monoclonal antibodies), as described for example in Ponce et al. (2017) (supra). These SIRPα-antibody molecule fusion proteins or licMABs comprise an antibody or antibody molecule (in this case a CD70 antibody or antibody molecule) fused to a domain of the SIRPα protein, in particular, the extracellular immunoglobulin V-like domain.

LSC Target Antibodies
TIM-3 and Galectin-9 Antibodies

Antibody molecules binding to LSC targets that may be incorporated into the combinations described herein include antibody molecules that mediate their effects via TIM-3. These effects may be mediated via direct binding to TIM-3 or via binding to a LSC target associated with TIM-3 signaling. In certain embodiments, the LSC target antibody molecules of the combinations described herein inhibit the interaction of TIM-3 with one or more TIM-3 interacting proteins. The TIM-3 interacting proteins may be selected from: CEACAM-1; HMGB-1; phosphatidylserine; Galectin-9; LILRB2; and combinations thereof. In one embodiment, the LSC target antibody molecule of the combination inhibits the interaction of TIM-3 with its ligand, Galectin-9. In one embodiment, the LSC target antibody molecule of the combination inhibits the interaction of TIM-3 with its ligand, LILRB2.

In certain embodiments, the LSC target antibody molecule of the combinations binds to Galectin-9. In certain embodiments, the LSC target antibody molecule of the combinations binds to TIM-3. For embodiments wherein the LSC target is TIM-3, the antibody molecule may achieve one or more of the following effects: reduced NF-κB signaling; reduced Wnt/β-catenin signaling; reduced stemness of AML cells; or a combination thereof. For antibody molecules that bind to TIM-3, the antibody molecules may inhibit the interaction of TIM-3 with one or more TIM-3 interacting proteins. The TIM-3 interacting proteins may be selected from: CEACAM-1; HMGB-1; phosphatidylserine; Galectin-9; and combinations thereof. In one embodiment, the antibody molecule that binds to TIM-3 inhibits the interaction of TIM-3 with its ligand, Galectin-9.

In certain embodiments, the LSC target antibody molecule of the combinations inhibits the interaction of TIM-3 and LILRB2. In such embodiments, the antibody molecule preferably binds TIM-3 and inhibits binding of TIM-3 to LILRB2.

Antibody molecules that bind to TIM-3 and that may be incorporated into the combinations described herein include but are not limited to the TIM-3 antibodies described in any of the following: U.S. Pat. Nos. 8,647,623; 8,552,156; 9,605,070; 8,841,418; 9,631,026; 9,556,270; WO2016/111947, each of which is incorporated herein by reference. Antibody molecules that bind to TIM-3 and that may be incorporated into the combinations described herein also include but are not limited to: clone F38-2E2; MBG453 (Novartis); ATIK2a (Kyowa Kirin).

Antibody molecules that bind to Galectin-9 and that may be incorporated into the combinations described herein include but are not limited to clone 9M1-3.

CD47 Antibodies

In certain embodiments, the combinations of the invention comprise an antibody molecule that binds CD47. CD47 antibody molecules for use in the combinations described herein are antibody molecules that inhibit the interaction between CD47 and SIRPα. As noted elsewhere herein, the interaction between the ligand CD47 expressed by the LSC and the receptor SIRPα expressed by phagocytic cells transmits a "don't eat me" signal downstream of the SIRPα receptor. The CD47 antibody molecules of the combinations described herein can therefore increase phagocytosis of tumor cells, particularly LSCs.

A variety of CD47 antibodies are available, including CD47 antibodies at different stages of clinical development. The skilled person will appreciate that any CD47 antibody suitable for human therapeutic use may be incorporated into the combinations described herein. Exemplary CD47 antibodies include but are not limited to Hu5F9-G4; CC-90002; ALX148 and clone B6H12.2.

IL1RAP Antibodies

In certain embodiments, the combinations of the invention comprise an antibody molecule that binds IL1RAP. IL1RAP antibody molecules for use in the combinations described herein are preferably antibody molecules that bind to IL1RAP and inhibit signaling via the IL-1 receptor complex at the cell surface.

IL1RAP antibodies have been described, see Agerstam et al. (2015) (supra), and also WO2012/098407 and WO2014/100772. The skilled person will appreciate that any IL1RAP antibody suitable for human therapeutic use may be incorporated into the combinations described herein.

Camelid-Derived LSC Target Antibodies

The antibody molecules specifically binding to LSC targets, particularly antibody molecules specifically binding to TIM-3, Galectin-9, CD47, IL1RAP and/or LILRB2, may be camelid-derived.

For example, the antibody molecules may be selected from immune libraries obtained by a method comprising the step of immunizing a camelid with the LSC target of interest. The camelid may be immunized with a LSC target protein or polypeptide fragment thereof, or with an mRNA molecule or cDNA molecule expressing the protein or a polypeptide fragment thereof. Methods for producing antibodies in camelid species and selecting antibodies against preferred targets from camelid immune libraries are described in, for example, International Patent Application No. WO2010/001251, incorporated herein by reference.

In certain embodiments, the antibody molecules may be camelid-derived in that they comprise at least one hypervariable loop or complementarity determining region obtained from a VH domain or a VL domain of a species in the family Camelidae. In particular, the antibody molecule may comprise VH and/or VL domains, or CDRs thereof, obtained by active immunization of outbred camelids, e.g. llamas, with TIM-3, Galectin-9, CD47 or IL1RAP for example.

The term "obtained from" in this context implies a structural relationship, in the sense that the HVs or CDRs of the antibody molecule embody an amino acid sequence (or minor variants thereof) which was originally encoded by a Camelidae immunoglobulin gene. However, this does not necessarily imply a particular relationship in terms of the production process used to prepare the antibody molecule.

Camelid-derived antibody molecules may be derived from any camelid species, including inter alia, llama, dromedary, alpaca, vicuna, guanaco or camel.

Antibody molecules comprising camelid-derived VH and VL domains, or CDRs thereof, are typically recombinantly expressed polypeptides, and may be chimeric polypeptides. The term "chimeric polypeptide" refers to an artificial (non-naturally occurring) polypeptide which is created by juxtaposition of two or more peptide fragments which do not otherwise occur contiguously. Included within this definition are "species" chimeric polypeptides created by juxtaposition of peptide fragments encoded by two or more species, e.g. camelid and human.

In certain embodiments, the entire VH domain and/or the entire VL domain may be obtained from a species in the family Camelidae. In specific embodiments, the camelid-derived VH domain may comprise an amino acid sequence selected from SEQ ID NOs: 9, 11, 13, 15, 17, 19, 21, 23, 25, 27, 29, 31, 33, 35, 37, 121 and 123, whereas the camelid-derived VL domain may comprise an amino acid sequence selected from SEQ ID NOs: 10, 12, 14, 16, 18, 20, 22, 24, 26, 28, 30, 32, 34, 36, 38, 122 and 124. The camelid-derived VH domain and/or the camelid-derived VL domain may then be subject to protein engineering, in which one or more amino acid substitutions, insertions or deletions are introduced into the camelid amino acid sequence. These engineered changes preferably include amino acid substitutions relative to the camelid sequence. Such changes include "humanization" or "germlining" wherein one or more amino acid residues in a camelid-encoded VH or VL domain are replaced with equivalent residues from a homologous human-encoded VH or VL domain. In certain embodiments, the camelid-derived VH domain may exhibit at least 90%, 95%, 97%, 98% or 99% identity with the amino acid sequence shown as SEQ ID NO: 9, 11, 13, 15, 17, 19, 21, 23, 25, 27, 29, 31, 33, 35, 37, 121 or 123. Alternatively, or in addition, the camelid-derived VL domain may exhibit at least 90%, 95%, 97%, 98% or 99% identity with the amino acid sequence shown as SEQ ID NO: 10, 12, 14, 16, 18, 20, 22, 24, 26, 28, 30, 32, 34, 36, 38, 122 or 124.

Isolated camelid VH and VL domains obtained by active immunization of a camelid (e.g. llama) with a LSC target antigen (for example) can be used as a basis for engineering antibody molecules for use in the combinations described herein. Starting from intact camelid VH and VL domains, it is possible to engineer one or more amino acid substitutions, insertions or deletions which depart from the starting camelid sequence. In certain embodiments, such substitutions, insertions or deletions may be present in the framework regions of the VH domain and/or the VL domain.

In other embodiments, there are provided "chimeric" antibody molecules comprising camelid-derived VH and VL domains (or engineered variants thereof) and one or more constant domains from a non-camelid antibody, for example human-encoded constant domains (or engineered variants thereof). In such embodiments it is preferred that both the VH domain and the VL domain are obtained from the same species of camelid, for example both VH and VL may be from Lama glama or both VH and VL may be from Lama pacos (prior to introduction of engineered amino acid sequence variation). In such embodiments both the VH and the VL domain may be derived from a single animal, particularly a single animal which has been actively immunised with the antigen of interest.

As an alternative to engineering changes in the primary amino acid sequence of Camelidae VH and/or VL domains, individual camelid-derived hypervariable loops or CDRs, or combinations thereof, can be isolated from camelid VH/VL domains and transferred to an alternative (i.e. non-Camelidae) framework, e.g. a human VH/VL framework, by CDR grafting.

In certain embodiments, the antibody molecules that bind to TIM-3 are selected from antibody molecules comprising a combination of variable heavy chain CDR3 (HCDR3), variable heavy chain CDR2 (HCDR2) and variable heavy chain CDR1 (HCDR1), variable light chain CDR3 (LCDR3), variable light chain CDR2 (LCDR2) and variable light chain CDR1 (LCDR1) selected from the following:

(i) HCDR3 comprising SEQ ID NO: 41; HCDR2 comprising SEQ ID NO: 40; HCDR1 comprising SEQ ID NO: 39; LCDR3 comprising SEQ ID NO: 80; LCDR2 comprising SEQ ID NO: 79; and LCDR1 comprising SEQ ID NO: 78;

(ii) HCDR3 comprising SEQ ID NO: 43; HCDR2 comprising SEQ ID NO: 42; HCDR1 comprising SEQ ID NO: 39; LCDR3 comprising SEQ ID NO: 83; LCDR2 comprising SEQ ID NO: 82; and LCDR1 comprising SEQ ID NO: 81;

(iii) HCDR3 comprising SEQ ID NO: 46; HCDR2 comprising SEQ ID NO: 45; HCDR1 comprising SEQ ID NO: 44; LCDR3 comprising SEQ ID NO: 86; LCDR2 comprising SEQ ID NO: 85; and LCDR1 comprising SEQ ID NO: 84;

(iv) HCDR3 comprising SEQ ID NO: 49; HCDR2 comprising SEQ ID NO: 48; HCDR1 comprising SEQ ID NO: 47; LCDR3 comprising SEQ ID NO: 88; LCDR2 comprising SEQ ID NO: 82; and LCDR1 comprising SEQ ID NO: 87;

(v) HCDR3 comprising SEQ ID NO: 52; HCDR2 comprising SEQ ID NO: 51; HCDR1 comprising SEQ ID NO: 50; LCDR3 comprising SEQ ID NO: 91; LCDR2 comprising SEQ ID NO: 90; and LCDR1 comprising SEQ ID NO: 89;

(vi) HCDR3 comprising SEQ ID NO: 55; HCDR2 comprising SEQ ID NO: 54; HCDR1 comprising SEQ ID NO: 53; LCDR3 comprising SEQ ID NO: 94; LCDR2 comprising SEQ ID NO: 93; and LCDR1 comprising SEQ ID NO: 92;

(vii) HCDR3 comprising SEQ ID NO: 58; HCDR2 comprising SEQ ID NO: 57; HCDR1 comprising SEQ ID NO: 56; LCDR3 comprising SEQ ID NO: 97; LCDR2 comprising SEQ ID NO: 96; and LCDR1 comprising SEQ ID NO: 95;

(viii) HCDR3 comprising SEQ ID NO: 60; HCDR2 comprising SEQ ID NO: 59; HCDR1 comprising SEQ ID NO: 50; LCDR3 comprising SEQ ID NO: 100; LCDR2 comprising SEQ ID NO: 99; and LCDR1 comprising SEQ ID NO: 98;

(ix) HCDR3 comprising SEQ ID NO: 63; HCDR2 comprising SEQ ID NO: 62; HCDR1 comprising SEQ ID NO: 61; LCDR3 comprising SEQ ID NO: 103; LCDR2 comprising SEQ ID NO: 102; and LCDR1 comprising SEQ ID NO: 101;

(x) HCDR3 comprising SEQ ID NO: 65; HCDR2 comprising SEQ ID NO: 64; HCDR1 comprising SEQ ID NO: 39; LCDR3 comprising SEQ ID NO: 106; LCDR2 comprising SEQ ID NO: 105; and LCDR1 comprising SEQ ID NO: 104;

(xi) HCDR3 comprising SEQ ID NO: 67; HCDR2 comprising SEQ ID NO: 66; HCDR1 comprising SEQ ID NO: 50; LCDR3 comprising SEQ ID NO: 109; LCDR2 comprising SEQ ID NO: 108; and LCDR1 comprising SEQ ID NO: 107;

(xii) HCDR3 comprising SEQ ID NO: 69; HCDR2 comprising SEQ ID NO: 68; HCDR1 comprising SEQ ID NO: 50; LCDR3 comprising SEQ ID NO: 112; LCDR2 comprising SEQ ID NO: 111; and LCDR1 comprising SEQ ID NO: 110;

(xiii) HCDR3 comprising SEQ ID NO: 72; HCDR2 comprising SEQ ID NO: 71; HCDR1 comprising SEQ ID NO: 70; LCDR3 comprising SEQ ID NO: 115; LCDR2 comprising SEQ ID NO: 114; and LCDR1 comprising SEQ ID NO: 113;

(xiv) HCDR3 comprising SEQ ID NO: 74; HCDR2 comprising SEQ ID NO: 73; HCDR1 comprising SEQ ID NO: 50; LCDR3 comprising SEQ ID NO: 117; LCDR2 comprising SEQ ID NO: 111; and LCDR1 comprising SEQ ID NO: 116; and (xv) HCDR3 comprising SEQ ID NO: 77; HCDR2 comprising SEQ ID NO: 76; HCDR1 comprising SEQ ID NO: 75; LCDR3 comprising SEQ ID NO: 120; LCDR2 comprising SEQ ID NO: 119; and LCDR1 comprising SEQ ID NO: 118.

In certain embodiments, the antibody molecules that bind to TIM-3 are selected from antibody molecules comprising or consisting of a variable heavy chain domain (VH) and a variable light chain domain (VL) selected from the following:

(i) a VH domain comprising or consisting of the amino acid sequence of SEQ ID NO: 9 or an amino acid sequence having at least 80%, 90%, 95%, 98% 99% identity thereto, and a VL domain comprising or consisting of the amino acid sequence of SEQ ID NO: 10 or an amino acid sequence having at least 80%, 90%, 95%, 98% 99% identity thereto;

(ii) a VH domain comprising or consisting of the amino acid sequence of SEQ ID NO: 11 or an amino acid sequence having at least 80%, 90%, 95%, 98% 99% identity thereto, and a VL domain comprising or consisting of the amino acid sequence of SEQ ID NO: 12 or an amino acid sequence having at least 80%, 90%, 95%, 98% 99% identity thereto;

(iii) a VH domain comprising or consisting of the amino acid sequence of SEQ ID NO: 13 or an amino acid sequence having at least 80%, 90%, 95%, 98% 99% identity thereto, and a VL domain comprising or consisting of the amino acid sequence of SEQ ID NO: 14 or an amino acid sequence having at least 80%, 90%, 95%, 98% 99% identity thereto;

(iv) a VH domain comprising or consisting of the amino acid sequence of SEQ ID NO: 15 or an amino acid sequence having at least 80%, 90%, 95%, 98% 99% identity thereto, and a VL domain comprising or consisting of the amino acid sequence of SEQ ID NO: 16 or an amino acid sequence having at least 80%, 90%, 95%, 98% 99% identity thereto;

(v) a VH domain comprising or consisting of the amino acid sequence of SEQ ID NO: 17 or an amino acid sequence having at least 80%, 90%, 95%, 98% 99% identity thereto, and a VL domain comprising or consisting of the amino acid sequence of SEQ ID NO: 18 or an amino acid sequence having at least 80%, 90%, 95%, 98% 99% identity thereto;

(vi) a VH domain comprising or consisting of the amino acid sequence of SEQ ID NO: 19 or an amino acid sequence having at least 80%, 90%, 95%, 98% 99% identity thereto, and a VL domain comprising or consisting of the amino acid sequence of SEQ ID NO: 20 or an amino acid sequence having at least 80%, 90%, 95%, 98% 99% identity thereto;

(vii) a VH domain comprising or consisting of the amino acid sequence of SEQ ID NO: 21 or an amino acid sequence having at least 80%, 90%, 95%, 98% 99% identity thereto, and a VL domain comprising or consisting of the amino acid sequence of SEQ ID NO: 22 or an amino acid sequence having at least 80%, 90%, 95%, 98% 99% identity thereto;

(viii) a VH domain comprising or consisting of the amino acid sequence of SEQ ID NO: 23 or an amino acid sequence having at least 80%, 90%, 95%, 98% 99% identity thereto, and a VL domain comprising or consisting of the amino acid sequence of SEQ ID NO: 24 or an amino acid sequence having at least 80%, 90%, 95%, 98% 99% identity thereto;

(ix) a VH domain comprising or consisting of the amino acid sequence of SEQ ID NO: 25 or an amino acid sequence having at least 80%, 90%, 95%, 98% 99% identity thereto, and a VL domain comprising or consisting of the amino acid sequence of SEQ ID NO: 26 or an amino acid sequence having at least 80%, 90%, 95%, 98% 99% identity thereto;

(x) a VH domain comprising or consisting of the amino acid sequence of SEQ ID NO: 27 or an amino acid sequence having at least 80%, 90%, 95%, 98% 99% identity thereto, and a VL domain comprising or consisting of the amino acid sequence of SEQ ID NO: 28 or an amino acid sequence having at least 80%, 90%, 95%, 98% 99% identity thereto;

(xi) a VH domain comprising or consisting of the amino acid sequence of SEQ ID NO: 29 or an amino acid sequence having at least 80%, 90%, 95%, 98% 99% identity thereto, and a VL domain comprising or consisting of the amino acid sequence of SEQ ID NO: 30 or an amino acid sequence having at least 80%, 90%, 95%, 98% 99% identity thereto;

(xii) a VH domain comprising or consisting of the amino acid sequence of SEQ ID NO: 31 or an amino acid sequence having at least 80%, 90%, 95%, 98% 99% identity thereto, and a VL domain comprising or consisting of the amino acid sequence of SEQ ID NO: 32 or an amino acid sequence having at least 80%, 90%, 95%, 98% 99% identity thereto;

(xiii) a VH domain comprising or consisting of the amino acid sequence of SEQ ID NO: 33 or an amino acid sequence having at least 80%, 90%, 95%, 98% 99% identity thereto, and a VL domain comprising or consisting of the amino acid sequence of SEQ ID NO: 34 or an amino acid sequence having at least 80%, 90%, 95%, 98% 99% identity thereto;

(xiv) a VH domain comprising or consisting of the amino acid sequence of SEQ ID NO: 35 or an amino acid sequence having at least 80%, 90%, 95%, 98% 99% identity thereto, and a VL domain comprising or consisting of the amino acid sequence of SEQ ID NO: 36 or an amino acid sequence having at least 80%, 90%, 95%, 98% 99% identity thereto;
(xv) a VH domain comprising or consisting of the amino acid sequence of SEQ ID NO: 37 or an amino acid sequence having at least 80%, 90%, 95%, 98% 99% identity thereto, and a VL domain comprising or consisting of the amino acid sequence of SEQ ID NO: 38 or an amino acid sequence having at least 80%, 90%, 95%, 98% 99% identity thereto.

In certain embodiments, the antibody molecules that bind to IL1RAP are selected from antibody molecules comprising a combination of variable heavy chain CDR3 (HCDR3), variable heavy chain CDR2 (HCDR2) and variable heavy chain CDR1 (HCDR1), variable light chain CDR3 (LCDR3), variable light chain CDR2 (LCDR2) and variable light chain CDR1 (LCDR1) selected from the following:
(i) HCDR3 comprising SEQ ID NO: 127; HCDR2 comprising SEQ ID NO: 126;
  HCDR1 comprising SEQ ID NO: 125; LCDR3 comprising SEQ ID NO: 133;
  LCDR2 comprising SEQ ID NO: 132; and LCDR1 comprising SEQ ID NO: 131; and
(ii) HCDR3 comprising SEQ ID NO: 130; HCDR2 comprising SEQ ID NO: 129;
  HCDR1 comprising SEQ ID NO: 128; LCDR3 comprising SEQ ID NO: 136;
  LCDR2 comprising SEQ ID NO: 135; and LCDR1 comprising SEQ ID NO: 134.

In certain embodiments, the antibody molecules that bind to IL1RAP are selected from antibody molecules comprising or consisting of a variable heavy chain domain (VH) and a variable light chain domain (VL) selected from the following:
(i) a VH domain comprising or consisting of the amino acid sequence of SEQ ID
  NO: 121 or an amino acid sequence having at least 80%, 90%, 95%, 98% 99% identity thereto, and a VL domain comprising or consisting of the amino acid sequence of SEQ ID NO: 122 or an amino acid sequence having at least 80%, 90%, 95%, 98% 99% identity thereto; and
(ii) a VH domain comprising or consisting of the amino acid sequence of SEQ ID
  NO: 123 or an amino acid sequence having at least 80%, 90%, 95%, 98% 99% identity thereto, and a VL domain comprising or consisting of the amino acid sequence of SEQ ID NO: 124 or an amino acid sequence having at least 80%, 90%, 95%, 98% 99% identity thereto.

For embodiments wherein the domains of the antibodies or antigen binding fragments are defined by a particular percentage sequence identity to a reference sequence, the VH and/or VL domains may retain identical CDR sequences to those present in the reference sequence such that the variation is present only within the framework regions.

Antibody molecules comprising camelid-derived VH and VL domains, or CDRs thereof, can take various different antibody forms in which both a VH domain and a VL domain are present. Antibodies and antigen binding fragments within the definition of "antibody molecule" as used in the context of the claimed combinations are described elsewhere herein.

Formulation of the Combination

The different antibody molecules of the combinations may be combined or formulated in any manner allowing the combination therapy to be administered to a subject or patient in need thereof, preferably a human subject or patient. The combination may be formulated for single dose administration or for multiple dose administration.

For embodiments wherein the antibody molecules are antigen binding fragments, the antibody molecules may be combined as a multispecific antibody, for example a bispecific antibody. For example, if the combination comprises a Fab fragment that binds CD70 and a Fab fragment that binds to a LSC target, the two Fab fragments may be incorporated into a single bispecific antibody molecule having the two Fab regions conjugated to an IgG Fc portion. In certain embodiments, the combination comprises or consists of a multispecific antibody, preferably a bispecific antibody, comprising an antibody molecule that binds CD70 and an antibody molecule that binds TIM-3. In certain embodiments, the combination comprises or consists of a multispecific antibody, preferably a bispecific antibody, comprising an antibody molecule that binds CD70 and an antibody molecule that binds CD47. In certain embodiments, the combination comprises or consists of a multispecific antibody, preferably a bispecific antibody, comprising an antibody molecule that binds CD70 and an antibody molecule that binds IL1RAP.

Bispecific or multispecific antibodies in accordance with the present invention may be configured according to any suitable bispecific/multispecific antibody format as described elsewhere herein. For example, the antibody molecules of the combination may be incorporated into a bispecific or multispecific antibody format such that the antibody binds to the different targets in "trans", for example the situation where each Fab arm of the Y-shaped antibody has a different binding specificity. In alternative embodiments, the antibody molecules may be incorporated into a bispecific or multispecific antibody format such that the targets are bound in the "cis" position. For example, the Fab regions or variable domains thereof may be positioned at opposite ends of an IgG Fc portion. In certain embodiments, the antibody molecules may be incorporated in an asymmetric bispecific IgG antibody format wherein the first antibody molecule is a Fab fragment forming one arm of the "Y"-shaped antibody and the second antibody molecule is a VHH domain.

In certain embodiments, antibody molecules of the combination are separate molecules that are co-formulated i.e. formulated as a single pharmaceutical composition. For embodiments wherein the antibody molecules are co-formulated, the combination or composition is suitable for simultaneous administration of the two components. The composition may be formulated for single dose administration or multiple dose administration. For embodiments in which the antibody molecules are co-formulated, the antibody molecules may be formulated in equivalent amounts, for example according to a 1:1 ratio for a combination comprising first and second antibody molecules binding to different targets. Alternatively, the antibody molecules may be formulated such that the ratio of the different antibody molecules is not 1:1. For example, for embodiments wherein the combination comprises or consists of first and second antibody molecules binding to different targets, the ratio of first and second antibody molecules may be 2:1, optionally 3:1, optionally 4:1. Alternatively, the antibody molecules may be formulated according to a ratio of 1:2, optionally 1:3, optionally 1:4.

In certain embodiments, the antibody molecules of the combination are formulated separately, for example as individual compositions. For embodiments wherein the antibody molecules are formulated separately, the possibility exists for simultaneous or separate administration of the different components or compositions. If the antibody molecules or the separate compositions containing them are administered separately, there may be sequential administration of the antibody molecules or compositions in either order. For example, the antibody molecule that binds to CD70 may be administered first followed by the antibody molecule that binds to the leukemic stem cell target or vice versa. The interval between administration of the antibody molecules or compositions may be any suitable time interval. The administration of the different compositions may be carried out once (for a single dose administration) or repeatedly (for a multiple dose administration).

For embodiments wherein the antibody molecules are co-formulated and/or for embodiments wherein the antibody molecules are provided as separate compositions, the antibody molecules may be formulated using any suitable pharmaceutical carriers or excipients.

Techniques for formulating antibodies for human therapeutic use are well known in the art and are reviewed, for example, in Wang et al. (2007) *Journal of Pharmaceutical Sciences*, 96:1-26, the contents of which are incorporated herein by reference in their entirety. For embodiments wherein the antibody molecules are formulated separately, the pharmaceutical carriers or excipients may be different for the different compositions or the same.

Pharmaceutically acceptable excipients that may be used to formulate the compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

In certain embodiments, the compositions are formulated for administration to a subject via any suitable route of administration including but not limited to intramuscular, intravenous, intradermal, intraperitoneal injection, subcutaneous, epidural, nasal, oral, rectal, topical, inhalational, buccal (e.g., sublingual), and transdermal administration. For embodiments wherein the antibody molecules are formulated separately, each composition may be formulated for administration via a different route.

For combinations of the invention comprising or consisting of agents in addition to the CD70 antibody molecule and the LSC target antibody molecule, the one or more additional agents may be formulated for administration via the same route or via a different route as compared with the first and second antibody molecules. For example, in embodiments wherein the combination includes an antibody molecule that binds to CD70, an antibody molecule that binds to a LSC target and azacitidine, the antibody molecules may be administered intravenously whilst the azacitidine may be administered subcutaneously via injection.

C. Combination Therapy with Anti-CD70 Antibodies and SIRPα Inhibitors

In a second aspect, the combinations or combination therapies of the invention comprise or consist of an antibody molecule that binds to CD70 and an agent that inhibits SIRPα signaling. Antibody molecules that bind to CD70 and that are suitable for use in the combinations of the present invention are described above and all embodiments presented in the context of the first aspect of the invention are equally applicable to this second aspect.

In the combinations or combination therapies of the second aspect of the invention, the antibody molecule that binds to CD70 is combined with an agent that inhibits SIRPα signaling. As explained elsewhere herein, SIRPα is a receptor expressed on the surface of phagocytic cells including in particular macrophages, neutrophils and dendritic cells. SIRPα is a receptor for the ligand CD47, and this ligand is expressed on the surface of a variety of different cell types. The binding of CD47 to SIRPα triggers an intracellular signaling pathway downstream of SIRPα within the phagocyte which serves to down-regulate the phagocytic activity. The consequence of this is that the CD47-SIRPα signaling axis promotes survival of CD47-expressing cells by preventing clearance of these cells by the phagocytic cells of the immune system.

As used herein, the term "agent that inhibits SIRPα signaling" is intended to mean any agent that interferes with the CD47-SIRPα signaling axis such that the "don't eat me" signal generated by this pathway is suppressed. In certain embodiments, the agent that inhibits SIRPα signaling is an antibody molecule that binds CD47 and inhibits the interaction between CD47 and SIRPα. In other embodiments, the agent that inhibits SIRPα signaling is an antibody molecule that binds SIRPα and inhibits the interaction between CD47 and SIRPα. Antibodies that bind to CD47 and SIRPα, respectively, are known in the art and could be included in the combinations described herein. Exemplary SIRPα antibodies suitable for use in the combinations described herein include but are not limited to: clone KWAR23; clone B4B6; and clone OX-119.

In certain embodiments, the agent that inhibits SIRPα signaling is a SIRPα antibody-molecule fusion protein. As defined elsewhere herein, SIRPα antibody-molecule fusion proteins comprise SIRPα or a fragment thereof together with an antibody or fragment thereof. In certain embodiments, the SIRPα antibody-molecule fusion protein comprises at least one copy of the immunoglobulin V-like domain of SIRPα, optionally multiple copies of this immunoglobulin V-like domain of SIRPα.

In certain embodiments, the agent that inhibits SIRPα signaling comprises SIRPα or the immunoglobulin V-like domain therefrom covalently linked to the Fc region of an antibody, for example an IgG1 antibody. In one embodiment, the agent that inhibits SIRPα signaling is TTI-621 (Trillium Therapeutics Inc).

In certain embodiments, the agent that inhibits SIRPα signaling comprises SIRPα or the immunoglobulin V-like domain therefrom covalently linked to a full-length IgG antibody, for example a full-length IgG1 antibody.

In preferred embodiments of the combination in accordance with this second aspect of the invention, the combination comprises or consists of an antibody molecule that binds to CD70 wherein the antibody molecule is linked to SIRPα or is linked to at least one copy of the immunoglobulin V-like domain of SIRPα. The linkage is preferably covalent. The CD70 antibody molecule may be linked to multiple copies of the immunoglobulin V-like domain of SIRPα, for example two, three, four or more copies. The CD70 antibody molecule may be linked to the SIRPα domain directly or indirectly via a linker, for example a polyglycine-serine linker.

For embodiments wherein the CD70 antibody molecule is linked, preferably covalently linked, to at least one copy of the immunoglobulin V-like domain of SIRPα, the CD70 antibody molecule preferably comprises a variable heavy chain domain (VH) and a variable light chain domain (VL) wherein the VH and VL domains comprise the CDR sequences:
  HCDR3 comprising or consisting of SEQ ID NO: 3;
  HCDR2 comprising or consisting of SEQ ID NO: 2;
  HCDR1 comprising or consisting of SEQ ID NO: 1;
  LCDR3 comprising or consisting of SEQ ID NO: 7;
  LCDR2 comprising or consisting of SEQ ID NO: 6; and
  LCDR1 comprising or consisting of SEQ ID NO: 5.

In certain embodiments, the antibody molecule that binds to CD70 and that is linked to at least one copy of the immunoglobulin V-like domain of SIRPα comprises a variable heavy chain domain (VH domain) comprising or consisting of a sequence at least 70%, at least 80%, at least 90% or at least 95% identical to SEQ ID NO: 4 and a variable light chain domain (VL domain) comprising or consisting of a sequence at least 70%, at least 80%, at least 90% or at least 95% identical to SEQ ID NO: 8. In certain embodiments, the antibody molecule that binds to CD70 and that is linked to at least one copy of the immunoglobulin V-like domain of SIRPα comprises a variable heavy chain domain (VH domain) comprising or consisting of SEQ ID NO: 4 and a variable light chain domain (VL domain) comprising or consisting of SEQ ID NO: 8.

D. Additional Agents

The combinations according to the first and second aspects of the invention may include, in addition to the antibody molecules and agents described above, one or more additional anti-cancer agents. For example, the combinations may comprise at least one additional agent for the treatment of myeloid malignancy, particularly for the treatment of AML.

In certain embodiments, the combinations described herein comprise a nucleoside metabolic inhibitor (or NMI). For example, the combinations may comprise a hypomethylating agent, for example azacitidine (also referred to herein as azacytidine, AZA or aza) or decitabine. Azacitidine is an analogue of cytidine and decitabine is its deoxy derivative. AZA and decitabine are inhibitors of DNA methyltransferases (DNMT) known to upregulate gene expression by promoter hypomethylation. Such hypomethylation disrupts cell function, thereby resulting in cytotoxic effects.

In particular embodiments, the combinations described herein comprise or consist of an antibody molecule that binds to CD70, an antibody molecule that binds to TIM-3 and azacitidine. In particular embodiments, the combinations described herein comprise or consist of an antibody molecule that binds to CD70, an antibody molecule that binds TIM-3 and decitabine. In particular embodiments, the combinations described herein comprise or consist of an antibody molecule that binds to CD70, an antibody molecule that binds to CD47 and azacitidine. In particular embodiments, the combinations described herein comprise or consist of an antibody molecule that binds to CD70, an antibody molecule that binds CD47 and decitabine. In particular embodiments, the combinations described herein comprise or consist of an antibody molecule that binds to CD70, an antibody molecule that binds to IL1RAP and azacitidine. In particular embodiments, the combinations described herein comprise or consist of an antibody molecule that binds to CD70, an antibody molecule that binds IL1RAP and decitabine.

Without wishing to be bound by theory, combinations incorporating a CD70 antibody molecule, an antibody molecule that binds a LSC target and a hypomethylating agent, for example azacitidine or decitabine, are thought to be particularly effective for the treatment of malignancy, particularly myeloid malignancy, due to the combined actions of the active agents. As described elsewhere herein, CD70, TIM-3, CD47 and IL1RAP have all been identified as targets upregulated on leukemic stem cells. It has also been found that CD70 expression is upregulated on the surface of AML blasts and lymphocytes from patients treated with the nucleoside metabolic inhibitor azacitidine (see Richardson & Patel (2014) Nat Rev Rheumatol. 10:72-74; Riether et al. (2015) Science Transl Med. 7:1-12; Zhou et al. (2011) Lupus 20:1365-1371, incorporated herein by reference). It follows, that azacitidine added to the combinations described herein, for example as a triple combination strategy, may serve to upregulate CD70 expression on target LSCs, thereby enhancing the efficacy of the CD70-LSC target double combination therapy.

In certain embodiments, the combinations described herein comprise an inhibitor of PD-1 (also known as "Programmed cell death protein 1" or "CD279"). Alternatively or in addition, the combinations described herein may comprise an inhibitor of PD-L1 or PD-L2 (ligands of PD-1).

PD-1 and its ligands, particularly PD-L1, have been relatively well-characterized as immune checkpoint regulators, and dysregulation of the PD-1-PD-L1 signaling pathway in the cancer microenvironment has been identified as an important means by which tumors suppress the immune response. The receptor PD-1 is typically expressed on a variety of immune cells including monocytes, T cells, B cells, dendritic cells and tumor-infiltrating lymphocytes, and the ligand PD-L1 has been found to be upregulated on a number of different types of tumor cell (see Ohaegbulam et al. (2015) Trends Mol Med. 21(1):24-33, incorporated herein by reference). The interaction between PD-L1 on tumor cells and PD-1 on immune cells, particularly T cells, creates an immunosuppressive tumor microenvironment via effects at the level of CD8+ cytotoxic T cells and also via the generation of Treg cells (see Alsaab et al. (2017) Front Pharmacol. Aug 23(8):561, incorporated herein by reference).

Without wishing to be bound by theory, combinations comprising or consisting of a CD70 antibody molecule, a TIM-3 antibody molecule and a PD-1 inhibitor or PD-L1 inhibitor are thought to be particularly effective for the treatment of malignancy, particularly myeloid malignancy, due to the combined actions of the active agents. As noted above, CD70 and TIM-3 are immune checkpoint targets, and therefore the combining of antibody molecules specifically binding to these targets with an agent or agents that inhibit a third immune checkpoint target may be particularly effective for the treatment of malignancy. It has also been shown, in a solid tumor model, that combined targeting of TIM-3 and PD-1 is a particularly effective therapeutic approach (Sakushi et al. 2010. J Exp Med. 207(10):2187-2194). It follows, that PD-1 and/or PD-L1 inhibitors added to the combinations described herein, for example as a triple combination strategy, may further enhance the efficacy of the CD7O-TIM3 double combination therapy.

The agent capable of inhibiting PD-1 or PD-L1 may be any suitable anti-cancer agent or inhibitor having specificity for PD-1, PD-L1 or the PD1-PD-L1 signaling axis. Many agents capable of inhibiting the activity of PD-1, PD-L1 or the PD1-PD-L1 signaling axis have been developed as reported for example, in Alsaab et al. (supra) (incorporated herein by reference), and any of these agents may be incorporated into the combinations of the present invention. In certain embodiments, the PD-1 and/or PD-L1 inhibitor may be an antibody molecule, for example a monoclonal antibody.

The PD-1 inhibitors for inclusion in the combinations described herein may be selected from the group including but not limited to: nivolumab; pembrolizumab; pidilizumab, REGN2810; AMP-224; MED10680; and PDR001. The PD-L1 inhibitors for inclusion in the combinations described herein may be selected from the group including but not limited to: atezolizumab; and avelumab.

In certain embodiments, the combinations of the invention comprise or consist of four active agents: (i) a first antibody molecule specifically binding CD70; (ii) a second antibody molecule specifically binding TIM-3; (iii) a hypomethylating agent; and (iv) an agent capable of inhibiting either PD-1 or PD-L1. The hypomethylating agent is preferably azacitidine. It will be understood that each of the four active agents may be selected from any of the specific embodiments described herein for each active agent.

The combinations described herein may further comprise one or more additional anti-cancer agents. In certain embodiments, the one or more additional anti-cancer agents are inhibitors of additional immune checkpoint targets.

For embodiments in accordance with the first aspect of the invention, the combinations may additionally comprise an agent that inhibits SIRPα signaling. Agents capable of inhibiting SIRPα signaling are described above in the context of combinations of the second aspect of the invention. Any of these agents may be included as an additional component of the combinations described in accordance with the first aspect of the invention. For embodiments wherein the agent that inhibits SIRPα signaling is a SIRPα antibody molecule fusion protein, the antibody molecule to which the SIRPα protein or domain thereof is linked is preferably an antibody molecule of the combination i.e. an antibody molecule that binds CD70 or an antibody molecule that binds a LSC target. In certain embodiments, the agent that inhibits SIRPα signaling is the immunoglobulin V-like domain of the SIRPα protein and at least one copy of this domain is fused to the CD70 antibody molecule of the combination.

In certain embodiments, the combinations of both the first and second aspects of the invention comprise one or more anti-cancer agents for use in the treatment of myeloid malignancies, for example one or more agents suitable for use in treating AML. Agents that may be incorporated into the combinations described herein include but are not limited to: Venetoclax; Vyxeos; Idhifa (or Enasidenib—an isocitrate dehydrogenase (IDH) inhibitor); and Rydapt (midostaurin—a FLT3 inhibitor). In certain embodiments, the combinations additionally comprise Venetoclax. In certain embodiments, the combinations additionally comprise Vyxeos.

Any of the combinations described herein can be packaged as a kit and optionally include instructions for use.

E. Methods of Treatment

The combination therapies as described herein are for use in methods of treating a malignancy in a human subject.

The present invention provides an antibody molecule that binds to CD70 for use in the treatment of a malignancy in a human subject, wherein the antibody molecule is administered in combination with a second antibody molecule that binds to a leukemic stem cell target. The present invention also provides an antibody molecule that binds to a leukemic stem cell target for use in the treatment of a malignancy in a human subject, wherein the antibody molecule is administered in combination with a second antibody molecule that binds to CD70. The invention also provides an antibody molecule that binds to CD70 for use in the treatment of malignancy in a human subject, wherein the antibody molecule is administered in combination with an agent that inhibits SIRPα signaling. The invention further provides an agent that inhibits SIRPα signaling for use in the treatment of malignancy in a human subject, wherein the agent is administered in combination with an antibody molecule that binds CD70.

The present invention further provides combinations in accordance with the first and second aspects of the invention for use in the treatment of a malignancy in a human subject. In a yet further aspect, the present invention provides a method for treating a malignancy in a human subject, said method comprising administering to the subject a combination in accordance with the first or second aspect of the invention. All embodiments described above in relation to the combinations of the first and second aspects of the invention are equally applicable to the methods described herein.

The term "malignancy" encompasses diseases in which abnormal cells proliferate in an uncontrolled manner and invade the surrounding tissues. Malignant cells that have entered the body's blood and lymph systems are capable of travelling to distal sites in the body and seeding at secondary locations.

In certain embodiment, the methods described herein are for treating malignancies comprising the production of cancer progenitor or stem cells expressing CD70, CD27, or both. As noted elsewhere herein, upregulated CD70 expression has been detected in different types of cancers including renal cell carcinomas, metastatic breast cancers, brain tumors, leukemias, lymphomas and nasopharyngeal carcinomas. Co-expression of CD70 and CD27 has also been detected in malignancies of the hematopoietic lineage including acute lymphoblastic lymphoma and T cell lymphoma. In certain embodiments, the methods described herein are for the treatment of any of the aforementioned malignancies associated with CD70 expression, CD27 expression or both.

In certain embodiment, the methods described herein are for treating malignancies comprising the production of cancer progenitor or stem cells expressing one or more the LSC targets to which an antibody molecule of the combination binds. For example, combinations comprising an antibody molecule that binds TIM-3 may be used to treat TIM-3-expressing malignancies. Combinations comprising an antibody molecule that binds CD47 may be used to treat CD47-expressing malignancies. Combinations comprising an antibody molecule that binds IL1RAP may be used to treat IL1RAP-expressing malignancies.

In particular embodiments, the methods described herein are for treating myeloid malignancies, wherein a myeloid malignancy refers to any clonal disease of hematopoietic stem or progenitor cells. The myeloid malignancy treated in accordance with the methods of the invention may be a newly diagnosed myeloid malignancy or a relapsed/refractory myeloid malignancy.

As described elsewhere herein, the combinations of the present invention are thought to be particularly effective for the treatment of myeloid malignancies, for the reason that CD70, TIM-3, the CD47-SIRPα axis and IL1 RAP have all been identified as key therapeutic targets in myeloid malignancies, particularly acute myeloid leukemia, see Kikushige et al. (2015) (supra), Riether et al. (2017) (supra), Theocharides et al. (2012) (supra), Ponce et al. (2017) (supra), Agerstam et al. (2015) (supra).

In certain embodiments, the myeloid malignancy is selected from: acute myeloid leukemia (AML); myelodysplastic syndromes (MDS); myeloproliferative neoplasms (MPN); chronic myeloid leukemia (CML); and chronic myelomonocytic leukemias (CMML). In preferred embodiments, the myeloid malignancy is acute myeloid leukemia (AML).

Myeloid malignancies can be categorized and diagnosed according to the World Health Organization (WHO) 2008 classification, taken in combination with the 2016 update to this classification, see in particular Arber et al. (2016) Blood 127(20):2391-2405, incorporated herein by reference.

Acute myeloid leukemia (AML) refers to hematopoietic neoplasms involving myeloid cells. AML is characterized by clonal proliferation of myeloid precursors with reduced differentiation capacity. AML patients exhibit an accumulation of blast cells in the bone marrow. Blast cells also accumulate in the peripheral blood of AML patients. Typically AML is diagnosed if the patient exhibits 20% or more blast cells in the bone marrow or peripheral blood.

According to the WHO classification, AML in general encompasses the following subtypes:

AML with recurrent genetic abnormalities; AML with myelodysplasia-related changes; therapy-related myeloid neoplasms; myeloid sarcoma; myeloid proliferations related to Down syndrome; blastic plasmacytoid dendritic cell neoplasm; and AML not otherwise categorized (e.g. acute megakaryoblastic leukemia, acute basophilic leukemia).

AML can also be categorized according to the French-American-British (FAB) classification, encompassing the subtypes: M0 (acute myeloblastic leukemia, minimally differentiated); M1 (acute myeloblastic leukemia, without maturation); M2 (acute myeloblastic leukemia, with granulocytic maturation); M3 (promyelocytic, or acute promyelocytic leukemia (APL)); M4 (acute myelomonocytic leukemia); M4eo (myelomonocytic together with bone marrow eosinophilia); M5 (acute monoblastic leukemia (M5a) or acute monocytic leukemia (M5b)); M6 (acute erythroid leukemias, including erythroleukemia (M6a) and very rare pure erythroid leukemia (M6b)); or M7 (acute megakaryoblastic leukemia).

As used herein, "AML" refers to any of the conditions encompassed by the WHO and/or FAB classifications, unless specified otherwise. Certain AML subtypes are considered to be of more favorable prognosis, some of intermediate prognosis and some of poor prognosis. The skilled person is aware of which subtypes would fall into which risk category.

Myelodysplastic syndrome (MDS) is characterized by dysplasia, cytopenia and/or abnormal changes in bone marrow cellularity and/or myeloid differentiation, for example increased blast cell infiltration. According to the WHO classification, MDS in general encompasses the following subtypes: MDS with single lineage dysplasia (previously called "refractory cytopenia with unilineage dysplasia", which includes refractory anemia, refractory neutropenia, and refractory thrombocytopenia); MDS with ring sideroblasts, which includes subgroups with single lineage dysplasia and multilineage dysplasia (previously called "refractory anemia with ring sideroblasts"); MDS with multilineage dysplasia (previously called "refractory cytopenia with multilineage dysplasia"); MDS with excess blasts (MDS-EB, previously called "refractory anemia with excess blasts"), which can be further subclassified into MDS-EB-1 and MDS-EB-2 based on blast percentages; MDS with isolated del(5q); and MDS, unclassified.

MDS can also be categorized according to the French-American-British (FAB) classification, encompassing the subtypes: M9980/3 (refractory anemia (RA)); M9982/3 (refractory anemia with ring sideroblasts (RARS)); M9983/3 (refractory anemia with excess blasts (RAEB)); M9984/3 (refractory anemia with excess blasts in transformation (RAEB-T)); and M9945/3 (chronic myelomonocytic leukemia (CMML)).

As used herein, "MDS" refers to any of the conditions encompassed by the WHO and/or FAB classifications, unless specified otherwise. For both AML and MDS, the WHO categorization is preferred herein.

Myeloproliferative neoplasms (MPN) are similar to MDS but according to the WHO classification, MPN in general encompasses the following subtypes: chronic myeloid leukemia (CML); chronic neutrophilic leukemia (CNL); polycythemia vera (PV); primary myelofibrosis (PMF); essential thrombocythemia (ET); chronic eosinophilic leukemia, not otherwise specified; and MPN unclassifiable.

Chronic myelomonocytic leukemia (CMML) and atypical chronic myeloid leukemia (aCML) fall within the category of MDS/MPN disorders according to the WHO classification, for the reason that they represent myeloid neoplasms with clinical, laboratory and morphologic features that overlap between MDS and MPN.

In certain embodiments, the methods described herein involve monitoring the patient's blast count i.e. the number of blast cells. As used herein, "blast cells" or "blasts" refer to myeloblasts or myeloid blasts which are the myeloid progenitor cells within the bone marrow. In healthy individuals, blasts are not found in the peripheral blood circulation and there should be less than 5% blast cells in the bone marrow. In subjects with myeloid malignancies, particularly AML and MDS, there is increased production of abnormal blasts with disrupted differentiation potential, and the overproduction of these abnormal blasts can be detected by monitoring the patient's blast count in the peripheral blood circulation or the bone marrow or both.

The proportion of blast cells in the bone marrow or peripheral blood can be assessed by methods known in the art, for example flow cytometric or cell morphologic assessment of cells obtained from a bone marrow biopsy of the subject, or a peripheral blood smear. The proportion of blasts is determined versus total cells in the sample. For example, flow cytometry can be used to determine the proportion of blast cells using the number of $CD45^{dim}$, $SSC^{low}$ cells relative to total cell number. By way of further example, cell morphological assessment can be used to determine the number of morphologically identified blasts relative to the total number of cells in the field of view being examined.

In certain embodiments are provided methods for reducing the proportion of blasts cells in the bone marrow to less than 25%, less than 20%, for example less than 10%. In certain embodiments are provided methods for reducing the proportion of blasts cells in the bone marrow to less than 5%. In certain embodiments are provided methods for reducing the proportion of blast cells in the bone marrow to between about 5% and about 25%, wherein the bone marrow blast cell percentage is also reduced by more than 50% as compared with the bone marrow blast cell percentage prior to performing the method (or pretreatment).

In certain embodiments are provided methods for reducing the proportion of blasts cells in the peripheral blood to less than 25%, less than 20%, for example less than 10%. In certain embodiments are provided methods for reducing the proportion of blasts cells in the peripheral blood to less than 5%. In certain embodiments are provided methods for reducing the proportion of blast cells in the peripheral blood to between about 5% and about 25%, wherein the peripheral blood blast cell percentage is also reduced by more than 50% as compared with the peripheral blast cell percentage prior to performing the method (or pretreatment).

For clinical determination of blast cell percentage, typically cell morphological (also known as cytomorphology) assessment is preferred.

In particular embodiments, the methods described herein induce a complete response. In the context of AML treatment, a complete response or "complete remission" is defined as: bone marrow blasts <5%; absence of circulating blasts and blasts with Auer rods; absence of extramedullary disease; ANC≥1.0×10$^9$/L (1000/μL); platelet count ≥100×10$^9$/L (100,000/μL), see Döhner et al. (2017) *Blood* 129(4): 424-447.

The methods may achieve a complete response with platelet recovery i.e. a response wherein the platelet count is >100×10$^9$/L (100,000/μL). The methods may achieve a complete response with neutrophil recovery i.e. a response wherein the neutrophil count is >1.0×10$^9$/L (1000/μL). Alternatively or in addition, the methods may induce a transfusion independence of red blood cells or platelets, or both, for 8 weeks or longer, 10 weeks or longer, 12 weeks or longer.

In particular embodiments, the methods described herein induce a minimal residual disease (or MRD) status that is negative.

In certain embodiments, the methods described herein induce a complete response without minimal residual disease ($CR_{MRD-}$), see Döhner et al. *ibid.*

The method may achieve a partial response or induce partial remission. In the context of AML treatment, a partial response or partial remission includes a decrease of the bone marrow blast percentage of 5% to 25% and a decrease of pretreatment bone marrow blast percentage by at least 50%, see Döhner et al. *ibid.*

The methods described herein may increase survival. The term "survival" as used herein may refer to overall survival, 1-year survival, 2-year survival, 5-year survival, event-free survival, progression-free survival. The methods described herein may increase survival as compared with the gold-standard treatment for the particular disease or condition to be treated. The gold-standard treatment may also be identified as the best practice, the standard of care, the standard medical care or standard therapy. For any given disease, there may be one or more gold-standard treatments depending on differing clinical practice, for example in different countries. The treatments already available for myeloid malignancies are varied and include chemotherapy, radiation therapy, stem cell transplant and certain targeted therapies. Furthermore, clinical guidelines in both the US and Europe govern the standard treatment of myeloid malignancies, for example AML; see O'Donnell et al. (2017) *Journal of the National Comprehensive Cancer Network* 15(7):926-957 and Döhner et al. (2017) Blood 129(4):424-447, both incorporated herein by reference.

The methods of the present invention may increase or improve survival relative to patients undergoing any of the standard treatments for myeloid malignancy.

The patients or subjects treated in accordance with the methods described herein, particularly those having AML, may have newly diagnosed disease, relapsed disease or primary refractory disease. A standard approach to treatment for newly diagnosed AML patients is the "standard 7+3 intensive chemotherapy" approach characterized by 7 days of high dose cytarabine followed by 3 days of anthracycline administration (e.g. daunorubicin or idarubicin). Intensive chemotherapy is given with the aim of inducing complete remission of AML, typically with the intention of the patient undergoing a stem cell transplant following successful chemotherapy.

Standard intensive chemotherapy is associated with significant toxicity and side-effects, meaning it is not suitable for patients unable to tolerate these effects. These patients are termed "ineligible for standard intensive chemotherapy". A patient may be ineligible for standard intensive chemotherapy because, for example, they exhibit one or more comorbidities indicating they would not tolerate the toxicity, or the prognostic factors characterizing their disease indicate an unfavorable outcome of standard intensive chemotherapy. Determination of an individual patient's eligibility for standard intensive chemotherapy would be performed by a clinician taking into account the individual patient's medical history and clinical guidelines (e.g. the National Comprehensive Cancer Network (NCCN) guidelines, incorporated herein by reference). AML patients over the age of 60 are often assessed as ineligible for standard intensive chemotherapy, with other factors to be considered including the cytogenetics and/or molecular abnormalities of the AML being treated.

A patient ineligible for standard intensive chemotherapy may instead receive chemotherapy of reduced intensity, such as low dose cytarabine (LDAC). Patients ineligible for standard intensive chemotherapy and for whom LDAC is not appropriate can receive best supportive care (BSC), including hydroxyurea (HU) and transfusion support.

Patients or subjects treated in accordance with the methods described herein may be those classified as "ineligible for standard intensive chemotherapy". The combinations of the invention comprise targeted therapies that may be predicted to have fewer side-effects. As such, patients deemed ineligible for standard intensive chemotherapy, for any of the reasons identified above, may be treated with the combinations according to the present invention.

The methods described herein may include a further step of subjecting the patient or subject to a bone marrow transplant. The methods described herein may also be used to prepare a patient or subject having a myeloid malignancy for a bone marrow transplant. As described above, the methods of the present invention may be carried out so as to reduce the absolute or relative numbers of blast cells in the bone marrow or peripheral blood. In certain embodiments, the methods are carried out so as to reduce the blast cell count in the bone marrow and/or peripheral blood prior to transplant. The methods may be used to reduce the blast cell count to less than 5% to prepare the patient or subject for a bone marrow transplant.

The methods described herein may include administration of further therapeutic agents, for example, further anti-cancer agents. In certain embodiments, the methods comprise the administration of one or more agents for use in treating myeloid malignancies, for example agents suitable for use in treating AML. Such agents include but are not limited to: Venetoclax; Vyxeos; Idhifa (or Enasidenib—an IDH inhibitor); and Rydapt (midostaurin—a FLT3 inhibitor).

Incorporation by Reference

Various patents, published patent applications, and publications are cited in the foregoing description and throughout the following examples, each of which is incorporated by reference herein in its entirety.

EXAMPLES

The invention will be further understood with reference to the following non-limiting examples.

Example 1

Antibodies specifically binding TIM-3 were generated by immunizing llama with recombinant human TIM-3 Fc chimera (R&D Systems; Human TIM-3 Ser22-Arg200; 2365-TM; Lot HKG081212A) at doses of 80 μg ($1^{st}$ and $2^{nd}$ injection) and 40 μg (injections 3-6) and creating Fab libraries for screening, as described in, for example, WO2010/001251, incorporated herein by reference.

The CDR, VH and VL sequences of the Fab clones selected from the libraries are shown in Tables 2, 3 and 4 below.

TABLE 2

VH and VL sequences of Fabs binding to TIM-3

| Fab clone | VH | SEQ ID NO: | VL | SEQ ID NO: |
|---|---|---|---|---|
| 1A11 | EVQLVESGGGLVQPGGSLRLSCAASGFTFSSYAMSWVRQAPGKGPEWVSHINSGGGNTKYADSVKGRFTISRDNAKNTLYLQMNTLKPEDTAVYYCAKDVSGGYYGTYALDAWGQGTQVVVSS | 9 | SYELTQSPSVSVALKQTAKITCGGDNIGSKSAQWYQQKPGQAPVLVIYADSRRPSGIPERFSGSNSGNTATLTISGAQAEDEADYYCQVWDSSAAVFGGGTHLTVL | 10 |
| 2A2 | EVQVQESGGGLVQPGGSLRLSCAASGFTFSSYAMSWVRQAPGKGLEWVSDINSGGGSTVYTDSVKGRFTISRDNAKNTLYLQMNSLKPDDTAVYYCATGGSYYSYRLFDYWGQGTQVTVSS | 11 | DIQMTQSPSSVIVSAGEKVTINCKSSQSVLDSSNQKNYLAWYQQRLGQSPRLLIYWASTRESGVPDRFSGSGSTTDFTLTISSFQPEDAAVYYCQQGYSVPVTFGQGTKVELKR | 12 |
| 2A6 | QVQLVESGGGLVQPGGSLRLSCAASGFTFSNYWMYWVRQAPGKGLEWVSTINTNGAITLYADNVKDRFTVSRDNAKNTLYLQMNSLKSEDTAVYYCAKVKLSGYPHPYYAMDYWGKGTLVTVSS | 13 | NFMLTQPPSLSGSLGQSARLTCTLGSGNSIGAHTISWYQQKAGSPPRYLLNYYSDSSNHQASGVPSRFSGSKDDSTNAGLLLISGLQPEDEADYYCAAGDGSGTVFGGGTKLTVL | 14 |
| 2A9 | QVQLVESGPGLVKPSQTLSLTCTVSGGSITTSDDAWSWIRQPAGKGLEWMGVIAYDGSTRYSPSLQSRTSISRDTSKNQFSLQLSSVTPEDTAVYYCARTKGVGGTWALDAWGQGTLVTVSS | 15 | EIVLTQSPSSVTASVGEKVTINCKSSQSVLSSSNQKNYLSWYQQRLGQSPRLLITWASTRESGVPDRFSGSGSTTDFTLTISSFQPEDAAVYYCQQGYGAPLTFGQGTKVELKR | 16 |
| 2B6 | QVQLVESGGGLVQPGGSLRLSCAASGFAFSSYDMSWVRQAPGKGLEWVSTINSGGGSTNYADSMKGRFTISRDNAKNTVYLQMNSLKPEDTAVYYCAARSPYYTRVPLYDYWGQGTQVTVSS | 17 | QAVVTQEPSLSVSLGGTVTLICGLRSGSVITSNYPGWFKQTPGQAPRTLIFGASSRHSGVPSRYSGSISGNKAALTITGAEPEDEADYYCALNKGTYTDVFGGGTKLTVL | 18 |
| 2B9 | EVQLQESGPGLVKPSQTLSLTCTVSGASVTTRYNYVVSWIRQPPGKGLEWMGAITYSGSTYYSPSLKSRTSISRDTSKNQFTLQLSSVTPEDTAVYYCATEGSSSTGVSRYSFGSWGQGTQVTVSS | 19 | ATMLTQSPGSLSVVPGESASISCKASQSLTHTDGTTALYWLQQKPGQRPQLLIYEVSVRASGVPDRFTGSGSGSDFTLKINGVKAEDAGVYYCAQVAYYPTFGQGTKVELK | 20 |
| 2B10 | QVQLQESGPGLVKPSQTLSLTCTVSGGSITTNRYLVVTWIRQTPGKGLEVVVGAIAYSGRTYYSPSLKSRTSISRDTSKNQFTLQLSSVTPEDTGVYYCAHFTGWGGYYWGQGTQVTVSS | 21 | QSALTQPPSVSGTLGKTVTISCAGTSSDIGGYNSVSVVYQQLPGTAPKLLIYEVNKRASGIPDRFSGSKSGNTASLSISGLQSEDEADYYCASYRSANNVVFGGGTKLTVL | 22 |
| 2C6 | QVQLVESGGGLVQPGGSLRLSCAASGFAFSSYDMSVVRQAPGKGPEVVVSTINSGGGSTSYADSVKGRFTISRDNAKNTVYLQMNSLKPEDTAVYYCAARSLYYTRVPMDYWGQGTQVTVSK | 23 | QAVVTQEPSLSVSPGGTVTLTCGLSSGSVTTNNYPGVVFQQTPGQAPRTLIYSTSSRHSGVPSRFSGSISGNKAALTITGAQPEDEADYYCALDIGSYTAVFGGGTHLTVL | 24 |
| 2D11 | EVQLVQPGAELRNPGASVKVSCKASGYTFTMYYIDVVVRQAPGQGLEWMGRIDPEDGGTKYAQKFQGRVTFTADTSTSTAYVELSSLRSEDTAVYYCARIPNGGSYYYTPYDYDYWGQGTQVTVSS | 25 | QAVVTQEPSLSVSPGGTVTLTCGLTSGSVTSSNYPGVVYRQTPGQAPRPLIYNTNSRHPGVPSRYSGSISENKATLTITGAEPEDEADYYCALHKGSYTAVFGGGTHLTVL | 26 |
| 2D6 | QVQLQESGGGLVQPGGSLTLSCAASGFFFSSYAMSVVRQAPGKGLEVVVSSISAGGGTSYYADSVKGRFTISRDSAKNTLVLQMNSLKPEDTAVYYCAKKRQNFWSEGYDSWGQGTQVTVSS | 27 | HSAVTQPPSVSGSPGKAVTISCVGSSSDVGYGDYVSVVYQQLPGMAPKWYDVEKRASGIPDRFSGSKSGNTASLTISGLQSEDEADYYCASYRSDSNFVFGGGTHLAVL | 28 |

TABLE 2-continued

VH and VL sequences of Fabs binding to TIM-3

| Fab clone | VH | SEQ ID NO: | VL | SEQ ID NO: |
|---|---|---|---|---|
| 2E2 | QLQLVESGGGLVQPGGSLRLSCAASGFTFGSYDMSVVRQAPGKGPEVVVSRITSGGGSTYADSVKGRFTISRDNAKNTLSLQMNSLKSEDTAVYYCAAGQYSDGYYPYDYWGQGTQVTVSS | 29 | DIVMTQSPSSLSASLGDRVTITCQASQSISSYLAVVYQQKPGQGPKLLIYGASRLEPGVPSRFSGSGSTSFTLTISGVEAEDLATYYCLQDYSWPYSFGSGTRLEIK | 30 |
| 2E7 | ELQVVESGGGLVQPGGSLRLSCAASGFTFGSYDMSWHRQAPRKGPEVVVSTISAGGGRTYYADSVKGRFTISRDNAKNTLYLQMNSLKPEDTAVYFCTKIVLDSWGQGTQVTVSS | 31 | DVVLTQTPGSLSVVPGESASISCKASQSLIHIDGKTYLYWLLQKPGRRPELLIYQVSNHESGVPDRFTGSGSGTDFTLKISGVKAEDAGVYYCAQATYYPSFGSGTRLEIK | 32 |
| 2E9 | EVQLVESGGGLVQPGGSLRLSCAASGFTFDDYTMSVVRQVPGKGLEWISGISGNGGRTDYVEPIEGRFTISRDNAKNTLYLQMNSLKSEDTAVYYCAKTSPQSLDYWGQGTQVTVSS | 33 | DIVMTQSPSSVTASVGEKVTINCKSSQSVVSGSNQKSYLNVVYQQRPGQPPRLLIYYASTQESGIPDRFSGSGSTTDFTLTISSVQPEDAAVYYCQQAYSAPYNFGSGTRLEIK | 34 |
| 2F8 | EVQLVESGGGLVQPGGSLRLSCAASGFTFGSYDMSVVRQAPGKGPEVVVSTISAGGGRTYYADSVKDRFTISRDNAKNTLYLQMNSLKPEDTAVYYCAKVVIDYWGQGTQVTVSS | 35 | DVVLTQTPGSLSVVPGESASISCKASQSLVHTDGKTYVYWLLQKPGQRPHLLIYQVSNHESGVPDRFTGSGSGTDFTLKISGVKAEDAGVYYCAQATYYPSFGSGTRLEIK | 36 |
| 2G6 | EVQLVESGGGLVQPGGSLRLSCAASGFTFSSYSMSVVRQAPGKGPEVVVSGINTSGGTTSYAASVKGRFTVSRDNAKNTLSLQMNSLEPEDTAVYYCVKHIRWSGSNYYYGMDYWGKGTLVTVSS | 37 | QAVLTQPPSVSGSPGQRFTISCTGSNRNIGNNYVNVVYQQLPGTAPKLLIYSDNLRTSGVPARFSASKSGTSSLTISGLQAEDEAVYYCSSWDDSLSGAVFGGGTHLTVL | 38 |

TABLE 3

Heavy chain CDR sequences of Fabs binding to TIM-3

| Fab clone | CDR1 | SEQ ID NO: | CDR2 | SEQ ID NO: | CDR3 | SEQ ID NO: |
|---|---|---|---|---|---|---|
| 1A11 | SYAMS | 39 | HINSGGGNTKYADSVKG | 40 | DVSGGYYGTYALDA | 41 |
| 2A2 | SYAMS | 39 | DINSGGGSTVYTDSVKG | 42 | GGSYYSYRLFDY | 43 |
| 2A6 | NYWMY | 44 | TINTNGAITLYADNVKD | 45 | VKLSGYPHPYYAMDY | 46 |
| 2A9 | TSDDAWS | 47 | VIAYDGSTRYSPSLQS | 48 | TKGVGGTWALDA | 49 |
| 2B6 | SYDMS | 50 | TINSGGGSTNYADSMKG | 51 | RSPYYTRVPLYDY | 52 |
| 2B9 | TRYNYWS | 53 | AITYSGSTYYSPSLKS | 54 | EGSSSTGVSRYSFGS | 55 |
| 21310 | TNRYLWT | 56 | AIAYSGRTYYSPSLKS | 57 | FTGWGGYY | 58 |
| 2C6 | SYDMS | 50 | TINSGGGSTSYADSVKG | 59 | RSLYYTRVPMYDY | 60 |
| 2D11 | MYYID | 61 | RIDPEDGGTKYAQKFQG | 62 | IPNGGSYYYTPYDYDY | 63 |
| 2D6 | SYAMS | 39 | SISAGGGTSYYADSVKG | 64 | KRQNFWSEGYDS | 65 |
| 2E2 | SYDMS | 50 | RITSGGGSTYADSVKG | 66 | GQYSDGYYPYDY | 67 |
| 2E7 | SYDMS | 50 | TISAGGGRTYYADSVKG | 68 | IVLDS | 69 |
| 2E9 | DYTMS | 70 | GISGNGGRTDYVEPIEG | 71 | TSPQSLDY | 72 |
| 2F8 | SYDMS | 50 | TISAGGGRTYYADSVKD | 73 | VVIDY | 74 |
| 2G6 | SYSMS | 75 | GINTSGGTTSYAASVKG | 76 | HIRWSGSNYYYGMDY | 77 |

TABLE 4

Light chain CDR sequences of Fabs binding to TIM-3

| Fab clone | CDR1 | SEQ ID NO: | CDR2 | SEQ ID NO: | CDR3 | SEQ ID NO: |
|---|---|---|---|---|---|---|
| 1A11 | GGDNIGSKSAQ | 78 | ADSRRPS | 79 | QVWDSSAAV | 80 |
| 2A2 | KSSQSVLDSSNQKNYLA | 81 | WASTRES | 82 | QQGYSVPVT | 83 |
| 2A6 | TLGSGNSIGAHTIS | 84 | YYSDSSNHQASGV | 85 | AAGDGSGTV | 86 |
| 2A9 | KSSQSVLSSSNQKNYLS | 87 | WASTRES | 82 | QQGYGAPLT | 88 |
| 2B6 | GLRSGSVTTSNYPG | 89 | GASSRHS | 90 | ALNKGTYTDV | 91 |

TABLE 4 -continued

Light chain CDR sequences of Fabs binding to TIM-3

| Fab clone | CDR1 | SEQ ID NO: | CDR2 | SEQ ID NO: | CDR3 | SEQ ID NO: |
|---|---|---|---|---|---|---|
| 2B9 | KASQSLTHTDGTTALY | 92 | EVSVRAS | 93 | AQVAYYPT | 94 |
| 2B10 | AGTSSDIGGYNSVS | 95 | EVNKRAS | 96 | ASYRSANNVV | 97 |
| 2C6 | GLSSGSVTTNNYPG | 98 | STSSRHS | 99 | ALDIGSYTAV | 100 |
| 2D11 | GLTSGSVTSSNYPG | 101 | NTNSRHP | 102 | ALHKGSYTAV | 103 |
| 2D6 | VGSSSDVGYGDYVS | 104 | DVEKRAS | 105 | ASYRSDSNFV | 106 |
| 2E2 | QASQSISSYLA | 107 | GASRLEP | 108 | LQDYSWPYS | 109 |
| 2E7 | KASQSLIHIDGKTYLY | 110 | QVSNHES | 111 | AQATYYPS | 112 |
| 2E9 | KSSQSVVSGSNQKSYLN | 113 | YASTQES | 114 | QQAYSAPYN | 115 |
| 2F8 | KASQSLVHTDGKTYVY | 116 | QVSNHES | 111 | AQATYYPS | 117 |
| 2G6 | TGSNRNIGNNYVN | 118 | SDNLRTS | 119 | SSWDDSLSGAV | 120 |

The Fabs shown in the tables above were characterized with respect to their TIM-3 binding by Biacore analysis and by ELISA. The results are shown in Table 5 below.

TABLE 5

Binding of Fab clones to TIM-3 as measured by Biacore or ELISA.

| Fab clone | Off-rate KD (1/s) | EC50 (ng/ml) |
|---|---|---|
| 2G6 | 3.72E-05 | 13.3 |
| 2D11 | very high | n/a |
| 2A6 | 1.51E-04 | 10.36 |
| 2B9 | 4.87E-05 | 8.505 |
| 1A11 | 2.48E-05 | 10.05 |
| 2C6 | 1.04E-05 | 8.212 |
| 2B6 | 3.64E-05 | 8.518 |
| 2D6 | 1.66E-04 | 7.169 |
| 2E2 | very high | 121.1 |
| 2A9 | high | 11.39 |
| 2A2 | 4.41E-05 | 8.047 |
| 2B10 | 1.85E-05 | 14.01 |
| 2E9 | 6.64E-05 | 14.86 |
| 2E7 | 7.62E-05 | 13.29 |
| 2F8 | 8.53E-05 | 18.07 |

Example 2

Antibodies specifically binding IL1RAP were generated by immunizing llama with recombinant human IL-1RAP/IL-1 R3 Fc Chimera Protein (R&D Systems: Ser21 Glu359/C-terminus HIS-tagged; Cat No. 676-CP) and creating Fab libraries for screening, as described in, for example, WO2010/001251, incorporated herein by reference.

The CDR, VH and VL sequences of the Fab clones selected from the libraries are shown in Tables 6, 7 and 8 below.

TABLE 6

VH and VL sequences of Fabs binding to IL1RAP

| Fab clone | VH | SEQ ID NO: | VL | SEQ ID NO: |
|---|---|---|---|---|
| 1F10 | QVQLVESGGGLVQPGGSL RLSCAASGFIFINYGMHW VRQAPGKGLEWVSAVNSG GASTDYADSVKGRFTISR DDAKNTLYLQMNSLKSED TAVYYCVKGWFYGIHYWG KGTLVTVSS | 121 | QAVLTQLPSVSGSPGQK ITISCTGSSSNIGGGYS VQWFQHLPGTPPKLLIY GNSNRASGVPDRFSGSK SGSSASLTITGLQAEDE ADYYCESYDDWLKGRGF GGGSKLTVL | 122 |
| 1C1 | QVQLVESGPGLVKPSQTL SLTCTVSGGSITTNYYSW IWIRQPPGKGLEWMGASV YSGSTFYSPSLKNTSISK DTAQNQFTLQLRSVTPED TAVYYCARASSAHWGSSF ISIDYWGQGTQVTVSS | 123 | QSVLTQPPSVSGSPGKT VTISCAGTSSDVGYGNY VSWYQQLPGMAPKWYDV DIRASGIADRFSGSKSG NTASLTISGLQSEDEAD YYCASYRTNNNAVFGGG THLTVL | 124 |

TABLE 7

Heavy chain CDR sequences of Fabs binding to IL1RAP

| Fab clone | CDR1 | SEQ ID NO: | CDR2 | SEQ ID NO: | CDR3 | SEQ ID NO: |
|---|---|---|---|---|---|---|
| 1F10 | NYGMH | 125 | AVNSGGASTDYADSVKG | 126 | GWFYGIHY | 127 |
| 1C1 | TNYYSWI | 128 | ASVYSGSTFYSPSLKN | 129 | ASSAHWGS SFISIDY | 130 |

TABLE 8

Light chain CDR sequences of Fabs binding to IL1RAP

| Fab clone | CDR1 | SEQ ID NO: | CDR2 | SEQ ID NO: | CDR3 | SEQ ID NO: |
|---|---|---|---|---|---|---|
| 1F10 | TGSSSNIGGGYSVQ | 131 | GNSNRAS | 132 | ESYDDWLKGRG | 133 |
| 1C1 | AGTSSDVGYGNYVS | 134 | DVDIRAS | 135 | ASYRTNNNAV | 136 |

Example 3

Combined Efficacy of Anti-TIM-3 and Anti-CD70 Antibodies Measured by ADCP Activity The combined efficacy of anti-TIM-3 and anti-CD70 antibodies was assessed by measuring antibody-dependent cellular phagocytosis (ADCP)-mediated killing of the AML-derived cell line BDCM. BDCM cells with PKH26-labelled cell membranes were treated with different concentrations of the CD70-targeting antibody ARGX-110 alone or in combination with 10 μg/ml of the anti-TIM-3 antibodies clones 1A11 and 2B10 (human IgG1) — see Example 1. Phagocytosis-capable macrophages were differentiated from monocytic THP-1 cell line by PMA treatment. Activated macrophages were added to the BDCM cells pre-treated with antibodies and co-incubated with the cancer cells for one hour at 37° C. After washing, macrophages were stained with anti-CD11b-FITC antibodies and flow cytometry analysis was performed in order to estimate the number of macrophages with engulfed cancer cells (PKH26$^+$/CD11b$^+$ double positive macrophages).

As shown in FIG. 1, pre-treatment of CD70 and TIM-3-expressing BDCM cells with ARGX-110 and anti-TIM3 antibodies caused a significant increase in phagocytosis of cancer cells by macrophages. This increase was seen in comparison to the treatment of cells with ARGX-110 alone. The combined efficacy of anti-TIM3 and anti-CD70 antibodies in ADCP-mediated killing of AML cells was shown in a dose-dependent manner.

Example 4

Figure 2:
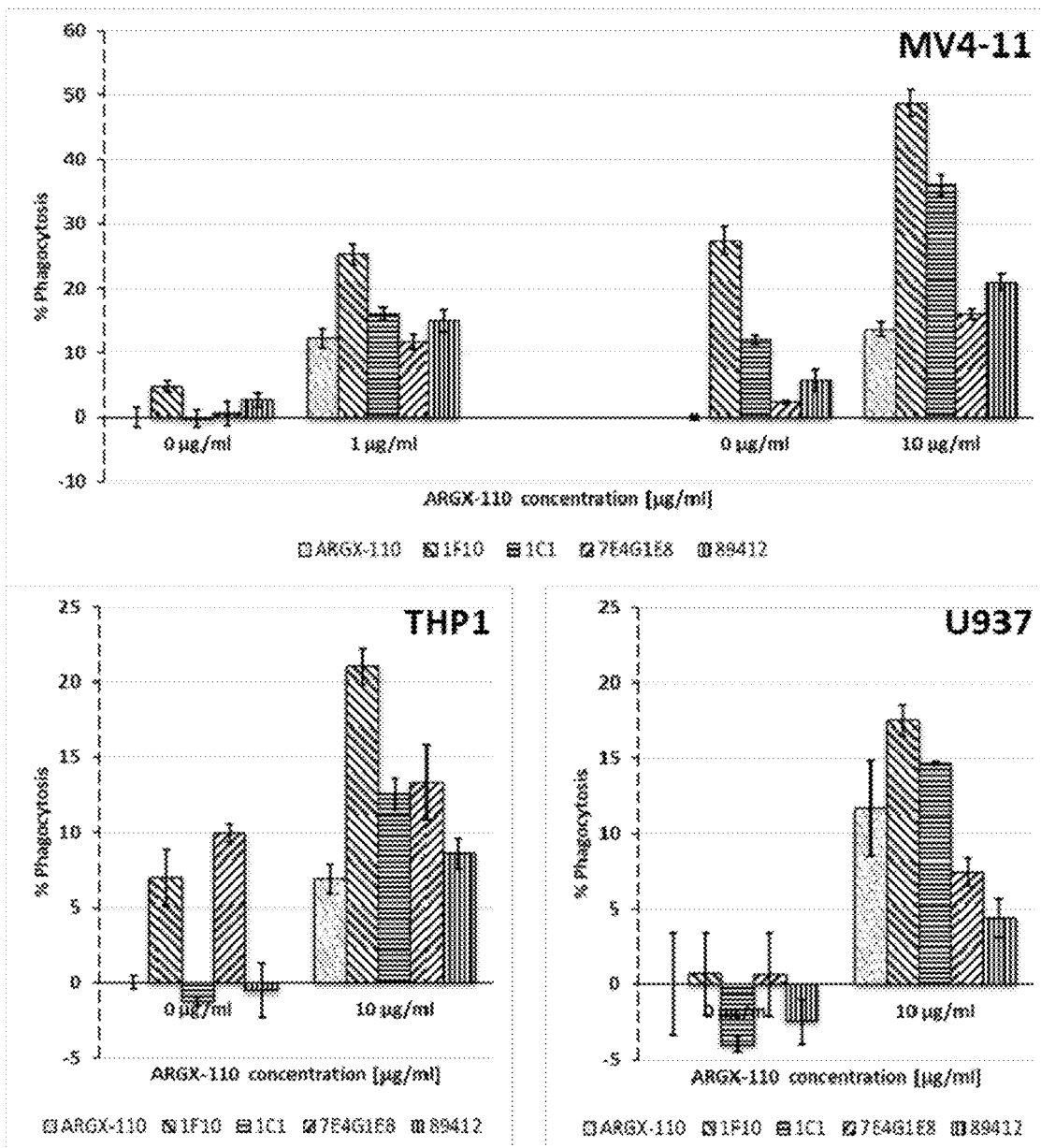
FIG. 2 shows the combined efficacy of an anti-CD70 antibody (ARGX-110) and anti-IL1RAP antibodies (1F10, 1C1, 7E4G1E8 and 89412) in mediating antibody-dependent cellular phagocytosis (ADCP) against AML cell lines (MV4-11, THP1 and U937).

Combined Efficacy of Anti-IL1RAP and Anti-CD70 Antibodies Measured by ADCP Activity The combined efficacy of anti-IL1RAP and anti-CD70 antibodies was assessed by measuring antibody-dependent cellular phagocytosis (ADCP)-mediated killing of AML cell lines (MV4-11, U937 and THP-1). PKH126-stained AML cell lines (MV4-11, U937, THP-1) were treated with different concentrations of ARGX-110 alone or in combination with 10 µg/ml or 1 µg/ml anti-IL1RAP antibodies (mouse IgG1 clone 89412; IgG2a clone 7E4G1E8 mAbs; and human monoclonal IgG1 antibodies-clones 1C1 and 1F10, see Example 2). The assay was performed as described in Example 3 above. The results are shown in FIG. 2. Phagocytosis background values, measured in the absence of any treatment, have been subtracted.

As shown in FIG. 2, pre-treatment of CD70- and IL1RAP-expressing AML cell lines with ARGX-110 and anti-IL1RAP antibodies caused significant increases in phagocytosis of cancer cells by macrophages. These increases were seen in comparison with conditions where cancer cells were only treated with ARGX-110. Additive effects of co-treatment were shown in a dose-dependent manner. Moreover, synergistic efficacy was observed when MV4-11 cells were treated with combinations of 1 or 10 µg/ml ARGX-110 plus 1C1 or 1F10 antibodies.

Example 5

Combined Efficacy of Anti-CD47 and Anti-CD70 Antibodies Measured by ADCP Activity The combined efficacy of anti-CD47 and anti-CD70 antibodies was assessed in a similar manner to that described above in Examples 3 and 4. PKH126-stained AML cell lines (MV4-11, THP-1, GDM-1, U937 and MC-1010) were treated with different concentrations of ARGX-110 alone or in combination with 10 µg/ml or 1 µg/ml of anti-CD47 antibodies (mouse IgG1 clone B6H12 and clone CC2C6, and mouse IgG2b clone BRIC126). The ADCP assay was performed as described above.

Figure 3A:
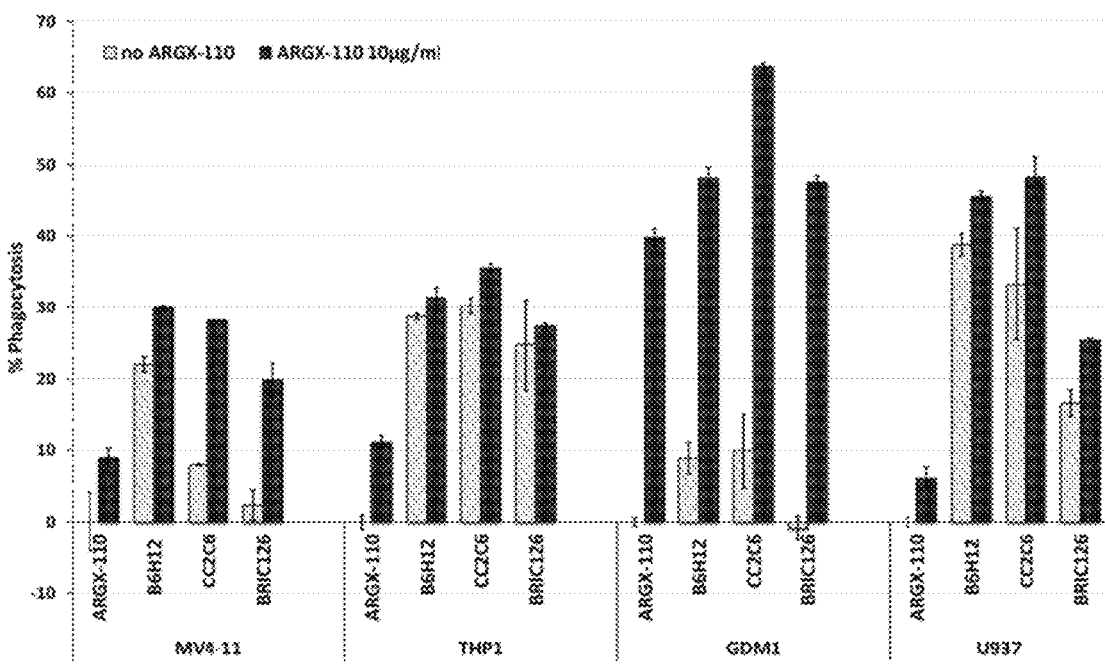
FIGS. 3A and 3B show the combined efficacy of an anti-CD70 antibody (ARGX-110) and anti-CD47 antibodies (B6H12, CC2C6 and BRIC126) in mediating antibody-dependent cellular phagocytosis (ADCP) against AML cell lines (MC1010, MV4-11, THP1, GDM1 and U937).
Figure 3B:
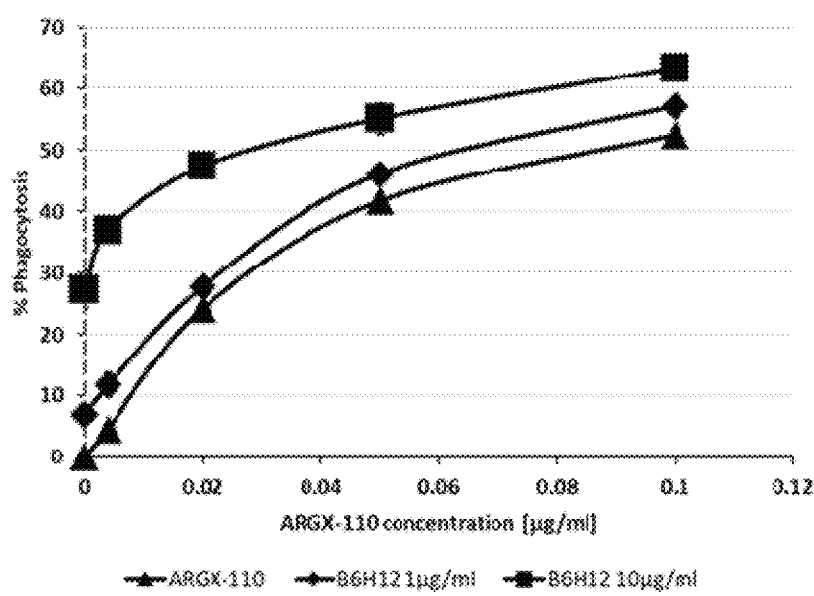

As shown in FIG. 3A, pre-treatment of CD70- and CD47-expressing AML cells with ARGX-110 and anti-CD47 antibodies caused increases in phagocytosis of cancer cells by macrophages in the case of several of the AML cell lines. The effect of co-treatment with ARGX-110 and blocking B6H12 antibody (which blocks the interaction between CD47 and SIRPα, thereby promoting phagocytosis) was also shown in a dose-dependent manner using MC-1010 cells (FIG. 3B).

Example 6

Figure 4:
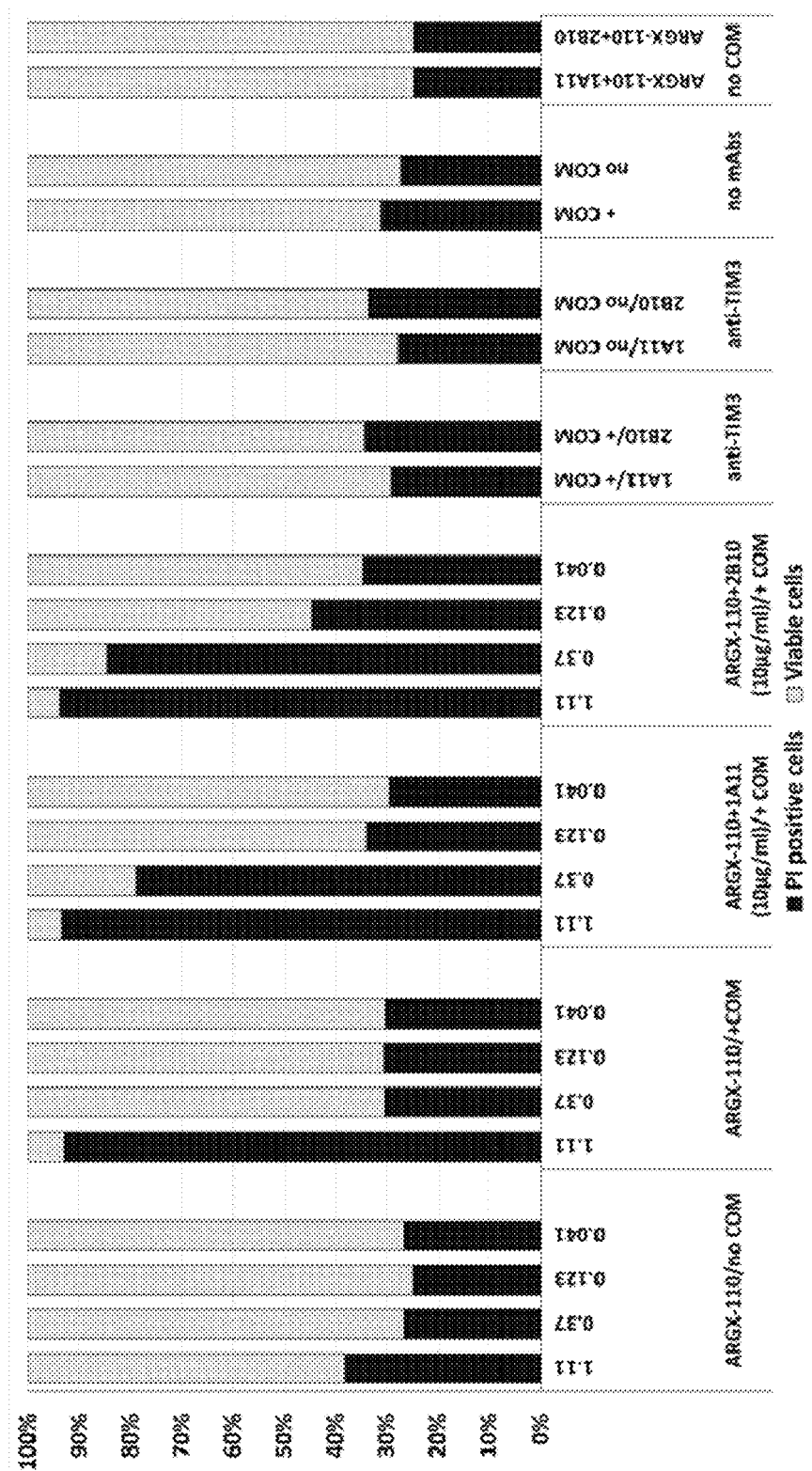
FIG. 4 shows the combined efficacy of an anti-CD70 antibody (ARGX-110) and anti-TIM-3 antibodies (1A11 and 2B10) in mediating complement-mediated cytotoxicity (CDC).

Combined Efficacy of Anti-TIM-3 and Anti-CD70 Antibodies Measured by CDC Activity The combined efficacy of anti-TIM-3 and anti-CD70 antibodies was assessed by measuring complement-dependent cytotoxicity (CDC). BDCM cells were treated with different concentrations of ARGX-110 alone or in combination with 10 µg/ml of anti-TIM-3 antibodies (1A11 and 2610 clones—see Example 1). Pre-treated cells were incubated with 10% baby rabbit complement (COM) for one hour at room temperature. One volume of PBS with propidium iodide (PI) was added and samples were incubated in the dark for fifteen minutes to stain dead cells. Determination of cell number and propidium iodide positive cells was performed by flow cytometry (FACS Canto II). The results are shown in FIG. 4.

Co-treatment of BDCM cells with ARGX-110 and anti-TIM3 antibodies caused an increase in complement-dependent cell death. Synergistic effects of the combinations of ARGX-110 and anti-TIM-3 antibodies were observed at concentrations of ARGX-110 between 0.37 and 0.125 µg/ml, whereas ARGX-110 alone was able to induce the cell death from 1.11 µg/ml concentration. These synergistic effects of the co-treatment were shown in a dose-dependent manner. Neither of the anti-TIM-3 antibodies were able to cause complement-dependent lysis when they were used alone in the assay.

Example 7

Figure 5A:
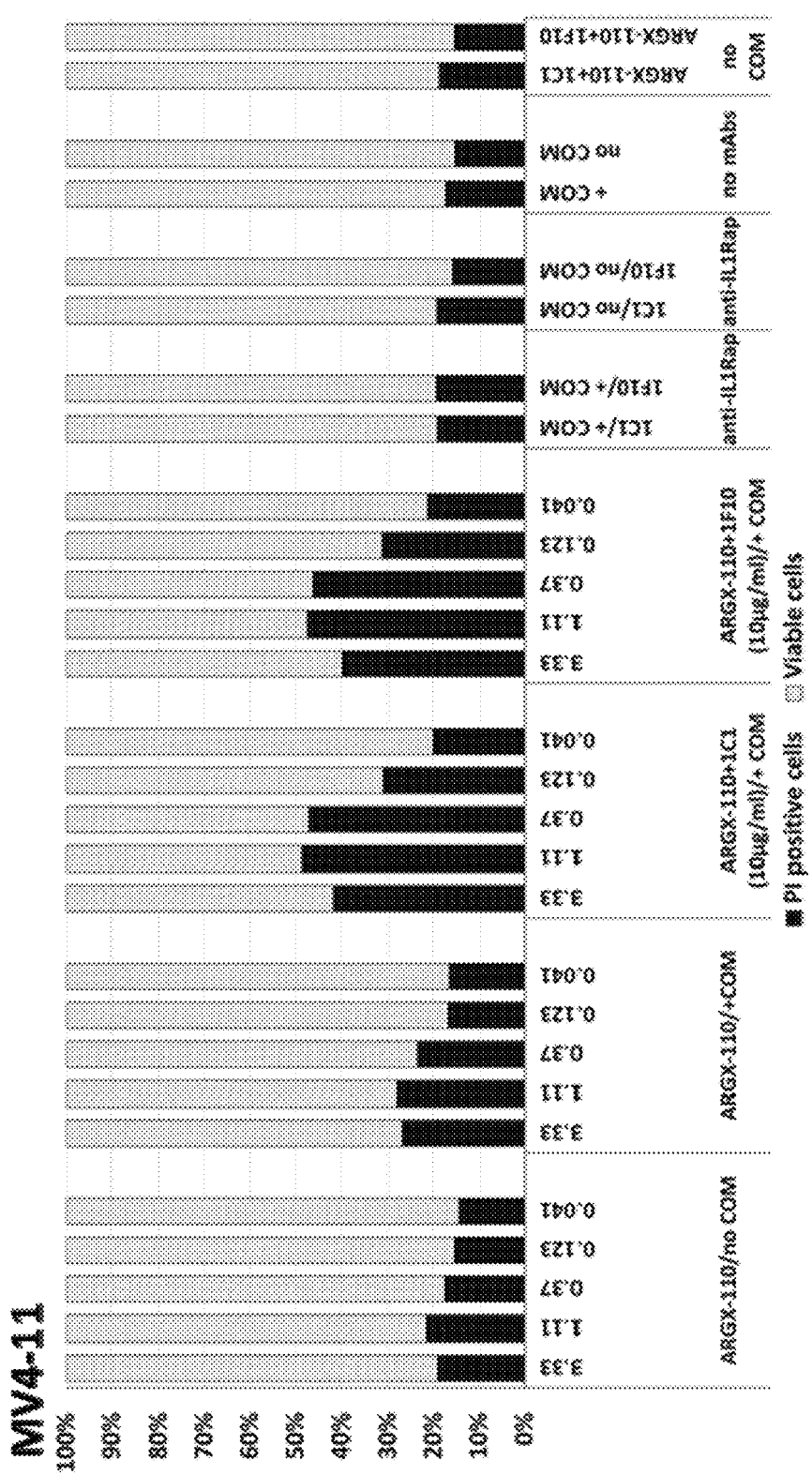
FIGS. 5A and 5B show the combined efficacy of an anti-CD70 antibody (ARGX-110) and anti-IL1RAP antibodies (1F10 and 1C1) in mediating complement-mediated cytotoxicity (CDC).
Figure 5B:
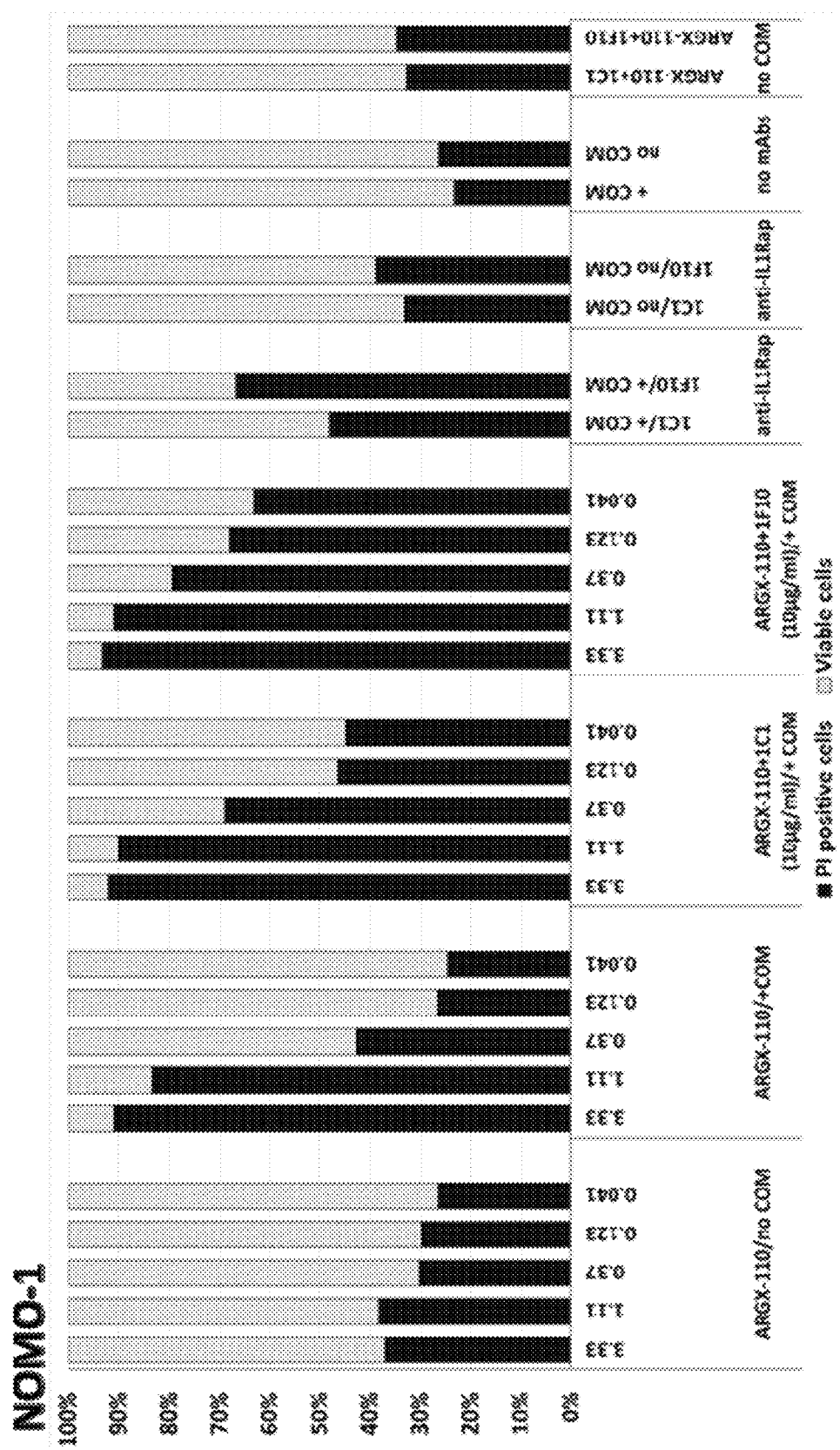

Combined Efficacy of Anti-IL1RAP and Anti-CD70 Antibodies Measured by CDC Activity The combined efficacy of anti-IL1RAP and anti-CD70 antibodies was assessed by measuring complement-dependent cytotoxicity (CDC). AML cell lines (MV4-11 and NOMO-1) were treated with different concentrations of ARGX-110 alone or in combination with 10 µg/ml of anti-IL1RAP antibodies (1C1 and 1F10 clones) and CDC assay was performed as described in Example 6. The results are shown in FIG. 5.

Co-treatment with ARGX-110 and anti-IL1RAP antibodies increased the complement-dependent cell death (FIG. 5, dark bars) of both cell lines. The MV4-11 cell line was resistant to the treatment with ARGX-110 and anti-IL1RAP alone. However, a synergistic effect was observed with the co-treatment, causing lysis of MV4-11 cells in a dose-dependent manner. ARGX-110-sensitive cell line NOMO-1 showed a dose-dependent effect after co-treatment with ARGX-110 and anti-IL1RAP antibodies in comparison with treatment with ARGX-110 alone. In the case of NOMO-1 cells, monotherapy with anti-IL1RAP antibodies induced a limited complement-dependent cytotoxicity when the antibodies were used at 10 µg/ml concentration.

Example 8

Figure 6A:
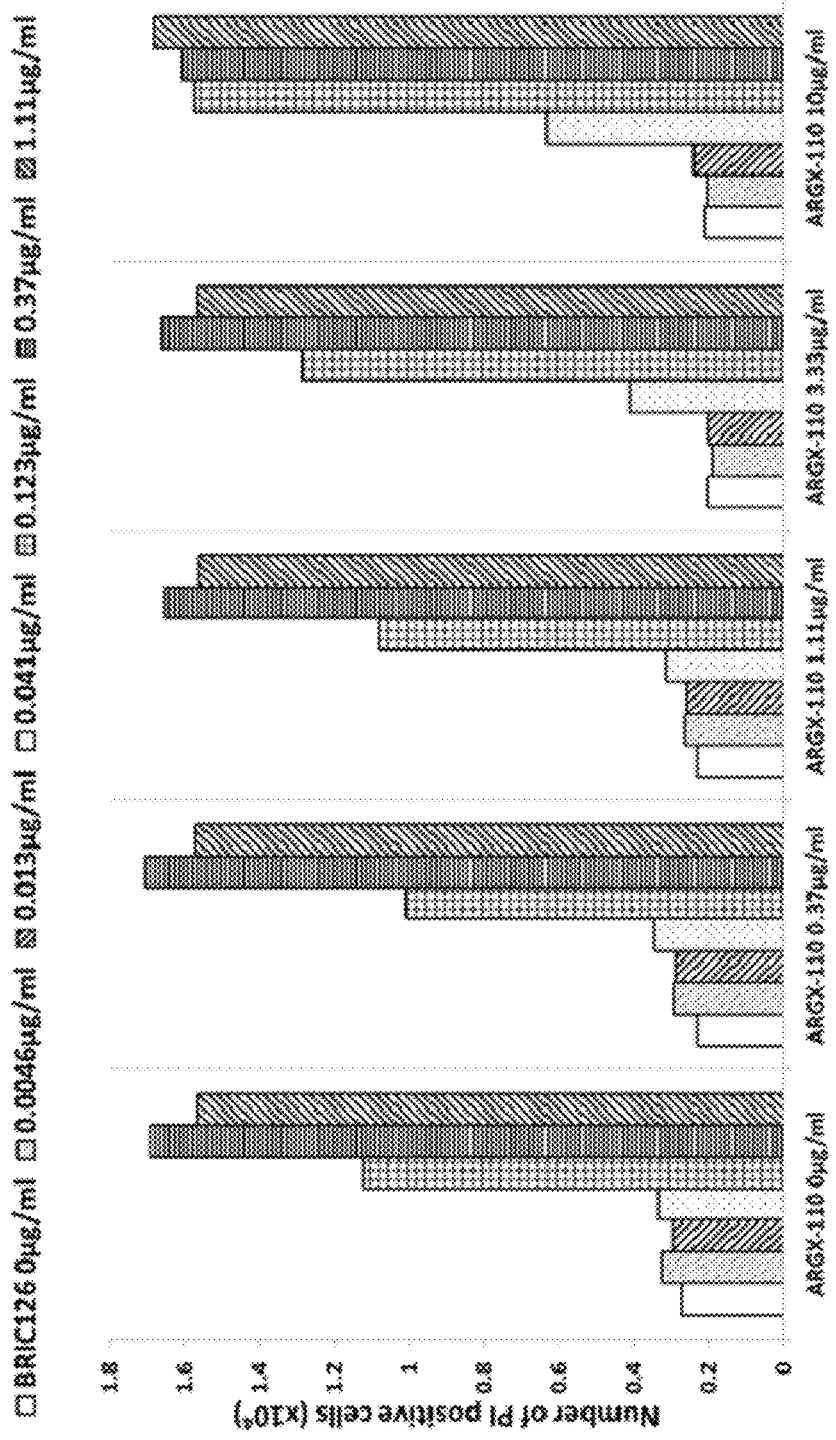
FIGS. 6A and 6B show the combined efficacy of an anti-CD70 antibody (ARGX-110) and an anti-CD47 antibody (BRIC126) in mediating complement-mediated cytotoxicity (CDC).
Figure 6B:
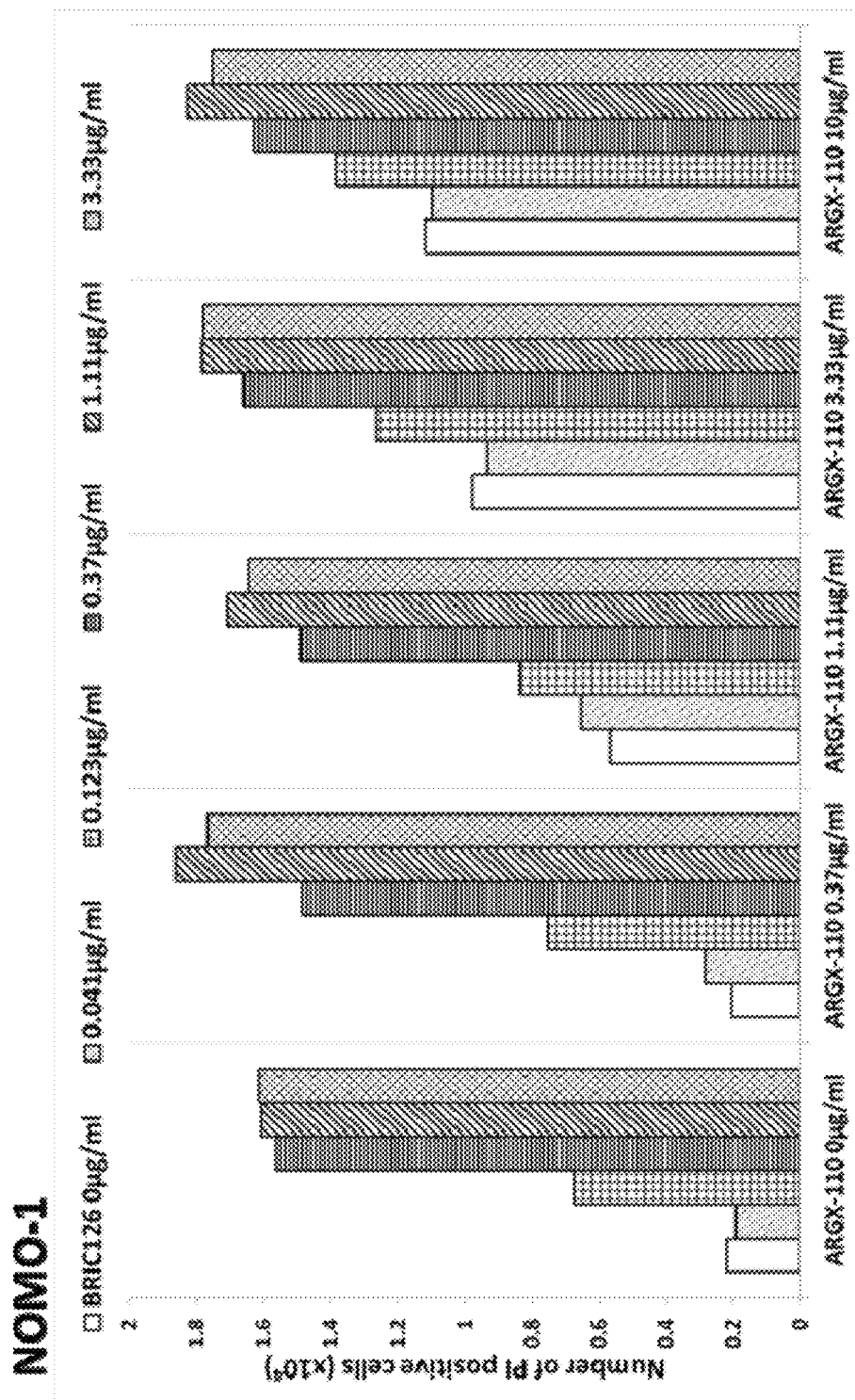

Combined Efficacy of Anti-CD47 and Anti-CD70 Antibodies Measured by CDC Activity The combined efficacy of anti-CD47 and anti-CD70 antibodies was assessed by measuring complement-dependent cytotoxicity (CDC). MV4-11 and NOMO-1 cell lines were treated with different concentrations of ARGX-110 and CDC-capable anti-CD47 antibody BRIC126 (mouse IgG2b) alone or in combinations. The CDC assay was performed as described above. The results are shown in FIG. 6.

Co-treatment of the AML cell lines with ARGX-110 and BRIC126 increased the complement-dependent cell death in both cell lines, whereas an anti-CD47 blocking mouse IgG1 antibody was not able to induce complement response (B6H12 clone) (data not shown). The effect of co-treatment with ARGX-110 and BRIC126 was observed in a dose-dependent manner with an optimal concentration of BRIC126 between 0.041 and 0.123 µg/ml. The MV4-11 cell line is only weakly responsive to ARGX-110 and therefore as high as 10 µg/ml concentration was needed to obtain a combined effect. In the ARGX-110-sensitive cell line, NOMO-1, the cells were lysed by complement at a ten times lower concentration of ARGX-110 alone. Furthermore, adding BRIC126, at about 0.1 µg/ml, further augmented cell lysis by complement. Monotherapy with BRIC126 at higher concentrations was also able to induce complement-dependent cytotoxicity.

Example 9

Combined Efficacy of Anti-TIM-3, Anti-IL1RAP or Anti-CD47 Antibodies and Anti-CD70 Antibodies Measured by ADCC Activity The efficacy of the anti-CD70 antibody ARGX-110 in combination with either anti-TIM-3 antibodies, anti-IL1RAP antibodies or anti-CD47 antibodies was measured by antibody-dependent cellular cytotoxicity (ADCC). The ADCC activity of the following antibody combinations was investigated:
1. ARGX-110 (anti-CD70) and 2610 (anti-TIM-3)
2. ARGX-110 (anti-CD70) and 1F10 (anti-IL1RAP)
3. ARGX-110 (anti-CD70) and CC2C6 (anti-CD47)

For all combinations tested, ADCC was measured according to the following protocol. Healthy peripheral blood mononuclear cells (PBMCs) were treated with recombinant IL-2 (200 IU/mL) for 15 hours. Cell lines BDCM and NOMO-1 were used as CD70-positive target cells, also expressing CD47 and TIM-3 or IL1RAP1 respectively. Target cells (3E4 cells) were co-cultured with PBMCs (3E5cells) in the presence of antibodies in RPMI 1640 medium with 10% FCS (96-well plate). The effector/target (E/T) ratio was 1/1. A dilution series of ARGX-110 (0-10 µg/mL) alone or in combination with the antibodies 2B10 (anti-TIM-3), 1F10 (anti-IL1RAP) or CC2C6 (anti-CD47) at a concentration of 10 and 1 µg/mL were applied. All antibodies except CC2C6 (mouse IgG1) were human IgG1 isotype. After 48 hours of incubation, the cells were analyzed by flow cytometry and the % lysis was measured based on the number of target cells ($CD33^+$ $CD3^-$ $CD16^-$) remaining. The results are shown in FIGS. 7 (anti-CD70 + anti-TIM-3), 8 (anti-CD70 + anti-IL1RAP) and 9 (anti-CD70+ anti-CD47).

Figure 7:
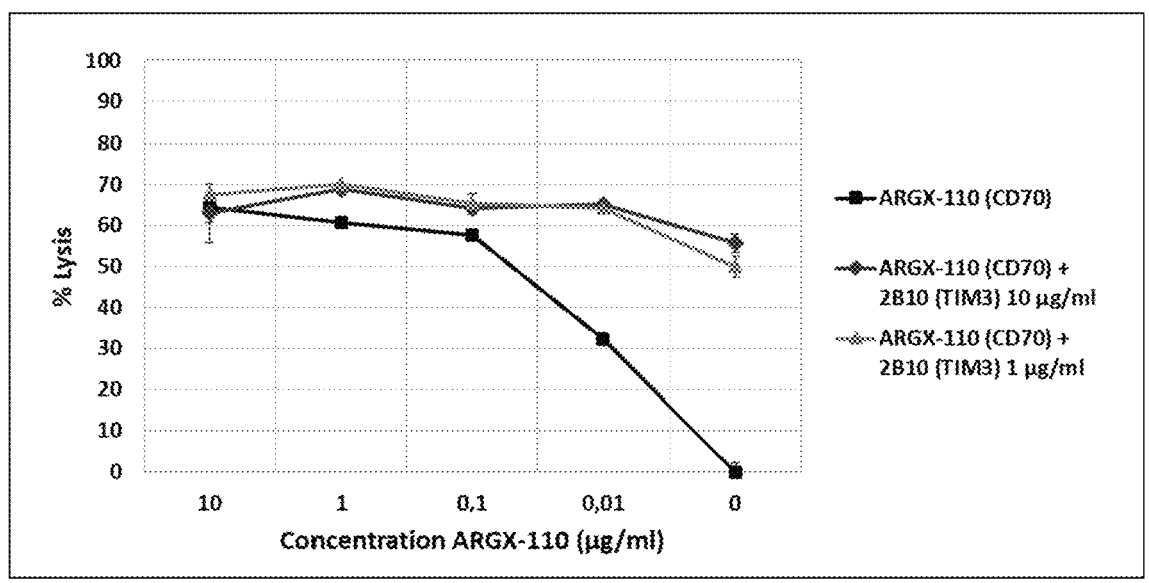
FIG. 7 shows the combined efficacy of an anti-CD70 antibody (ARGX-110) and an anti-TIM-3 antibody (2B10) in mediating antibody-dependent cellular cytotoxicity (ADCC) against a BDCM cell line.

As shown in FIG. 7, both anti-CD70 and anti-TIM-3 antibodies showed strong ADCC activity alone and reached a maximum cell lysis of 50-70% at a concentration of 1 µg/mL or higher. A combined activity was observed at lower concentration of ARGX-110 (<0.1 µg/ml).

Figure 8:
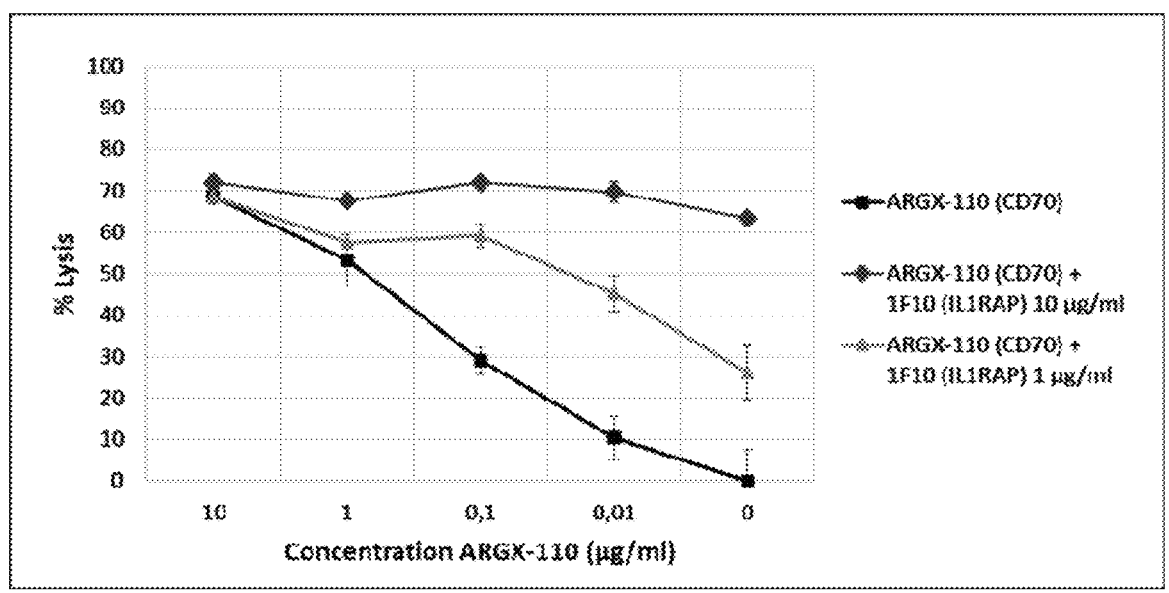
FIG. 8 shows the combined efficacy of an anti-CD70 antibody (ARGX-110) and an anti-IL1RAP antibody (1F10) in mediating antibody-dependent cellular cytotoxicity (ADCC) against an AML cell line (NOMO-1).

As shown in FIG. 8, a combined ADCC activity was achieved across the ARGX-110 dose range when combined with the anti-IL1RAP antibody 1F10 at 1 µg/ml. This combination reached a maximum cell lysis of 70% at the highest ARGX-110 concentration tested (10 µg/ml). The anti-IL1RAP antibody 1F10 showed a strong ADCC activity alone at 10 µg/ml which resulted in 60-70% cell lysis.

Figure 9:
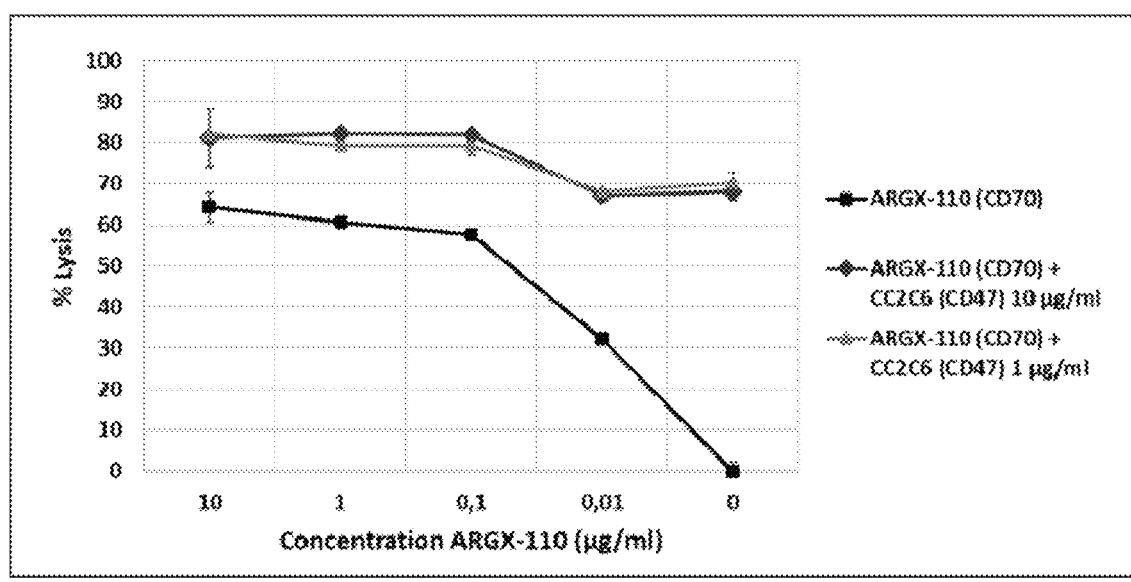
FIG. 9 shows the combined efficacy of an anti-CD70 antibody (ARGX-110) and an anti-CD47 antibody (CC2C6) in mediating antibody-dependent cellular cytotoxicity (ADCC) against an AML cell line (NOMO-1).

As shown in FIG. 9, combined ADCC activity was achieved across the ARGX-110 dose range when combined with anti-CD47 antibody CC2C6 at 1 or 10 µg/ml. This combination reached a maximum cell lysis of 80% at 0.1 µg/mL or higher concentrations of ARGX-110.

The invention claimed is:

1. A combination comprising a first antibody molecule that specifically binds to CD70 and a second antibody molecule that specifically binds to TIM-3,
wherein the first antibody molecule comprises a first variable heavy chain domain (VH) comprising HCDR1, HCDR2 and HCDR3 regions, and a first variable light chain domain (VL) comprising LCDR1, LCDR2 and LCDR3 regions, wherein the HCDR1, HCDR2, HCDR3, LCDR1, LCDR2 and LCDR3 regions of the first VH and the first VL comprise the amino acid sequences set forth in SEQ ID NOs: 1 2, 3, 5, 6, and 7, respectively, and
wherein the second antibody molecule comprises a second VH comprising HCDR1, HCDR2 and HCDR3 regions, and a second VL comprising LCDR1, LCDR2 and LCDR3 regions, wherein the HCDR1, HCDR2, HCDR3, LCDR1, LCDR2 and LCDR3 regions of the second VH and the second VL comprise:
(i) SEQ ID NOs: 39, 40, 41, 78, 79, and 80, respectively;
(ii) SEQ ID NOs: 39, 42, 43, 81, 82, and 83, respectively;
(iii) SEQ ID NOs: 44, 45, 46, 84, 85, and 86, respectively;
(iv) SEQ ID NOs: 47, 48, 49, 87, 82, and 88, respectively;
(v) SEQ ID NOs: 50, 51, 52, 89, 90, and 91, respectively;
(vi) SEQ ID NOs: 53, 54, 55, 92, 93, and 94, respectively;
(vii) SEQ ID NOs: 56, 57, 58, 95, 96, and 97, respectively;
(viii) SEQ ID NOs: 50, 59, 60, 98, 99, and 100, respectively;
(ix) SEQ ID NOs: 61, 62, 63, 101, 102, and 103, respectively;
(x) SEQ ID NOs: 39, 64, 65, 104, 105, and 106, respectively;
(xi) SEQ ID NOs: 50, 66, 67, 107, 108, and 109, respectively;
(xii) SEQ ID NOs: 50, 68, 69, 110, 111, and 112, respectively;
(xiii) SEQ ID NOs: 70, 71, 72, 113, 114, and 115, respectively;
(xiv) SEQ ID NOs: 50, 73, 74, 116, 111, and 117, respectively; or
(xv) SEQ ID NOs: 75, 76, 77, 118, 119, and 120, respectively.

2. The combination of claim 1, wherein the first VH comprises an amino acid sequence at least 70% identical to the amino acid sequence of SEQ ID NO: and the first VL comprises an amino acid sequence at least 70% identical to the amino acid sequence of SEQ ID NO: 8.

3. The combination of claim 2, wherein the first antibody molecule is ARGX-110.

4. The combination of claim 1, wherein the second antibody molecule inhibits the interaction of TIM-3 with one or more TIM-3 interacting moieties.

5. The combination of claim 4, wherein the TIM-3 interacting moieties are selected from the group consisting of: CEACAM-1, HMGB-1, phosphatidylserine, Galectin-9, LILRB2, and any combination thereof.

6. The combination of claim 1, wherein:
the second VH comprises an amino acid sequence at least 80% identical to the amino acid sequence of SEQ ID NO: 9, and the second VL comprises an amino acid sequence at least 80% identical to the amino acid sequence of SEQ ID NO: 10;
(ii) the second VH comprises an amino acid sequence at least 80% identical to the amino acid sequence of SEQ ID NO: 11, and the second VL comprises an amino acid sequence at least 80% identical to the amino acid sequence of SEQ ID NO: 12;
(iii) the second VH comprises an amino acid sequence at least 80% identical to the amino acid sequence of SEQ ID NO: 13, and the second VL comprises an amino acid sequence at least 80% identical to the amino acid sequence of SEQ ID NO: 14;
(iv) the second VH comprises an amino acid sequence at least 80% identical to the amino acid sequence of SEQ ID NO: 15, and the second VL comprises an amino acid sequence at least 80% identical to the amino acid sequence of SEQ ID NO: 16;
(v) the second VH comprises an amino acid sequence at least 80% identical to the amino acid sequence of SEQ ID NO: 17, and the second VL comprises an amino acid sequence at least 80% identical to the amino acid sequence of SEQ ID NO: 18;
(vi) the second VH comprises an amino acid sequence at least 80% identical to the amino acid sequence of SEQ ID NO: 19, and the second VL comprises an amino acid sequence at least 80% identical to the amino acid sequence of SEQ ID NO: 20;
(vii) the second VH comprises an amino acid sequence at least 80% identical to the amino acid sequence of SEQ ID NO: 21, and the second VL comprises an amino acid sequence at least 80% identical to the amino acid sequence of SEQ ID NO: 22;

(viii) the second VH comprises an amino acid sequence at least 80% identical to the amino acid sequence of SEQ ID NO: 23, and the second VL comprises an amino acid sequence at least 80% identical to the amino acid sequence of SEQ ID NO: 24;

(ix) the second VH comprises an amino acid sequence at least 80% identical to the amino acid sequence of SEQ ID NO: 25, and the second VL comprises an amino acid sequence at least 80% identical to the amino acid sequence of SEQ ID NO: 26;

(x) the second VH comprises an amino acid sequence at least 80% identical to the amino acid sequence of SEQ ID NO: 27, and the second VL comprises an amino acid sequence at least 80% identical to the amino acid sequence of SEQ ID NO: 28;

(xi) the second VH comprises an amino acid sequence at least 80% identical to the amino acid sequence of SEQ ID NO: 29, and the second VL comprises an amino acid sequence at least 80% identical to the amino acid sequence of SEQ ID NO: 30;

(xii) the second VH comprises an amino acid sequence at least 80% identical to the amino acid sequence of SEQ ID NO: 31, and the second VL comprises an amino acid sequence at least 80% identical to the amino acid sequence of SEQ ID NO: 32;

(xiii) the second VH comprises an amino acid sequence at least 80% identical to the amino acid sequence of SEQ ID NO: 33, and the second VL comprises an amino acid sequence at least 80% identical to the amino acid sequence of SEQ ID NO: 34;

(xiv) the second VH comprises an amino acid sequence at least 80% identical to the amino acid sequence of SEQ ID NO: 35, and the second VL comprises an amino acid sequence at least 80% identical to the amino acid sequence of SEQ ID NO: 36; or (xv) the second VH comprises an amino acid sequence at least 80% identical to the amino acid sequence of SEQ ID NO: 37, and the second VL comprises an amino acid sequence at least 80% identical to the amino acid sequence of SEQ ID NO: 38.

7. The combination of claim 1, wherein the first and second antibody molecules of the combination are combined in a multispecific antibody.

8. The combination of claim 7, wherein the multispecific antibody is a bispecific antibody comprising the first antibody molecule and the second antibody molecule.

9. The combination of claim 1, wherein the first and second antibody molecules of the combination are co-formulated.

10. The combination of claim 1, wherein the first and second antibody molecules of the combination are provided separately.

11. The combination of claim 1, wherein the combination additionally comprises an agent that inhibits SIRPα signaling.

12. The combination of claim 11, wherein the agent that inhibits SIRPα signaling is selected from the group consisting of: (i) an antibody molecule that binds CD47 and inhibits interaction between CD47 and SIRPα; (ii) an antibody molecule that binds SIRPα and inhibits interaction between CD47 and SIRPα; and (iii) an SIRPα-antibody molecule fusion protein.

13. A combination comprising a first antibody molecule that specifically binds to CD70 and a second antibody molecule that specifically binds to TIM-3, wherein the first antibody molecule comprises a first VH comprising HCDR1, HCDR2 and HCDR3 regions, and a first VL comprising LCDR1, LCDR2 and LCDR3 regions, wherein the HCDR1, HCDR2, HCDR3, LCDR1, LCDR2 and LCDR3 regions of the first VH and the first VL comprise the amino acid sequences set forth in SEQ ID NOs: 1, 2, 3, 5, 6, and 7, respectively, and wherein the second antibody molecule comprises a (second VH comprising HCDR1, HCDR2 and HCDR3 regions, and a (second VL comprising LCDR1, LCDR2 and LCDR3 regions, wherein the HCDR1, HCDR2, HCDR3, LCDR1, LCDR2 and LCDR3 regions of the second VH and the second VL comprise the amino acid sequences set forth in SEQ ID NOs: 56, 57, 58, 95, 96, and 97, respectively.

14. The combination of claim 13, wherein the second VH comprises an amino acid sequence at least 80% identical to the amino acid sequence of SEQ ID NO: 21, and the second VL comprises an amino acid sequence having at least 80% identical to the amino acid sequence of SEQ ID NO: 22.

15. The combination of claim 14, wherein the second VH comprises the amino acid sequence of SEQ ID NO: 21, and the second VL comprises the amino acid sequence of SEQ ID NO: 22.

16. The combination of claim 13, wherein the first VH comprises an amino acid sequence at least 70% identical to the amino acid sequence of SEQ ID NO: 4, and the first VL comprises an amino acid sequence at least 70% identical to the amino acid sequence of SEQ ID NO: 8.

17. The combination of claim 16, wherein the first VH comprises the amino acid sequence of SEQ ID NO: 4, and the first VL comprises the amino acid sequence of SEQ ID NO: 8.

18. The combination of claim 13, wherein at least one of the antibody molecules comprises a defucosylated antibody domain.

19. The combination of claim 16, wherein the first antibody molecule is ARGX-110.

20. The combination of claim 13, wherein the second antibody molecule is an IgG1 antibody molecule.

21. The combination of claim 1, wherein at least one of the antibody molecules comprises a defucosylated antibody domain.

22. The combination of claim 1, wherein the second antibody molecule is an IgG1 antibody molecule.

23. The combination of claim 2, wherein the first VH comprises the amino acid sequence of SEQ ID NO: 4, and the first VL comprises the amino acid sequence of SEQ ID NO: 8.

24. The combination of claim 6, wherein:

the second VH comprises the amino acid sequence of SEQ ID NO: 9, and the second VL comprises the amino acid sequence of SEQ ID NO: 10;

(ii) the second VH comprises the amino acid sequence of SEQ ID NO: 11, and the second VL comprises the amino acid sequence of SEQ ID NO: 12;

(iii) the second VH comprises the amino acid sequence of SEQ ID NO: 13, and the second VL comprises the amino acid sequence of SEQ ID NO: 14;

(iv) the second VH comprises the amino acid sequence of SEQ ID NO: 15, and the second VL comprises the amino acid sequence of SEQ ID NO: 16;
(v) the second VH comprises the amino acid sequence of SEQ ID NO: 17, and the second VL comprises the amino acid sequence of SEQ ID NO: 18;
(vi) the second VH comprises the amino acid sequence of SEQ ID NO: 19, and the second VL comprises the amino acid sequence of SEQ ID NO: 20;
(vii) the second VH comprises the amino acid sequence of SEQ ID NO: 21, and the second VL comprises the amino acid sequence of SEQ ID NO: 22;
(viii) the second VH comprises the amino acid sequence of SEQ ID NO: 23, and the second VL comprises the amino acid sequence of SEQ ID NO: 24;
(ix) the second VH comprises the amino acid sequence of SEQ ID NO: 25, and the second VL comprises the amino acid sequence of SEQ ID NO: 26;
(x) the second VH comprises the amino acid sequence of SEQ ID NO: 27, and the second VL comprises the amino acid sequence of SEQ ID NO: 28;
(xi) the second VH comprises the amino acid sequence of SEQ ID NO: 29, and the second VL comprises the amino acid sequence of SEQ ID NO: 30;
(xii) the second VH comprises the amino acid sequence of SEQ ID NO: 31, and the second VL comprises the amino acid sequence of SEQ ID NO: 32;
(xiii) the second VH comprises the amino acid sequence of SEQ ID NO: 33, and the second VL comprises the amino acid sequence of SEQ ID NO: 34;
(xiv) the second VH comprises the amino acid sequence of SEQ ID NO: 35, and the second VL comprises the amino acid sequence of SEQ ID NO: 36; or
(xv) the second VH comprises the amino acid sequence of SEQ ID NO: 37, and the second VL comprises the amino acid sequence of SEQ ID NO: 38.

* * * * *

UNITED STATES PATENT AND TRADEMARK OFFICE
CERTIFICATE OF CORRECTION

| | |
|---|---|
| PATENT NO. | : 11,530,271 B2 |
| APPLICATION NO. | : 16/249480 |
| DATED | : December 20, 2022 |
| INVENTOR(S) | : Luc Van Rompaey et al. |

It is certified that error appears in the above-identified patent and that said Letters Patent is hereby corrected as shown below:

In the Claims

At Column 112, Line number 23, for Claim 2 replace:
"SEQ ID NO:"
With:
--SEQ ID NO: 4--

Signed and Sealed this
Seventh Day of February, 2023

Katherine Kelly Vidal
*Director of the United States Patent and Trademark Office*